United States Patent
Desai et al.

(10) Patent No.: US 9,212,143 B2
(45) Date of Patent: Dec. 15, 2015

(54) SMALL MOLECULE INHIBITORS OF PROTEIN KINASES

(75) Inventors: Ketan Desai, Easton, PA (US); Renee Desai, Easton, PA (US)

(73) Assignee: LEVOLTA PHARMACEUTICALS, INC., Bethlehem, PA (US)

( * ) Notice: Subject to any disclaimer, the term of this patent is extended or adjusted under 35 U.S.C. 154(b) by 220 days.

(21) Appl. No.: 13/696,205

(22) PCT Filed: Nov. 2, 2010

(86) PCT No.: PCT/US2010/055110
§ 371 (c)(1),
(2), (4) Date: Nov. 13, 2012

(87) PCT Pub. No.: WO2011/139295
PCT Pub. Date: Nov. 10, 2011

(65) Prior Publication Data
US 2013/0058980 A1    Mar. 7, 2013

Related U.S. Application Data

(63) Continuation-in-part of application No. 12/774,230, filed on May 5, 2010, now Pat. No. 8,389,525.

(51) Int. Cl.
| | |
|---|---|
| A61K 31/513 | (2006.01) |
| A61K 31/519 | (2006.01) |
| C07D 213/85 | (2006.01) |
| A61K 31/15 | (2006.01) |
| A61K 31/382 | (2006.01) |
| A61K 31/404 | (2006.01) |
| A61K 31/426 | (2006.01) |
| A61K 31/44 | (2006.01) |
| A61K 31/498 | (2006.01) |
| A61K 31/517 | (2006.01) |
| C07D 335/12 | (2006.01) |
| C07D 239/70 | (2006.01) |
| C07D 239/95 | (2006.01) |
| C07D 241/36 | (2006.01) |
| C07D 277/06 | (2006.01) |
| C07D 495/04 | (2006.01) |
| C07D 209/38 | (2006.01) |
| C12N 9/12 | (2006.01) |
| C12Q 1/48 | (2006.01) |
| C12N 5/0787 | (2010.01) |

(52) U.S. Cl.
CPC .............. *C07D 213/85* (2013.01); *A61K 31/15* (2013.01); *A61K 31/382* (2013.01); *A61K 31/404* (2013.01); *A61K 31/426* (2013.01); *A61K 31/44* (2013.01); *A61K 31/498* (2013.01); *A61K 31/517* (2013.01); *A61K 31/519* (2013.01); *C07D 209/38* (2013.01); *C07D 239/70* (2013.01); *C07D 239/95* (2013.01); *C07D 241/36* (2013.01); *C07D 277/06* (2013.01); *C07D 335/12* (2013.01); *C07D 495/04* (2013.01); *C12N 5/0642* (2013.01); *C12N 9/1205* (2013.01); *C12Q 1/485* (2013.01); *C12N 2501/727* (2013.01); *G01N 2500/04* (2013.01); *G01N 2800/122* (2013.01); *G01N 2800/24* (2013.01); *G01N 2800/7095* (2013.01)

(58) Field of Classification Search
CPC ........................... A61K 31/513; A61K 31/519
See application file for complete search history.

(56) References Cited

U.S. PATENT DOCUMENTS 8,389,525 B2    3/2013    Desai et al.

FOREIGN PATENT DOCUMENTS

WO    2008008264 A2    1/2008

OTHER PUBLICATIONS

Rathod et al. Indian Journal of Heterocyclic Chemistry, 2000, pp. 1-5.*
Silverman et al. http:www.naccme.com, Jul. 2013, pp. 1-2.*
De Leon, G., et al., "An In Vitro Screen of Bacterial Lipopolysaccharide Biosynthetic Enzymes Identifies an Inhibitor of ADP-Heptose Biosynthesis", "Chemistry & Biology", Apr. 2006, pp. 437-441, vol. 13.
Ito, N., et al., "A Medium-Term Rat Liver Bioassay for Rapid In Vivo Detection of Carcinogenic Potential of Chemicals", "Cancer Sci", Jan. 2003, pp. 3-8, vol. 94, No. 1.
Rodinovskaya, L., et al., "One-Pot Synthesis of Diverse 4-Di(tri)fluoromethyl-3-cyanopyridine-2(1H)-thiones and Their Utilities in the Cascade Synthesis of Annulated Heterocycles", "J. Comb. Chem.", Feb. 13, 2008, pp. 313-322, vol. 10, No. 2.
Yuan, Y., et al., "Toward Homogeneous Erythropoietin: Fine Tuning of the C-Terminal Acyl Donor in the Chemical Synthesis of the Cys29-Gly77 Glycopeptide Domain", "J. Am. Chem. Soc.", Mar. 31, 2009, pp. 5432-5437, vol. 131.

* cited by examiner

*Primary Examiner* — Samira Jean-Louis
(74) *Attorney, Agent, or Firm* — Andrews Kurth LLP; David Bradin

(57) ABSTRACT

Compounds that modulate, for example, that inhibit, syk kinase, and, optionally other kinases. The compounds can be used to treat a variety of disorders, including inflammatory disorders and autoimmune disorders.

9 Claims, 11 Drawing Sheets

SMALL MOLECULE INHIBITORS OF PROTEIN KINASES

CROSS-REFERENCE TO RELATED APPLICATIONS

This application is a U.S. national phase application under the provisions of 35 U.S.C. §371 of International Patent Application No. PCT/US10/55110 filed Nov. 2, 2010, which in turn claims priority of U.S. patent application Ser. No. 12/774,230 filed May 5, 2010. The disclosures of such international patent application and US priority patent application are hereby incorporated herein by reference in their respective entireties, for all purposes.

FIELD OF THE INVENTION

This invention provides compounds that inhibit protein kinases, prodrugs of the compounds, intermediates and methods of synthesizing the compounds and/or prodrugs, pharmaceutical compositions comprising the compounds and/or prodrugs and methods of using the compounds and/or prodrugs in a variety of contexts, including, for example, in the treatment and/or prevention of various diseases that are responsive to protein kinase inhibition and/or that are mediated, at least in part, by inappropriate kinase activity.

BACKGROUND OF THE INVENTION

Protein Kinases

Protein kinases constitute a large family of structurally related enzymes that are responsible for the control of a variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylated (e.g., protein-tyrosine, protein-serine/threonine, lipids, etc.). Sequence motifs have been identified that generally correspond to each of these kinase families (See, for example, Hanks, S. K., Hunter, T., FASEB J., 9:576 596 (1995); Knighton et al., Science, 253:407 414 (1991); Hiles et al., Cell, 70:419 429 (1992); Kunz et al., Cell, 73:585 596 (1993); Garcia-Bustos et al., EMBO J., 13:2352 2361 (1994)).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These 2 phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and H2O2), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

SYK Kinase

Spleen tyrosine kinase (Syk) is a 72-kDa cytoplasmic protein tyrosine kinase that is expressed in a variety of hematopoietic cells and is an essential element in several cascades that couple antigen receptors to cellular responses. Syk plays a pivotal role in signaling through the Fc receptor and integrins in both neutrophils and macrophages. Syk is also important for signaling of the high affinity IgE receptor, Fc εR1, in mast cells and in receptor antigen signaling in T and B lymphocytes. The various Fc receptor signal transduction pathways present in phagocytes, mast, T and B cells have common features. The ligand binding domain of the receptor lacks intrinsic tyrosine kinase activity. However, they interact with transducing subunits that contain immunoreceptor tyrosine based activation motifs (ITAMs) (M. Reth, Nature, 1989, 338, pages 383-384). These motifs are present in both the β and γ subunits of the Fc εR1, in the ξ-subunit the of T cell receptor (TCR) and in the IgGα and IgGβ subunits of the B cell receptor (BCR) (N. S. van Oers and A. Weiss, Seminars in Immunology, 1995, 7, pages 227-236). Upon binding of antigen and multimerization, the ITAM residues are phosphorylated by protein tyrosine kinases of the Src family. Syk belongs to a unique class of tyrosine kinases that have two tandem Src homology 2 (SH2) domains and a C terminal catalytic domain. These SH2 domains bind with high affinity to ITAMs and this SH2-mediated association of Syk with an activated receptor stimulates Syk kinase activity and localizes Syk to the plasma membrane.

In Syk deficient mice, mast cell degranulation is inhibited, suggesting that this is an important target for the development of mast cell stabilizing agents (P. S. Costello, Oncogene, 1996, 13, pages 2595-2605). Similar studies have demonstrated a critical role for Syk in BCR and TCR signaling (A. M. Cheng, Nature, 1995, 378, pages 303-306, (1995) and D. H. Chu et al., Immunological Reviews, 1998, 165, pages 167-180). Syk also appears to be involved in eosinophil survival in response to IL-5 and GM-CSF (S. Yousefi et al., J. Exp. Med., 1996, 183, pages 1407-1414). Despite the key role of Syk in mast cell, BCR and T cell signaling, little is known about the mechanism by which Syk transmits downstream effectors. Two adaptor proteins, BLNK (B cell Linker protein, SLP-65) and SLP-76 have been shown to be substrates of Syk in B cells and mast cells respectively and have been postulated to interface Syk with downstream effectors (M. Ishiai et al., Immunity, 1999, 10, pages 117-125 and L. R. Hendricks-Taylor et al., J. Biol. Chem, 1997, 272, pages 1363-1367). In addition Syk appears to play an important role in the CD40 signaling pathway, which plays an important role in B cell proliferation (M. Faris et al., J. Exp. Med., 1994, 179, pages 1923-1931).

Syk is further involved in the activation of platelets stimulated via the low-affinity IgG receptor (Fcγ-RIIA) or stimulated by collagen (F. Yanaga et al., Biochem. J., 1995, 311, (Pt. 2) pages 471-478).

Crosslinking of Fc receptors, such as the high affinity receptors for IgG, IgE (FcεRI), as well as stimulation through integrins, activates signaling cascades in immune cells that result in the activation of the cells and/or release of preformed mediators. These mediators include molecules such as histamine from mast cells and lactoferrin, catalase, and elastase from neutrophils via degranulation. It also leads to the synthesis and release of other mediators, including cytokines such as TNF alpha and IL 2 as well as nitric oxide, leukotrienes, prostaglandins and platelet-activating factors (PAFs), which play important roles in inflammatory reactions.

The signaling cascade(s) activated by crosslinking Fc receptors such as FcεRI and/or FcγRI comprises an array of cellular proteins. Among the most important intracellular signal propagators are the tyrosine kinases. And, an important tyrosine kinase involved in the signal transduction pathways associated with crosslinking the FcεRI and/or FcγRI receptors, as well as other signal transduction cascades, is Syk kinase (see Valent et al., 2002, Intl. J. Hematol. 75(4):357-362 for review). The mediators released as a result of FcεRI and/or FcγRI receptor cross-linking are responsible for, or play important roles in, the manifestation of numerous events, some of which are adverse. Therefore, there exists a need for compounds which are able to effectively inhibit Syk kinase.

Kinase Diseases

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or underproduction of cytokines or growth factors also participating in the transduction of signal upstream or downstream of the kinase. In all of these instances, selective inhibition of the action of the kinase might be expected to have a beneficial effect.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

Considering the lack of currently available treatment options for the majority of the conditions associated with protein kinases, there is still a great need for new therapeutic agents that inhibit these protein targets. The present invention provides such therapeutic agents, and methods of treatment using the agents.

SUMMARY OF THE INVENTION

Compounds that function to modulate kinases, for example, by inhibiting kinases, such as Syk kinase, are disclosed. In some embodiments, the compounds are inhibitors or antagonists, and in other cases, promoters or agonists. Methods of treatment using the compounds, and pharmaceutical compositions including the compounds, are also disclosed.

In one embodiment, the compound has one of the following formulas a-i:

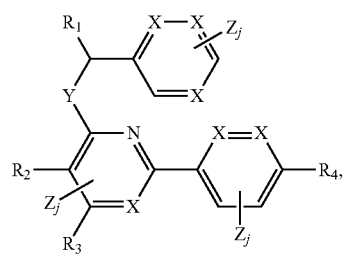

(a)

wherein:

$R_1$ and $R_2$ are independently selected from the group consisting of —C(O)OR$_5$, —C(S)OR$_5$, —C(NR$_5$)OR$_5$, —C(O)SR$_5$, —C(S)SR$_5$, —C(NR$_5$)SR$_5$, —C(O)N(R$_5$)$_2$, —C(S)N(R$_5$)$_2$, —C(NR$_5$)N(R$_5$)$_2$, —N(R$_5$)C(O)OR$_5$, —N(R$_5$)C(S)OR$_5$, —N(R$_5$)C(NR$_5$)OR$_5$, —N(R$_5$)C(O)SR$_5$, —N(R$_5$)C(S)SR$_5$, —N(R$_5$)C(NR$_5$)SR$_5$, —N(R$_5$)C(O)N(R$_5$)$_2$, —N(R$_5$)C(S)N(R$_5$)$_2$, —N(R$_5$)C(NR$_5$)N(R$_5$)$_2$, —NO$_2$, —SOR$_5$, —SO$_2$R$_5$; —SO$_3$R$_5$; —CN, —PO$_4$R$_5$, —C(O)R$_5$, —C(S)R$_5$, and —C(NR$_5$)R$_5$, $R_3$ is selected from the group consisting of —C$_{1-6}$ perfluoroalkyl, such as trifluoromethyl and pentafluoroethyl, —C$_{1-6}$ haloalkyl, —C$_{1-6}$ alkyl, and $R_4$ is selected from the group consisting of halo, such as fluoro, chloro, bromo, and iodo; nitro; cyano; carbonyls, including —C(O)OR$_5$, —C(O)R$_5$, —C(O)N(R$_5$)$_2$, and —C(O)SR$_5$; —SOR$_5$; —SO$_2$R$_5$; —SO$_3$R$_5$; and —PO$_4$R$_5$, and in one embodiment is halo, such as bromo;

$R_5$ is a substituent selected from the group consisting of H, —C$_{1-6}$ alkyl, —C$_{1-6}$ alkylaryl, -aryl-C$_{1-6}$ alkyl, —C$_{1-6}$ alkylheteroaryl, -heteroaryl-C$_{1-6}$alkyl, -aryl, and -heteroaryl.

Z is selected from the group consisting of C$_{1-6}$ alkyl, alkenyl, heterocyclyl, aryl, heteroaryl, halo, —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)O R", —SO$_2$R', —SO$_2$NR'R", and —NR'SO$_2$R", where R' and R" are individually hydrogen, C$_{1-6}$ alkyl, cycloalkyl, heterocyclyl, aryl, or arylalkyl, wherein the aryl or heteroaryl rings can be substituted at any free position with Z, j is an integer from 0 to the number of available positions on the aryl or heteroaryl ring to which the Z substituent is attached, X is, individually, N, or C bonded to H or a substituent Z, and, in one embodiment, no more than two X are N within any ring structure, and Y is O, S, or NR$_5$.

In one embodiment, R$_5$ is H.

In one embodiment, all X are carbon bonded to H or a substituent Z. In one aspect of this embodiment, all X are C—H.

In one embodiment, the compound of Formula (a) has the structure:

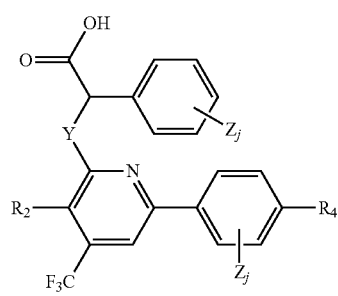

In one embodiment, the compound of Formula (a) has the structure:

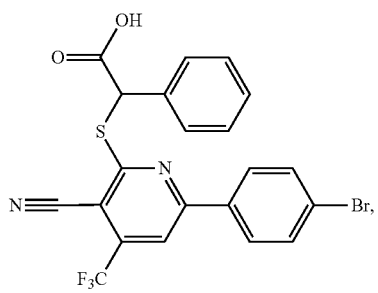 [SMILES: N#Cc1c(C(F)(F)F)cc(-c2ccc(Br)cc2)nc1SC(C(=O)O)c1ccccc1]

and in another embodiment, this structure is specifically excluded from the compounds of Formula (a).

Compounds of Formula (b) generally have the formula:

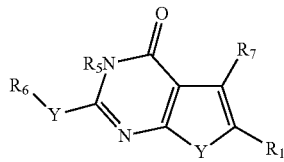

or the isomeric form:

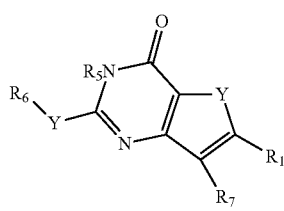

Isomeric form wherein:

Y, $R_1$ and $R_5$ are as defined above with respect to Formula (a), $R_6$ is $C_{1-6}$-alkylaryl, $C_{1-6}$-alkylheteroaryl, aryl, or heteroaryl, wherein the aryl or heteroaryl ring in the aryl, aralkyl, alkheteroaryl, or heteroaryl substituents is optionally substituted with one to three substituents, Z, as described above, wherein in one embodiment, the substituent, Z, is a substituent defined as $R_2$ herein, and in another embodiment, is defined as being selected from the group consisting of C(S)OR$_5$, —C(NR$_5$)OR$_5$, —C(O)SR$_5$, —C(S)SR$_5$, —C(NR$_5$)SR$_5$, —C(O)N(R$_5$)$_2$, —C(S)N(R$_5$)$_2$, —C(NR$_5$)N(R$_5$)$_2$, —N(R$_5$)C(O)OR$_5$, —N(R$_5$)C(S)OR$_5$, —N(R$_5$)C(NR$_5$)OR$_5$, —N(R$_5$)C(O)SR$_5$, —N(R$_5$)C(S)SR$_5$, —N(R$_5$)C(NR$_5$)SR$_5$, —N(R$_5$)C(O)N(R$_5$)$_2$, —N(R$_5$)C(S)N(R$_5$)$_2$, —N(R$_5$)C(NR$_5$)N(R$_5$)$_2$, —SOR$_5$, —SO$_2$R$_5$, —SO$_3$R$_5$, —PO$_4$R$_5$, —C(O)R$_5$, —C(S)R$_5$, and —C(NR$_5$)R$_5$, $R_7$ is a substituent selected from the group consisting of H, —C$_{1-6}$ alkyl, such as methyl, —C$_{1-6}$ alkylaryl, -aryl-C$_{1-6}$ alkyl, —C$_{1-6}$ alkylheteroaryl, -heteroaryl-C$_{1-6}$alkyl, -aryl, and -heteroaryl.

In one embodiment, $R_5$ is H.

In one embodiment, $R_6$ is $C_{1-6}$-alkylaryl or $C_{1-6}$-alkylheteroaryl.

In one embodiment, the compound of Formula (b) has the structure:

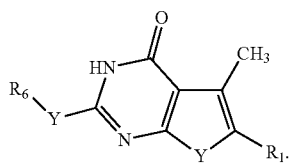

In another embodiment, the compound of Formula (b) has the structure:

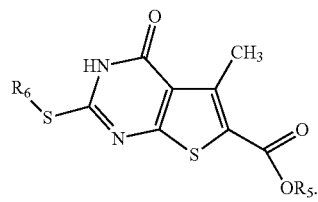

In still another embodiment, the compound of Formula (b) has the structure:

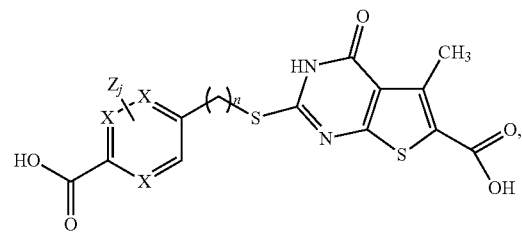

wherein Z, X, and j are as defined above with respect to Formula (a), preferably, no more than two X are N within any ring structure, and n is an integer of from 1 to 3.

In still another embodiment, the compound of Formula (b) has the structure:

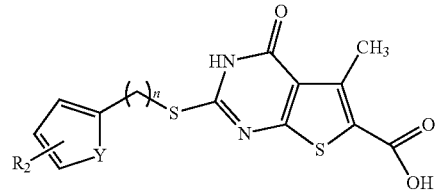

A specific compound within the scope of Formula (b) is as follows:

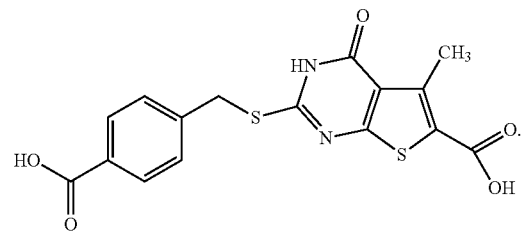 [SMILES: Cc1c(C(=O)O)sc2nc(SCc3ccc(C(=O)O)cc3)[nH]c(=O)c12]

In one embodiment, this compound is specifically excluded from the scope of Formula (b).

Compounds of Formula (c) have the general formula

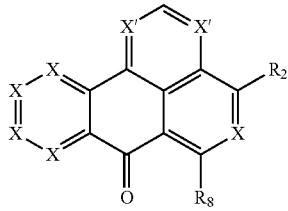

Formula (c)

wherein:

X' is N or C bonded to H or a substituent, Z, and at least one X' is N;

X, Z, j, and $R_6$ are as previously defined, no more than three X, and preferably, no more than two X, are N within any ring structure, and $R_8$ is selected from the group consisting of $OR_5$, $SR_5$, and $N(R_5)_2$.

In one embodiment, the compounds of Formula (c) have the formula:

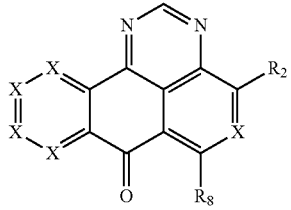

wherein X, Z, j, and $R_2$ are as previously defined, no more than three X, and preferably, no more than two X, are N within any ring structure, and $R_8$ is selected from the group consisting of $OR_5$, $SR_5$, and $N(R_5)_2$.

In one embodiment, the compounds of Formula (c) have the formula:

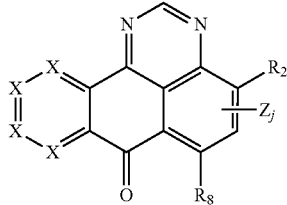

In one embodiment, the compounds of Formula (c) have one of the following formulas:

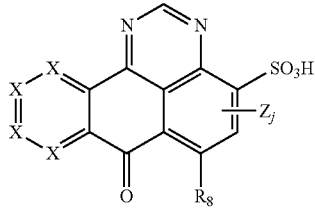

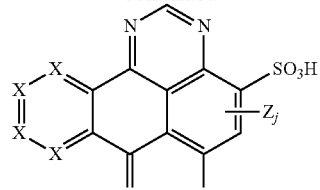

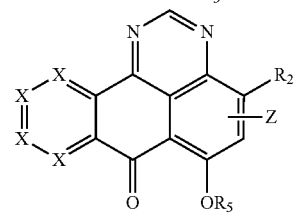

where Z, j, X, and $R_5$ are as previously defined, and no more than three X, and preferably, no more than two X, are N within any ring structure.

A specific compound within the scope of Formula (c) is

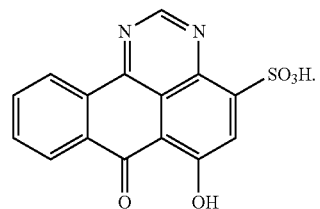 [SMILES: O=C1c2ccccc2-c2ncnc3c(S(=O)(=O)O)cc(O)c1c23]

However, in one embodiment, this compound is specifically excluded from the scope of Formula (c).

The compounds of Formula (d) generally have the formula:

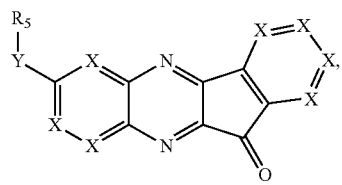

wherein X, Y, and $R_5$, are as defined above, and no more than three X, in one embodiment, no more than two X, and in another embodiment, zero or one X, are N within any ring structure.

In one embodiment, the compounds have the formula:

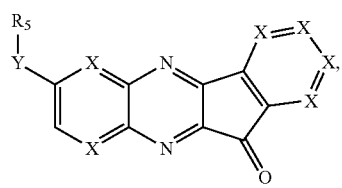

wherein X, Z, and j are as defined above, and no more than three X, and preferably, no more than two X, are N within any ring structure.

The compounds of Formula (d) can fall within the following sub-formulas:

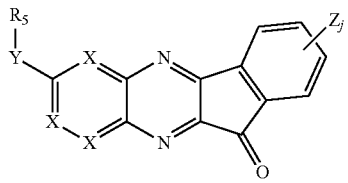

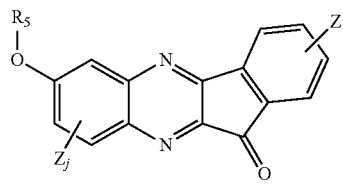

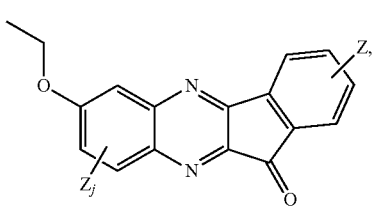

as well as positional isomers thereof, wherein Z, j, X, Y, and $R_5$ are as defined above, and preferably, no more than two X are N within any ring structure.

In one embodiment, the compound of Formula (d) has the formula:

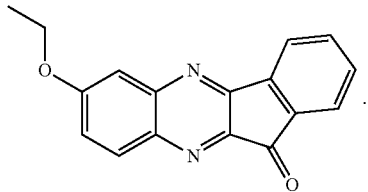 [SMILES: CCOc1ccc2nc3c(nc2c1)-c1ccccc1C3=O]

However, in one embodiment, this compound is specifically excluded from the scope of Formula (d).

The compounds of Formula (e) generally have the formula:

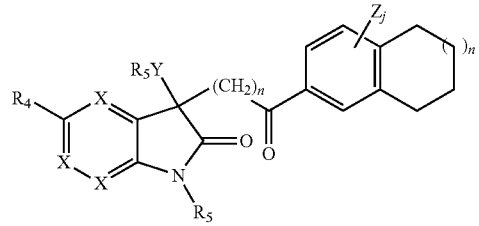

wherein X, Y, Z, j, $R_4$, $R_5$, and n are as defined above.

In one embodiment, the compounds have the formula:

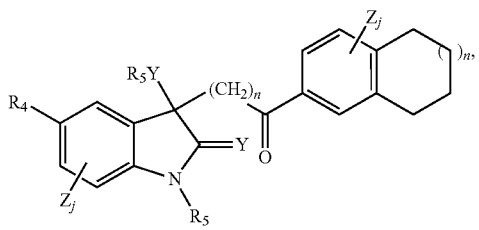

wherein Y, Z, j, $R_4$, $R_5$, and n are as defined above.

The compounds of Formula (e) can fall within the following sub-formulas:

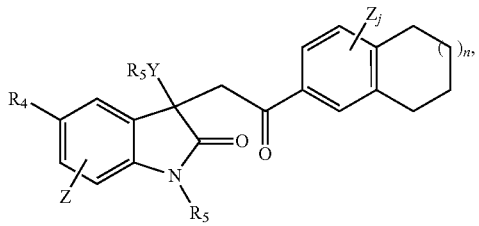

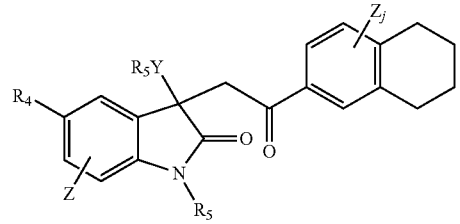

wherein Y, Z, j, $R_4$, $R_5$, and n are as defined above.

More specifically, the compounds of Formula (e) can have the following formulas:

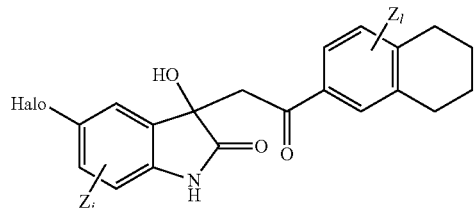

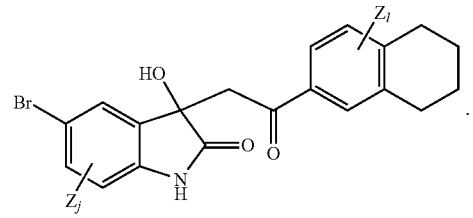

A specific compound falling within the scope of Formula (e) has the following formula:

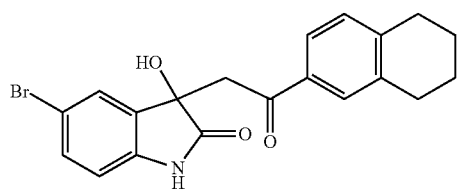

However, in one embodiment, this compound is specifically excluded from the scope of Formula (e).

The compounds of Formula (f) generally have the formula:

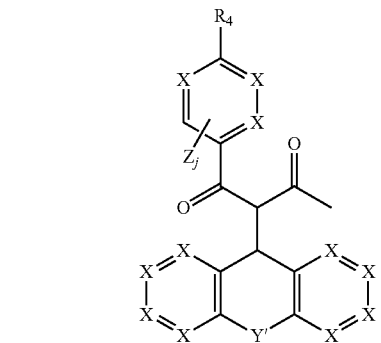

wherein X, Z, j, and $R_4$ are as defined above, Y' is O, S, $NR_5$, $-CH_2O$, $-CH_2S$, or $-CH_2NR_5$, and no more than three X, and preferably, no more than two X, are N within any ring structure.

Specific compounds within the scope of Formula (f) include the following:

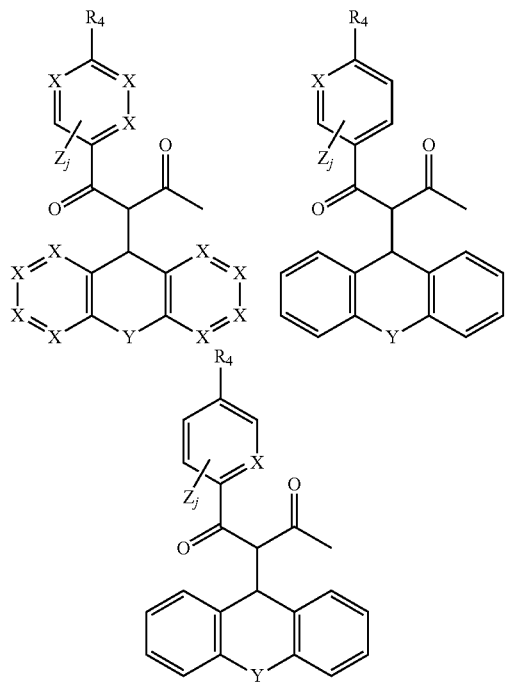

wherein X, Y, Z, j, and $R_4$ are as defined above, and no more than three X, and preferably, no more than two X, are N within any ring structure.

Further compounds within the scope of Formula (f) include the following:

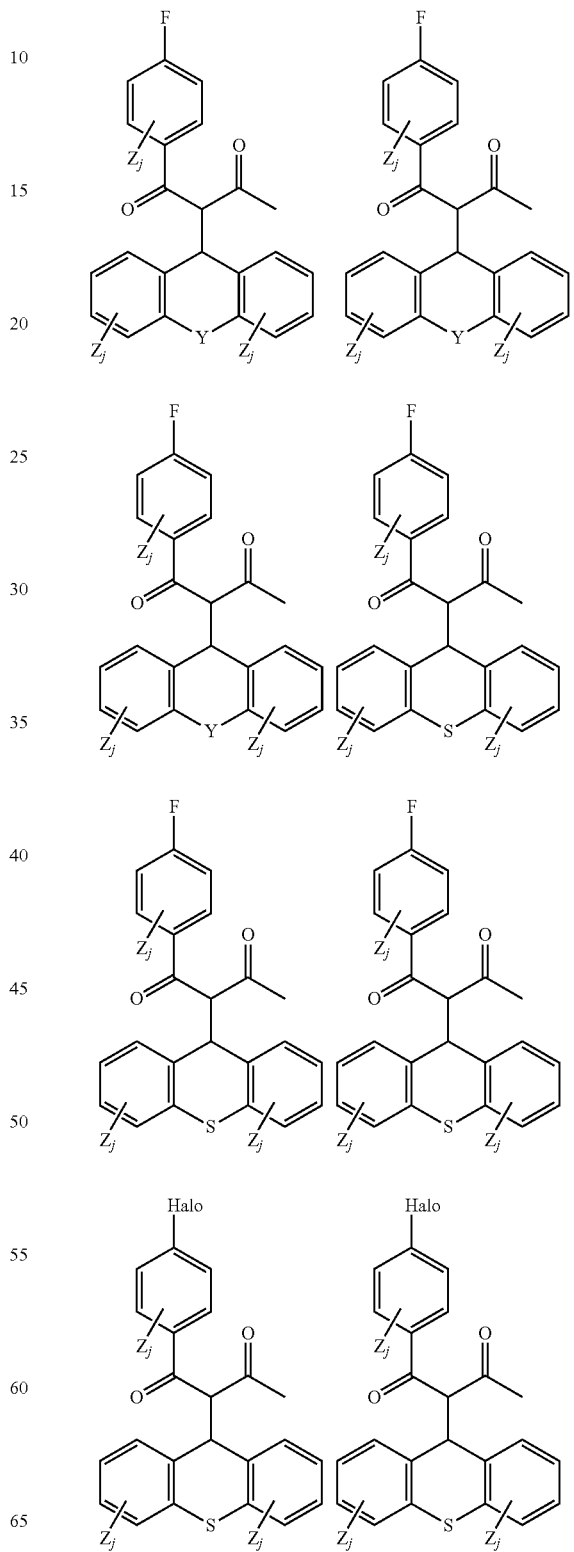

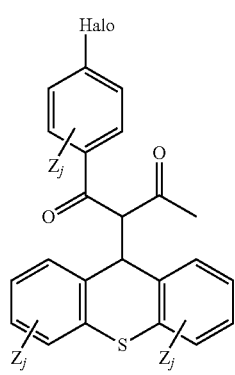

wherein Y, Z, and j are as defined above.

A specific compound within the scope of Formula (f) is:

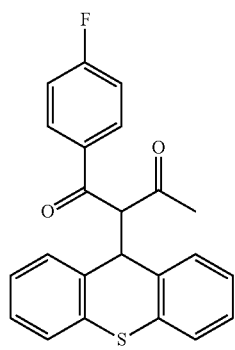

However, in one embodiment, this compound is specifically excluded from the scope of Formula (f).

The compounds of Formula (g) generally have the formula:

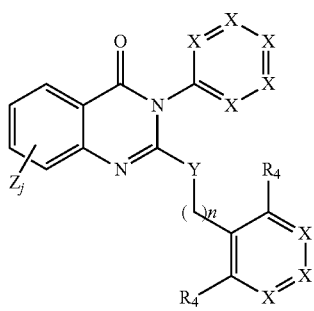

wherein X, Y, Z, j, n, and $R_4$ are as defined above, and no more than three X, and preferably, no more than two X, are N within any ring structure.

Specific compounds within Formula (g) include the following:

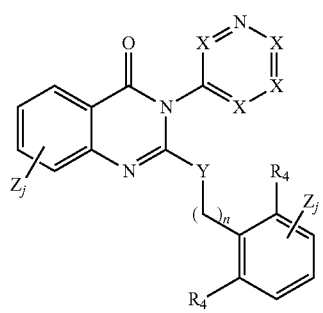

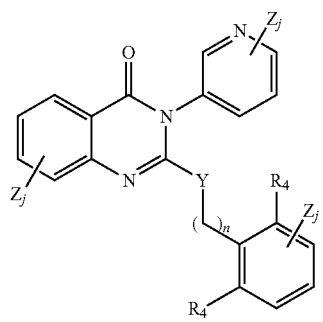

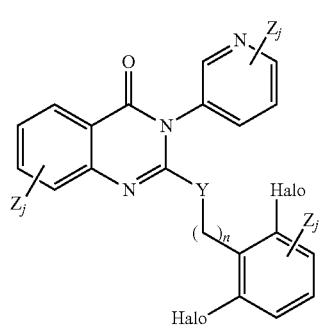

and

Specific compounds within Formula (g) also include the following:

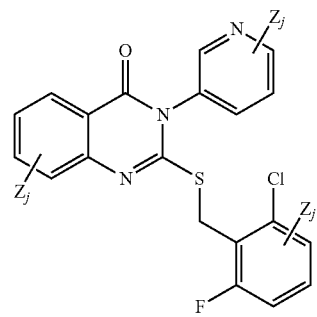

wherein Z and j are as defined above.

A specific compound within Formula (g) is as follows:

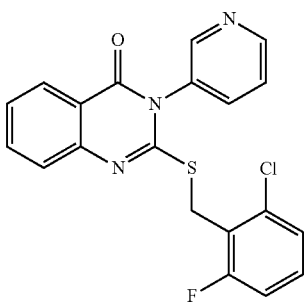

However, in one embodiment, this compound is specifically excluded from the scope of Formula (g).

The compounds of Formula (h) generally have the following formula:

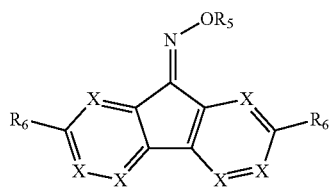

wherein X, $R_5$, and $R_6$ are as defined above, and, in one embodiment, no more than two X are N within any ring structure, and in another embodiment, no more than one X is N within any ring structure.

In one embodiment, where X is C bound to H or a substituent, Z, Z is selected from the group consisting of $C_{1-6}$ alkyl, alkenyl, heterocyclyl, aryl, heteroaryl, halo, —OR', —NR'R", —CF$_3$, —CN, —C$_2$R', —SR', —N$_3$, —NR'C(=O)R", —C(=O)R', —OC(=O)R', —OC(=O)NR'R", —NR'C(=O)O R", —SO$_2$R', —SO$_2$NR'R", and —NR'SO$_2$R", where R' and R" are individually hydrogen, $C_{1-6}$ alkyl, cycloalkyl, heterocyclyl, aryl, or arylalkyl, wherein the aryl or heteroaryl rings can be substituted at any free position with Z, More specifically, the compounds of Formula (h) can have the following structure:

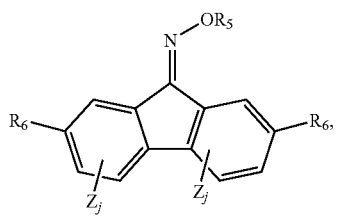

wherein Z, j, $R_5$, and $R_6$ are as defined above.

Still more specifically, the compounds of Formula (h) can have the following structure:

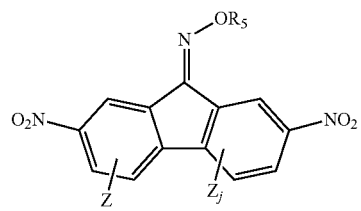

wherein Z, j, and $R_5$ are as defined above.

A specific compound within the Formula (h) has the formula:

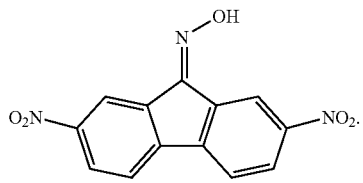 [SMILES: O=[N+]([O-])c1ccc2c(c1)C(=NO)c1cc([N+](=O)[O-])ccc1-2]

However, in one embodiment, this compound is specifically excluded from the scope of Formula (h).

The compounds of Formula (i) have the following general formula:

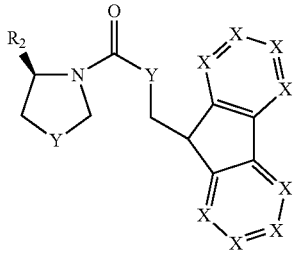

wherein X, Y, n, and $R_2$ are as defined above, and no more than 3 X, and preferably, no more than two X, are N within any ring structure.

In one embodiment, $R_2$ is selected from the group consisting of C(S)OR$_5$, —C(NR$_5$)OR$_5$, —C(O)SR$_5$, —C(S)SR$_5$, —C(NR$_5$)SR$_5$, —C(S)N(R$_5$)$_2$, —C(NR$_5$)N(R$_5$)$_2$, —N(R$_5$)C(O)OR$_5$, —N(R$_5$)C(S)OR$_5$, —N(R$_5$)C(NR$_5$)OR$_5$, —N(R$_5$)C(O)SR$_5$, —N(R$_5$)C(S)SR$_5$, —N(R$_5$)C(NR$_5$)SR$_5$, —N(R$_5$)C(O)N(R$_5$)$_2$, —N(R$_5$)C(S)N(R$_5$)$_2$, —N(R$_5$)C(NR$_5$)N(R$_5$)$_2$, —NO$_2$, —SOR$_5$, —SO$_2$R$_5$, —SO$_3$R$_5$, —CN, —PO$_4$R$_5$, —C(O)R$_5$, —C(S)R$_5$, and —C(NR$_5$)R$_5$, More specific compounds within Formula (i) fall within the following formulas:

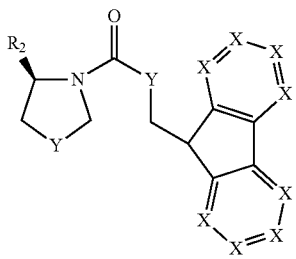

-continued

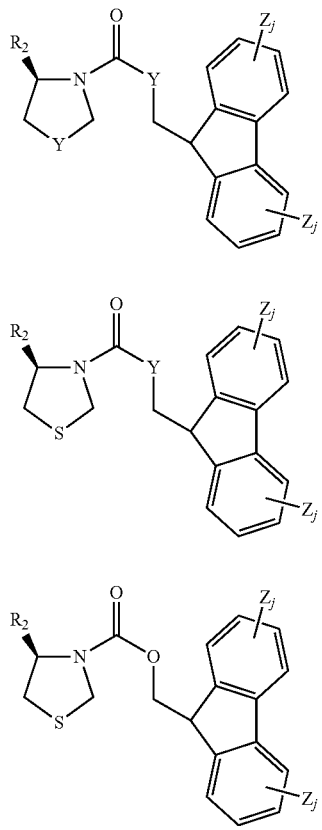

wherein Z, j, X, Y, n, and $R_6$ are as defined above, and no more than 3X, in one embodiment, no more than two X, and in another embodiment, no more than zero or one X, are N within any ring structure.

Additional compounds within the scope of Formula (i) include the following:

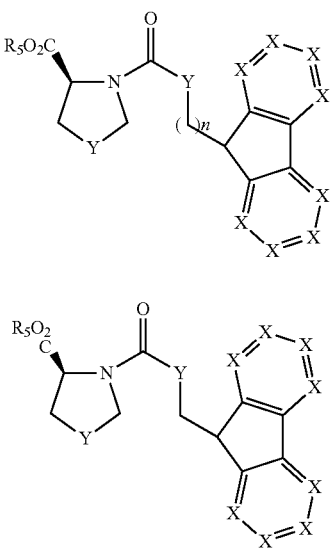

-continued

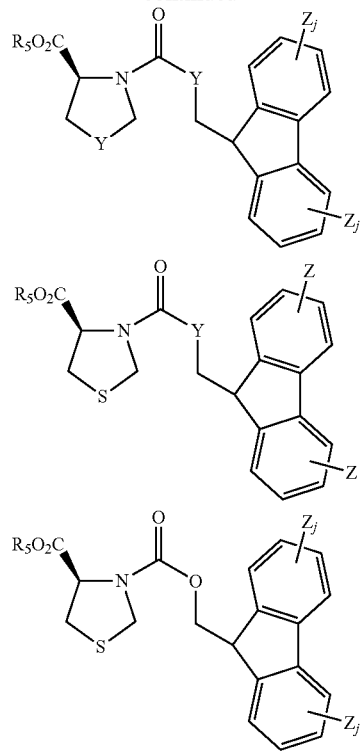

wherein Z, j, X, Y, and n are as defined above, and no more than 3X, and preferably, no more than two X, are N within any ring structure.

Still more specific compounds falling within the scope of Formula (i) include the following:

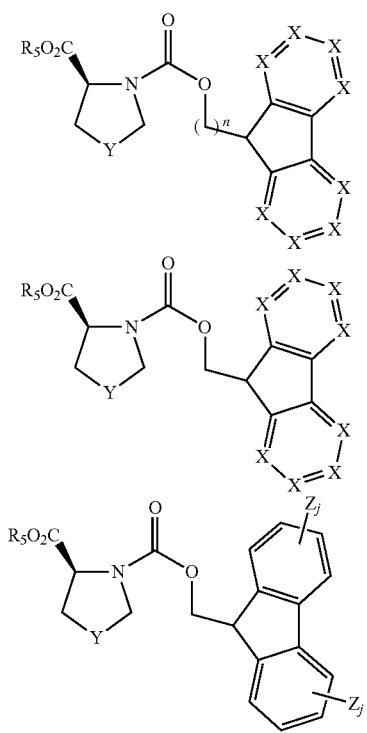

-continued

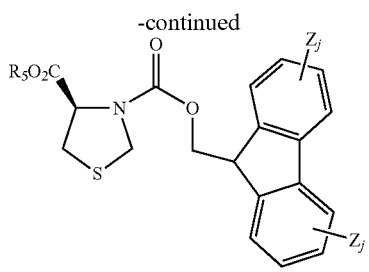

wherein Z, j, X, Y, and n are as defined above, and no more than 3X, and preferably, no more than two X, are N within any ring structure.

A specific compound falling within the scope of Formula (i) is the following:

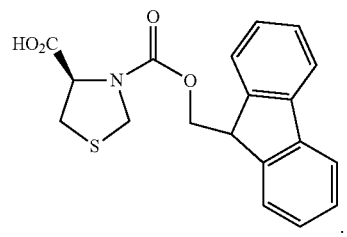 [SMILES: O=C(O)[C@@H]1CSCN1C(=O)OCC1c2ccccc2-c2ccccc21]

However, in one embodiment, this compound is specifically excluded from the scope of Formula (i).

Polymorphs, pseudomorphs, salts, including pharmaceutically acceptable salts, solvates, and derivatives of these compounds are also within the scope of the invention.

In one embodiment, the compounds described above are kinase inhibitors, and, ideally, are inhibitors of a Syk kinase. However, in some embodiments, the compounds have pro-motor/agonist activity.

A second aspect of the invention comprises a pharmaceutical composition comprising at least one compound of the first aspect of the invention, and at least one of a pharmaceutically acceptable carrier, a diluent and an excipient.

A third aspect of the invention comprises a method of inhibiting a Syk kinase, comprising the step of contacting a Syk kinase or an active fragment thereof with an effective amount of a compound of the first aspect of the invention.

A fourth aspect of the invention comprises a method of inhibiting a Syk kinase in an animal, comprising the step of administering to the animal an amount of a compound of the first aspect of the invention effective to inhibit a Syk kinase.

A fifth aspect of the invention comprises a method of inhibiting an SH2-mediated signal transduction in a mammal in need thereof, which comprises administering to the mammal a compound of the first aspect of the invention in an amount effective to inhibit the SH2-mediated signal transduction.

A sixth aspect of the invention comprises a method of treating a patient who has a proliferative disease, restenosis, osteoporosis, inflammation, allergic reaction, or cardiovascular disease, the method comprising administering to the patient a therapeutically effective amount of a composition of the second aspect of the invention.

A seventh aspect of the invention comprises a method of treating a patient who has a cancer, the method comprising administering to the patient a therapeutically effective amount of a composition of the second aspect of the invention.

An eighth aspect of the invention comprises a method for inducing immunosuppression in a patient, the method comprising administering to the patient an amount of a composition of the second aspect of the invention sufficient to cause immunosuppression.

A ninth aspect of the invention comprises a method of inhibiting a protein kinase comprising contacting a protein kinase with an amount of a compound according to the first aspect of the invention effective to inhibit an activity of the protein kinase.

A tenth aspect of the invention comprises a method of treating, inhibiting, or preventing a kinase-mediated disease, comprising administering to a subject an amount of a compound of the first aspect of the invention effective to treat, inhibit or prevent the kinase mediated disease.

An eleventh aspect of the invention comprises a method of inhibiting FcR or integrin mediated respiratory burst, degranulation or phagocytosis in a cell, said method comprising contacting the cell with an amount of a compound of the first aspect of the invention effective to inhibit FcR or integrin mediated respiratory burst, degranulation or phagocytosis in the cell.

A twelfth aspect of the invention comprises a method of inhibiting IgG-induced or IgE-induced degranulation of a cell, comprising contacting a cell capable of undergoing IgG-induced or IgE-induced degranulation with an amount of a compound of the first aspect of the invention effective to inhibit IgG-induced or IgE-induced degranulation of the cell.

A thirteenth aspect of the invention comprises a method of inhibiting IgG-induced or IgE-induced mast or basophil cell degranulation in an animal, comprising administering to the animal an amount of a compound of the first aspect of the invention effective to inhibit IgG-induced or IgE-induced mast or basophil cell degranulation.

BRIEF DESCRIPTION OF THE DRAWINGS

The invention will be described in conjunction with the following drawings, wherein.

DETAILED DESCRIPTION

Definitions

Figure 1:
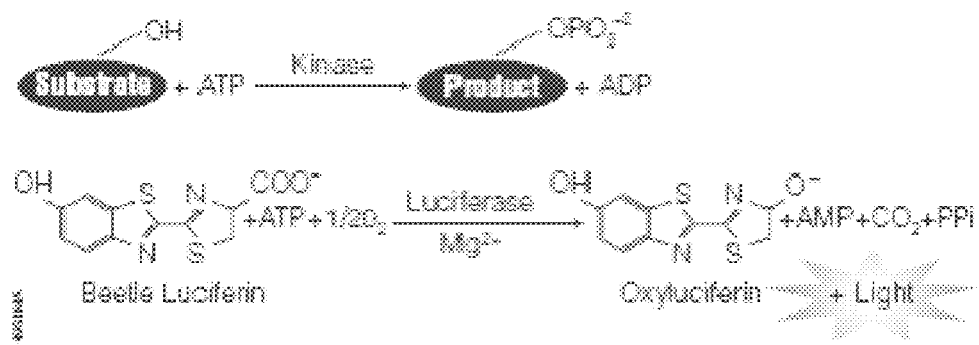
FIG. 1 is a schematic depiction of an assay used to detect activity.

"Kinase-mediated process" or "Kinase-mediated disease or disorder" refers to a cellular process, disease or disorder in which a kinase plays a role. In some embodiments, the kinase is a JAK kinase. The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., 1996, Mol. Cell. Biol. 16:4710-6; Jurlander et al., 1997, Blood. 89:4146-52; Kaneko et al., 1997, Clin. Exp. Immun. 109:185-193; and Nakamura et al., 1996, J. Biol. Chem. 271:19483-8). They are also known to be important to lymphocyte differentiation, function and survival. JAK-3 in particular plays an essential role in the function of lymphocytes, macrophages, and mast cells. Nonlimiting examples of JAK kinase mediated diseases that may be treated or prevented with the compounds, include, but are not limited to allergies, asthma, autoimmune diseases such as transplant rejection (e.g., kidney, heart, lung, liver, pancreas, skin; host versus graft reaction (HVGR), etc), rheumatoid arthritis, and amyotrophic lateral sclerosis, T-cell medicated autoimmune diseases such as multiple sclerosis, psoriasis and Sjogren's syndrome, Type II inflammatory diseases such as vascular inflammation (including vasculitis, arteritis, atherosclerosis and coronary artery disease), diseases of the central nervous system such as stroke, pulmonary diseases such as bronchitis obliteraus and primary pulmonary hypertension, and solid, delayed type IV hypersensitivity reactions, and hematologic malignancies such as leukemia and lymphomas.

"Therapeutically effective amount" refers to an amount of a compound sufficient to treat a specified disorder or disease by partially or completely alleviating at least one of its symptoms.

"Prophylactically effective amount" refers to an amount of a compound sufficient to prevent or delay the development of a specified disorder or disease. Typically, subjects in which prophylaxis is practiced are not suffering from the specified disorder or disease, but are recognized as being at an elevated risk for developing this disease or disorder based on factors such as, but not limited to, diagnostic markers and family history.

"Syk Kinase" refers to the 72 kDa non-receptor (cytoplasmic) spleen protein tyrosine kinase expressed in hematopoetic cells as well as fibroblasts, epithelial cells, breast tissue, hepatocytes, neuronal cells and vascular endothelial cells (Yanagi, et al, 2001, 288(3); 495-498). Syk kinase includes two consensus Src-homology 2 (SH2) domains in tandem that bind to phosphorylated immunoreceptor tyrosine-based activation motifs ("ITAMs"), a "linker" domain and a catalytic domain (for a review of the structure and function of Syk kinase see Sada et al., 2001, J. Biochem. (Tokyo) 130:177-186); see also Turner et al., 2000, Immunology Today 21:148-154). Syk kinase has been extensively studied as an effector of B-cell receptor (BCR) signaling (Turner et al., 2000, supra). Syk kinase is also critical for tyrosine phosphorylation of multiple proteins that regulate important pathways leading from immunoreceptors, such as $Ca^{2+}$ mobilization and mitogen-activated protein kinase (MAPK) cascades and degranulation. Syk kinase also plays a critical role in integrin signaling in neutrophils (see, e.g., Mocsai et al. 2002, Immunity 16:547558).

As used herein, Syk kinase includes kinases from any species of animal, including but not limited to, *homo sapiens*, simian, bovine, porcine, rodent, etc., recognized as belonging to the Syk family. Specifically included are isoforms, splice variants, allelic variants, mutants, both naturally occurring and man-made. The amino acid sequences of such Syk kinases are well known and available from GENBANK. Specific examples of mRNAs encoding different isoforms of human Syk kinase can be found at GENBANK Accession No.: gi|21361552|ref|NM-003177.2|; gi|496899|emb|Z29630.1|HSSYKPTK[496899]; and gi|15030258|gb|BC011399.1|BC011399[15030258], which are incorporated herein by reference.

Skilled artisans will appreciate that tyrosine kinases belonging to other families may have active sites or binding pockets that are similar in three-dimensional structure to that of Syk. As a consequence of this structural similarity, such kinases, referred to herein as "Syk mimics," are expected to catalyze phosphorylation of substrates phosphorylated by Syk. Thus, it will be appreciated that such Syk mimics, signal transduction cascades in which such Syk mimics play a role, and biological responses effected by such Syk mimics and Syk mimic-dependent signaling cascades may be regulated, and in particular inhibited, with many of the prodrugs described herein.

"Syk-Dependent Signaling Cascade" refers to a signal transduction cascade in which Syk kinase plays a role. Nonlimiting examples of such Syk-dependent signaling cascades include the FcαRI, FcεRI, FcγRI, FcγRIII, BCR, TCR and integrin signaling cascades.

"Autoimmune Disease" refers to those diseases which are commonly associated with the non-anaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

"Inflammatory Disease" refers to those diseases which are associated with acute or chronic inflammatory reaction as a response to an endogenous or exogenous stimulus, irrespective of the nature of the stimulus (antigen, hapten, etc). Non-limiting examples of inflammatory disease include asthma, systemic lupus erythematosis, rheumatoid arthritis, gouty arthritis, and the systemic vasculitides.

"Pro-drug" refers to a derivative of an active compound (drug) that may require a transformation under the conditions of use, such as within the body, to release the active drug. Pro-drugs are frequently, but not necessarily, pharmacologically inactive until converted into the active drug. Pro-drugs are typically obtained by masking a functional group in the drug compound believed to be in part required for activity with a pro-group (defined below) to form a pro-moiety which undergoes a transformation, such as cleavage, under the specified conditions of use to release the functional group, and hence the active drug. The cleavage of the pro-moiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the pro-drug is administered or the acidic conditions of the stomach, or it may be supplied exogenously.

A wide variety of pro-groups, as well as the resultant pro-moieties, suitable for masking functional groups in the active stereoisomerically enriched compounds described herein to yield pro-drugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide pro-moiety, which may be hydrolyzed in vivo to provide the carboxyl group. Other specific examples of suitable pro-groups and their respective pro-moieties will be apparent to those of skill in the art.

"Pro-group" refers to a type of protecting group that, when used to mask a functional group within an active stereoisomerically enriched drug compound to form a pro-moiety, converts the drug into a pro-drug. Pro-groups are typically attached to the functional group of the drug via bonds that are cleavable under specified conditions of use. Thus, a pro-group is that portion of a pro-moiety that cleaves to release the functional group under the specified conditions of use. As a specific example, an amide pro-moiety of the formula —NH—C(O)CH3 comprises the pro-group —C(O)CH3.

The Compounds

A first aspect of the invention encompasses compounds that have useful biological activities, including the ability to modulate, for example, to inhibit, a variety of protein kinases, for example, SYK kinase, in vitro and/or in vivo. The compounds of the invention are grouped into the nine different classes (classes a-i, with individual compounds 1-9 falling within classes a-i) described below.

wherein:

$R_1$ and $R_2$ are independently selected from the group consisting of —C(O)OR$_5$, —C(S)OR$_5$, —C(NR$_5$)OR$_5$, —C(O)SR$_5$, —C(S)SR$_5$, —C(NR$_5$)SR$_5$, —C(O)N(R$_5$)$_2$, —C(S)N(R$_5$)$_2$, —C(NR$_5$)N(R$_5$)$_2$, —N(R$_5$)C(O)OR$_5$, —N(R$_5$)C(S)OR$_5$, —N(R$_5$)C(NR$_5$)OR$_5$, —N(R$_5$)C(O)SR$_5$, —N(R$_5$)C(S)SR$_5$, —N(R$_5$)C(NR$_5$)SR$_5$, —N(R$_5$)C(O)N(R$_5$)$_2$, —N(R$_5$)C(S)N(R$_5$)$_2$, —N(R$_5$)C(NR$_5$)N(R$_5$)$_2$, —NO$_2$, —SOR$_5$, —SO$_2$R$_5$; —SO$_3$R$_5$; —CN, —PO$_4$R$_5$, —C(O)R$_5$, —C(S)R$_5$, and —C(NR$_5$)R$_5$, $R_3$ is selected from the group consisting of —C$_{1-6}$ perfluoroalkyl, such as trifluoromethyl and pentafluoroethyl, —C$_{1-6}$ haloalkyl, —C$_{1-6}$ alkyl, and $R_4$ is selected from the group consisting of halo, such as fluoro, chloro, bromo, and iodo; nitro; cyano; carbonyls, including —C(O)OR$_5$, —C(O)R$_5$, —C(O)N(R$_5$)$_2$, and —C(O)SR$_5$; —SOR$_5$; —SO$_2$R$_5$; —SO$_3$R$_5$; and —PO$_4$R$_5$, and in one embodiment is halo, such as bromo;

$R_5$ is a substituent selected from the group consisting of H, —C$_{1-6}$ alkyl, —C$_{1-6}$ alkylaryl, -aryl-C$_{1-6}$ alkyl, —C$_{1-6}$ alkylheteroaryl, -heteroaryl-C$_{1-6}$alkyl, -aryl, and -heteroaryl.

Z is selected from the group consisting of C$_{1-6}$ alkyl, alkenyl, heterocyclyl, aryl, heteroaryl, halo, —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)O R", —SO$_2$R', —SO$_2$NR'R", and —NR'SO$_2$R", where R' and R" are individually hydrogen, C$_{1-6}$ alkyl, cycloalkyl, heterocyclyl, aryl, or arylalkyl, wherein the aryl or heteroaryl rings can be substituted at any free position with Z, j is an integer from 0 to the number of available positions on the aryl or heteroaryl ring to which the Z substituent is attached, X is, individually, N, or C bonded to H or a substituent Z, and, in one embodiment, no more than two X are N within any ring structure, and Y is O, S, or NR$_5$.

In one embodiment, R$_5$ is H.

In one embodiment, all X are carbon bonded to H or a substituent Z. In one aspect of this embodiment, all X are C—H.

In one embodiment, the compound of Formula (a) has the structure:

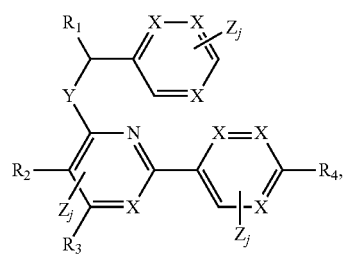

(a)

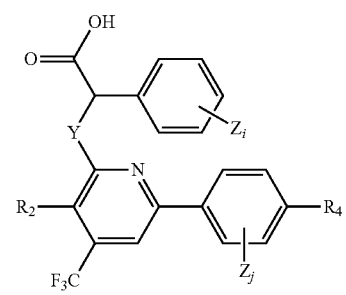

In one embodiment, the compound of Formula (a) has the structure:

Compound 1

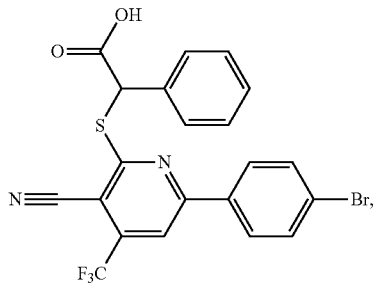

and in another embodiment, this structure is specifically excluded from the compounds of Formula (a).

Compounds of Formula (b) generally have the formula:

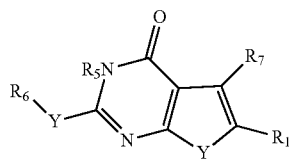

or the isomeric form:

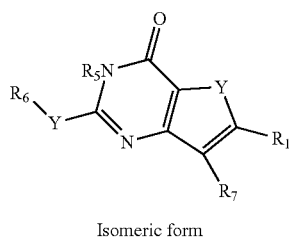

Isomeric form wherein:

Y, $R_1$ and $R_5$ are as defined above with respect to Formula (a), $R_6$ is $C_{1-6}$-alkylaryl, $C_{1-6}$-alkylheteroaryl, aryl, or heteroaryl, wherein the aryl or heteroaryl ring in the aryl, aralkyl, alkheteroaryl, or heteroaryl substituents is optionally substituted with one to three substituents, Z, as described above, wherein in one embodiment, the substituent, Z, is a substituent defined as $R_2$ herein, and in another embodiment, is defined as being selected from the group consisting of C(S)OR$_5$, —C(NR$_5$)OR$_5$, —C(O)SR$_5$, —C(S)SR$_5$, —C(NR$_5$)SR$_5$, —C(O)N(R$_5$)$_2$, —C(S)N(R$_5$)$_2$, —C(NR$_5$)N(R$_5$)$_2$, —N(R$_5$)C(O)OR$_5$, —N(R$_5$)C(S)OR$_5$, —N(R$_5$)C(NR$_5$)OR$_5$, —N(R$_5$)C(O)SR$_5$, —N(R$_5$)C(S)SR$_5$, —N(R$_5$)C(NR$_5$)SR$_5$, —N(R$_5$)C(O)N(R$_5$)$_2$, —N(R$_5$)C(S)N(R$_5$)$_2$, —N(R$_5$)C(NR$_5$)N(R$_5$)$_2$, —SOR$_5$, —SO$_2$R$_5$, —SO$_3$R$_5$, —PO$_4$R$_5$, —C(O)R$_5$, —C(S)R$_5$, and —C(NR$_5$)R$_5$, $R_7$ is a substituent selected from the group consisting of H, —$C_{1-6}$ alkyl, such as methyl, —$C_{1-6}$ alkylaryl, -aryl-$C_{1-6}$ alkyl, —$C_{1-6}$ alkylheteroaryl, -heteroaryl-$C_{1-6}$alkyl, -aryl, and -heteroaryl.

In one embodiment, $R_5$ is H.

In one embodiment, $R_6$ is $C_{1-6}$-alkylaryl or $C_{1-6}$-alkylheteroaryl.

In one embodiment, the compound of Formula (b) has the structure:

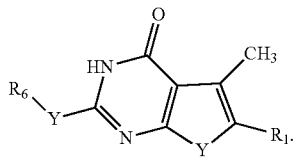

In another embodiment, the compound of Formula (b) has the structure:

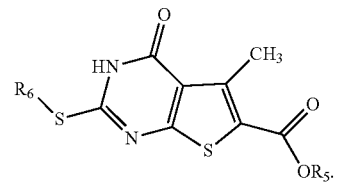

In still another embodiment, the compound of Formula (b) has the structure:

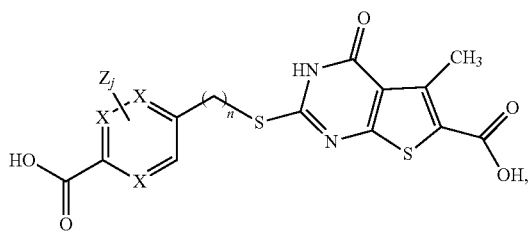

wherein Z, X, and j are as defined above with respect to Formula (a), preferably, no more than two X are N within any ring structure, and n is an integer of from 1 to 3.

In still another embodiment, the compound of Formula (b) has the structure:

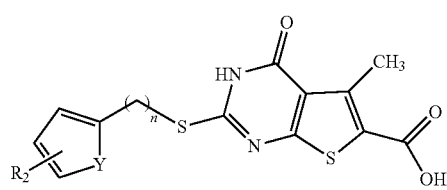

A specific compound within the scope of Formula (b) is as follows:

Compound 2

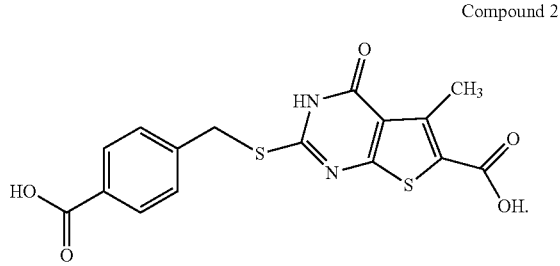 [SMILES: Cc1c(C(=O)O)sc2nc(SCc3ccc(C(=O)O)cc3)[nH]c(=O)c12]

In one embodiment, this compound is specifically excluded from the scope of Formula (b).

Compounds of Formula (c) have the general formula

Formula (c)

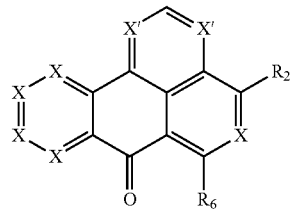

wherein:

X' is N or C bonded to H or a substituent, Z, and at least one X' is N;

X, Z, j, and $R_6$ are as previously defined, no more than three X, and preferably, no more than two X, are N within any ring structure, and $R_8$ is selected from the group consisting of $OR_5$, $SR_5$, and $N(R_5)_2$.

In one embodiment, the compounds of Formula (c) have the formula:

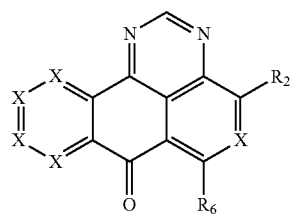

wherein X, Z, j, and $R_2$ are as previously defined, no more than three X, and preferably, no more than two X, are N within any ring structure, and $R_8$ is selected from the group consisting of $OR_5$, $SR_5$, and $N(R_5)_2$.

In one embodiment, the compounds of Formula (c) have the formula:

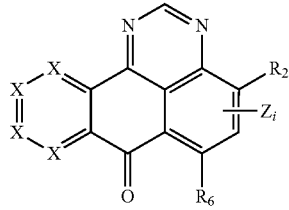

In one embodiment, the compounds of Formula (c) have one of the following formulas:

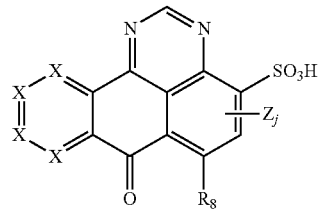

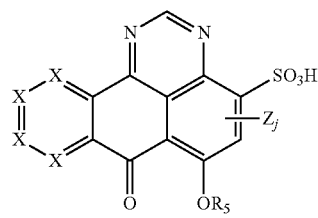

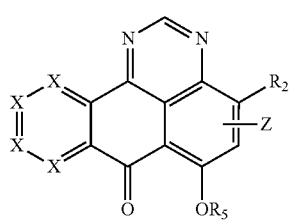

where Z, j, X, and $R_5$ are as previously defined, and no more than three X, and preferably, no more than two X, are N within any ring structure.

A specific compound within the scope of Formula (c) is

Compound 3

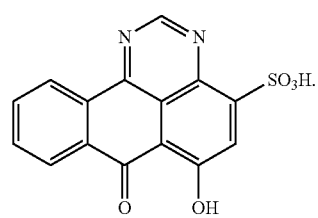

However, in one embodiment, this compound is specifically excluded from the scope of Formula (c).

The compounds of Formula (d) generally have the formula:

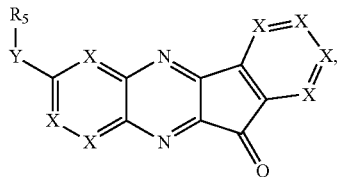

wherein X, Y, and R₅, are as defined above, and no more than three X, in one embodiment, no more than two X, and in another embodiment, zero or one X, are N within any ring structure.

In one embodiment, the compounds have the formula:

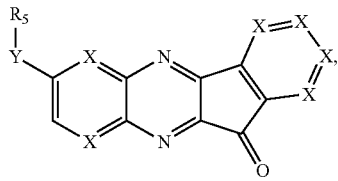

wherein R⁵ and X are as defined above, and no more than three X, and preferably, no more than two X, are N within any ring structure.

The compounds of Formula (d) can fall within the following sub-formulas:

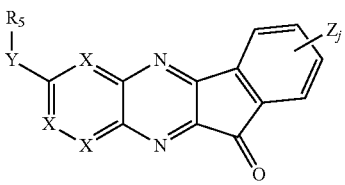

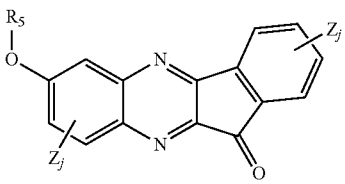

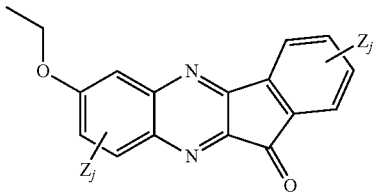

as well as positional isomers thereof, wherein Z, j, X, Y, and R₅ are as defined above, and preferably, no more than two X are N within any ring structure.

In one embodiment, the compound of Formula (d) has the formula:

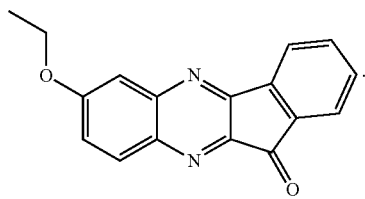

Compound 4

However, in one embodiment, this compound is specifically excluded from the scope of Formula (d).

The compounds of Formula (e) generally have the formula:

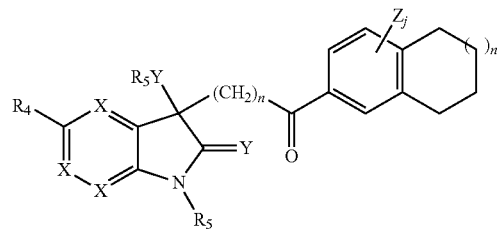

wherein X, Y, Z, j, R₄, R₅, and n are as defined above.

In one embodiment, the compounds have the formula:

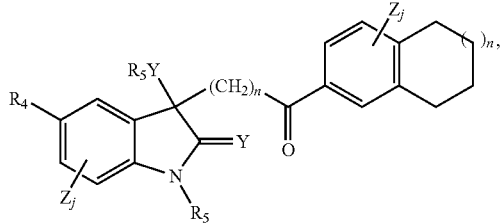

wherein Y, Z, j, R₄, R₅, and n are as defined above.

The compounds of Formula (e) can fall within the following sub-formulas:

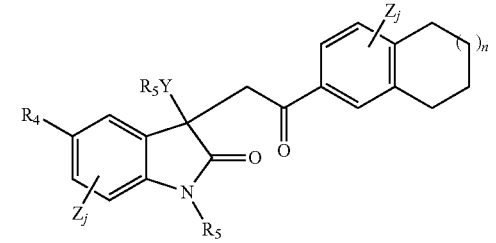

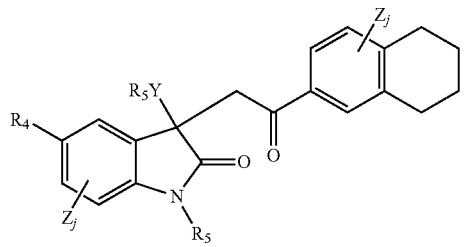

-continued

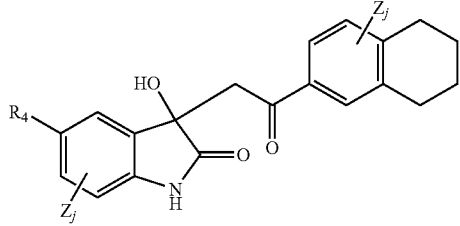

wherein Y, Z, j, R$_4$, R$_5$, and n are as defined above.

More specifically, the compounds of Formula (e) can have the following formulas:

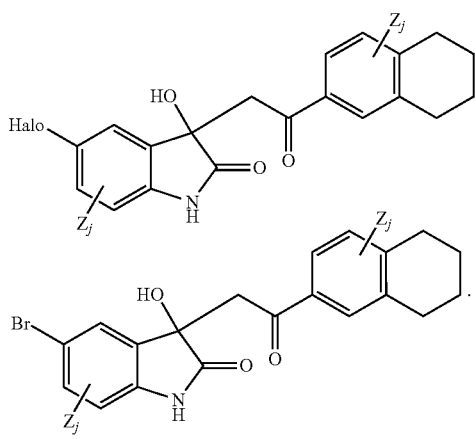

A specific compound falling within the scope of Formula (e) has the following formula:

Compound 5

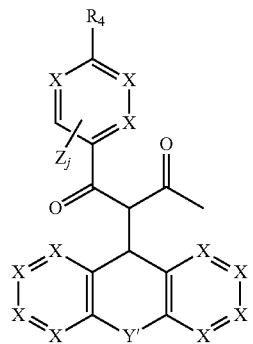

However, in one embodiment, this compound is specifically excluded from the scope of Formula (e).

The compounds of Formula (f) generally have the formula:

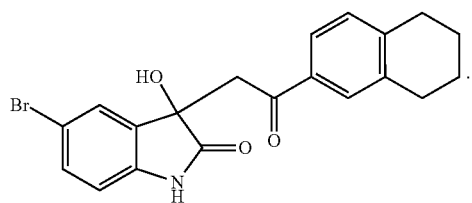

wherein X, Z, j, and R$_4$ are as defined above, Y' is O, S, NR$_5$, —CH$_2$O, —CH$_2$S, or —CH$_2$NR$_5$, and no more than three X, and preferably, no more than two X, are N within any ring structure.

Specific compounds within the scope of Formula (f) include the following:

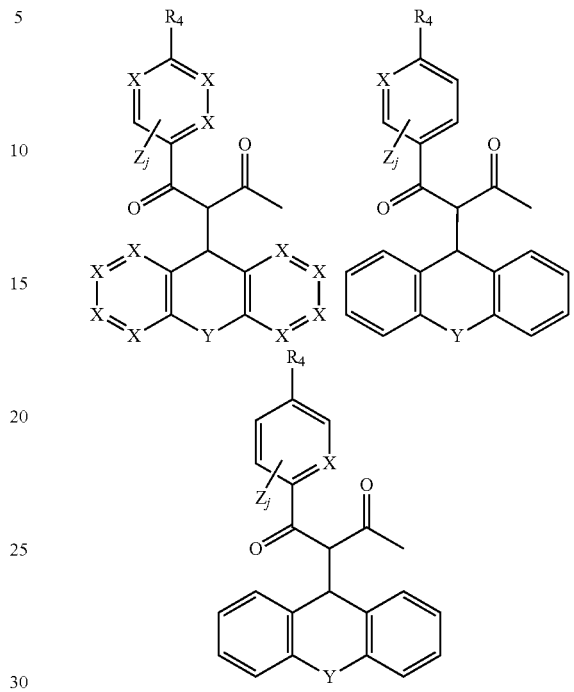

wherein X, Y, Z, j, and R$_4$ are as defined above, and no more than three X, and preferably, no more than two X, are N within any ring structure.

Further compounds within the scope of Formula (f) include the following:

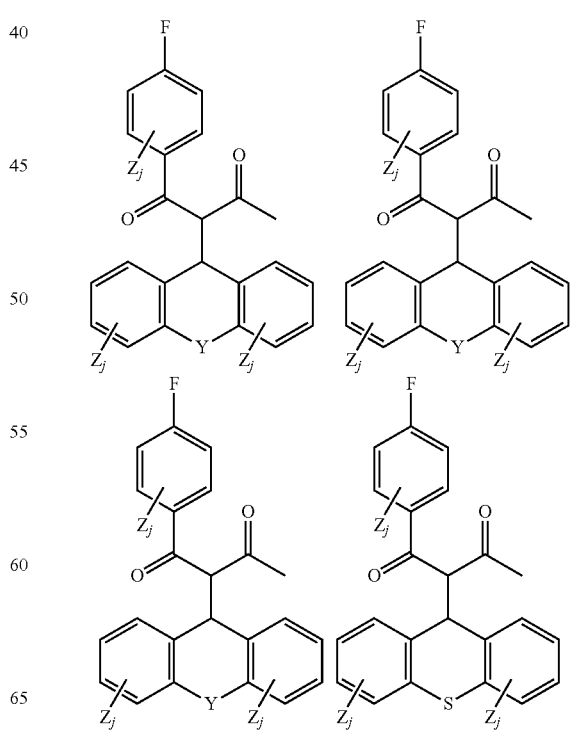

The compounds of Formula (g) generally have the formula:

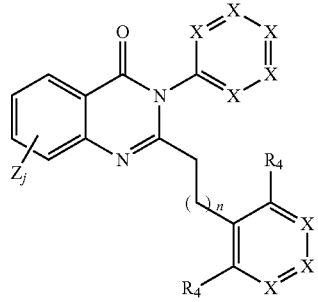

wherein X, Y, Z, j, n, and $R_4$ are as defined above, and no more than three X, and preferably, no more than two X, are N within any ring structure.

Specific compounds within Formula (g) include the following:

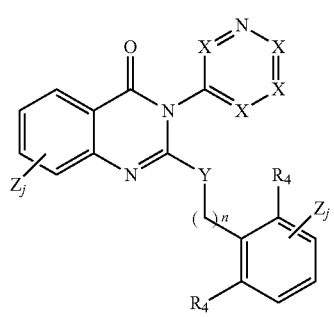

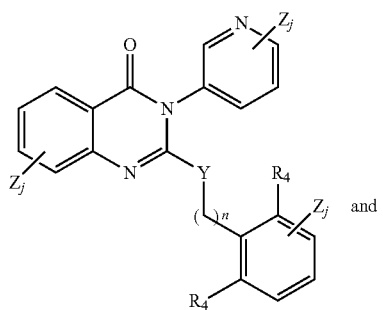

and

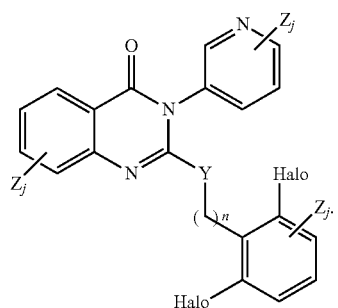

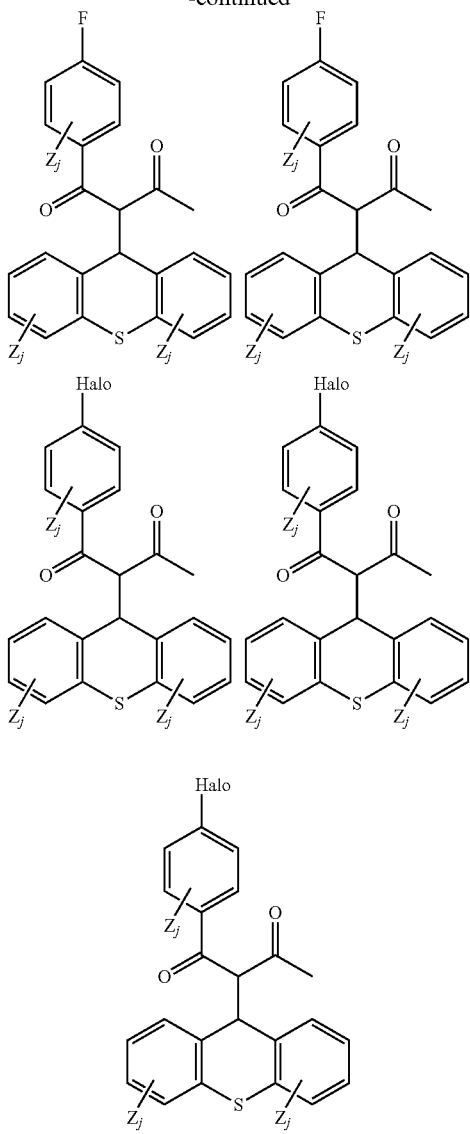

wherein Y, Z, and j are as defined above.

A specific compound within the scope of Formula (f) is:

Compound 6

However, in one embodiment, this compound is specifically excluded from the scope of Formula (f).

Specific compounds within Formula (g) also include the following:

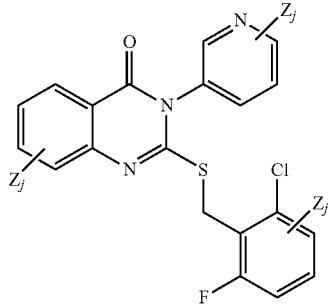

wherein Z and j are as defined above.

A specific compound within Formula (g) is as follows:

Compound 7

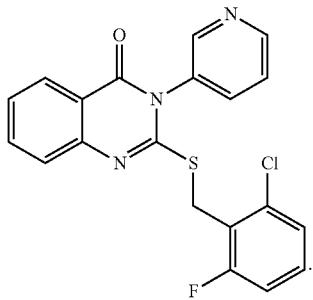

However, in one embodiment, this compound is specifically excluded from the scope of Formula (g).

The compounds of Formula (h) generally have the following formula:

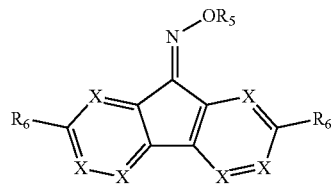

wherein X, $R_5$, and $R_6$ are as defined above, and, in one embodiment, no more than two X are N within any ring structure, and in another embodiment, no more than one X is N within any ring structure.

In one embodiment, where X is C bound to H or a substituent, Z, Z is selected from the group consisting of $C_{1-6}$ alkyl, alkenyl, heterocyclyl, aryl, heteroaryl, halo, —OR', —NR'R", —CF$_3$, —CN, —C$_2$R', —SR', —N$_3$, —NR'C(=O)R", —C(=O)R', —OC(=O)R', —OC(=O)NR'R", —NR'C(=O)O R", —SO$_2$R', —SO$_2$NR'R", and —NR'SO$_2$R", where R' and R" are individually hydrogen, $C_{1-6}$ alkyl, cycloalkyl, heterocyclyl, aryl, or arylalkyl, wherein the aryl or heteroaryl rings can be substituted at any free position with Z, More specifically, the compounds of Formula (h) can have the following structure:

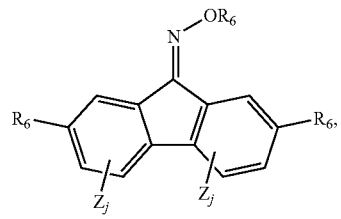

wherein Z, j, $R_5$, and $R_6$ are as defined above.

Still more specifically, the compounds of Formula (h) can have the following structure:

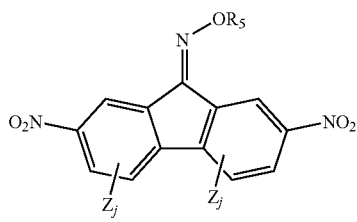

wherein Z, j, and $R_5$ are as defined above.

A specific compound within the Formula (h) has the formula:

Compound 8

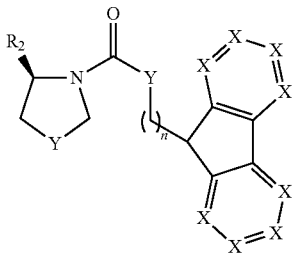

However, in one embodiment, this compound is specifically excluded from the scope of Formula (h).

The compounds of Formula (i) have the following general formula:

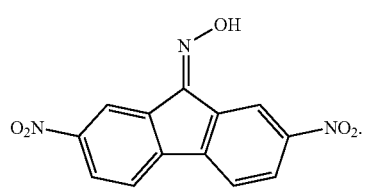

wherein X, Y, n, and $R_2$ are as defined above, and no more than 3 X, and preferably, no more than two X, are N within any ring structure.

In one embodiment, $R_2$ is selected from the group consisting of C(S)OR$_5$, —C(NR$_5$)OR$_5$, —C(O)SR$_5$, —C(S)SR$_5$, —C(NR$_5$)SR$_5$, —C(S)N(R$_5$)$_2$, —C(NR$_5$)N(R$_5$)$_2$, —N(R$_5$)C(O)OR$_5$, —N(R$_5$)C(S)OR$_5$, —N(R$_5$)C(NR$_5$)OR$_5$, —N(R$_5$)C(O)SR$_5$, —N(R$_5$)C(S)SR$_5$, —N(R$_5$)C(NR$_5$)SR$_5$, —N(R$_5$)C(O)N(R$_5$)$_2$, —N(R$_5$)C(S)N(R$_5$)$_2$, —N(R$_5$)C(NR$_5$)N(R$_5$)$_2$, —NO$_2$, —SOR$_5$, —SO$_2$R$_5$, —SO$_3$R$_5$, —CN, —PO$_4$R$_5$, —C(O)R$_5$, —C(S)R$_5$, and —C(NR$_5$)R$_5$, More specific compounds within Formula (i) fall within the following formulas:

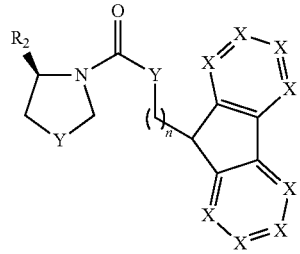

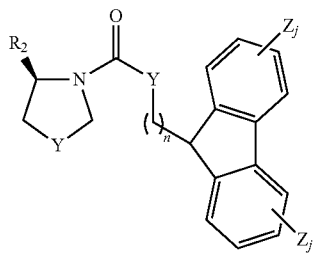

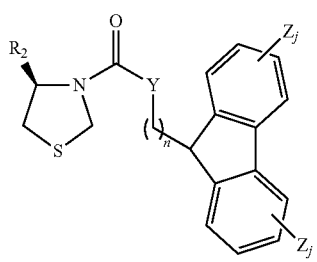

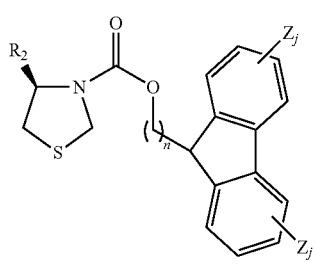

wherein Z, j, X, Y, n, and $R_6$ are as defined above, and no more than 3X, in one embodiment, no more than two X, and in another embodiment, no more than zero or one X, are N within any ring structure.

Additional compounds within the scope of Formula (i) include the following:

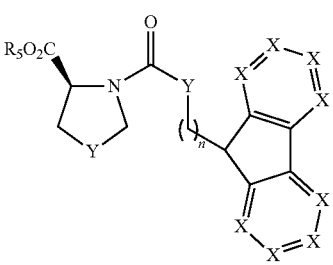

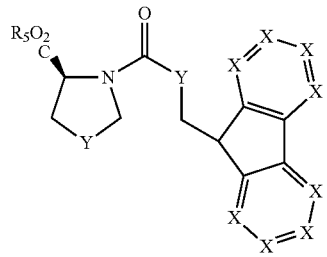

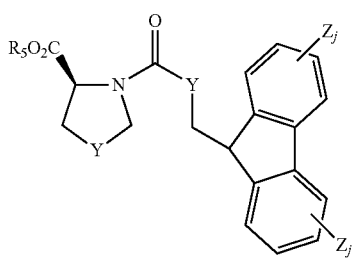

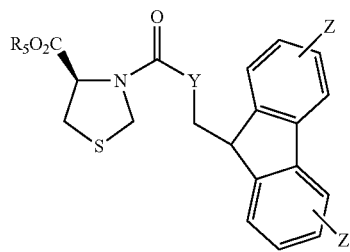

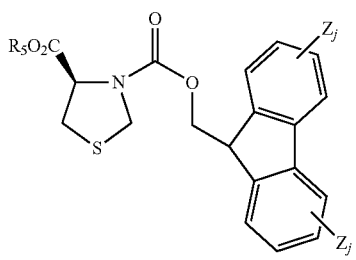

wherein Z, j, X, Y, and n are as defined above, and no more than 3X, and preferably, no more than two X, are N within any ring structure.

Still more specific compounds falling within the scope of Formula (i) include the following:

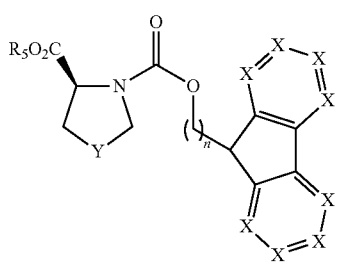

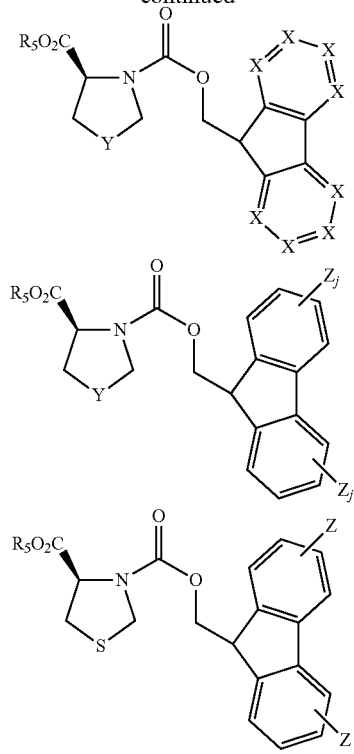

wherein Z, j, X, Y, and n are as defined above, and no more than 3X, and preferably, no more than two X, are N within any ring structure.

A specific compound falling within the scope of Formula (i) is the following:

Compound 9

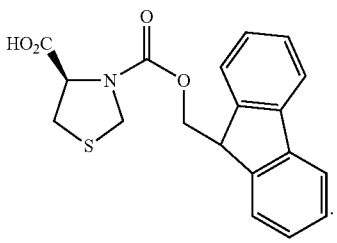

However, in one embodiment, this compound is specifically excluded from the scope of Formula (i).

Polymorphs, pseudomorphs, salts, including pharmaceutically acceptable salts, solvates, and derivatives of these compounds are also within the scope of the invention.

In one embodiment, the compounds described above are kinase inhibitors, and, ideally, are inhibitors of a Syk kinase. In some embodiments, the compounds are kinase promotors/agonists.

Compound Synthesis

The synthesis of compounds of Formulas a-i, including compounds 1-9, is discussed below.

Compound 1 is α-[[6-(4-bromophenyl)-3-cyano-4-(trifluoromethyl)-2-pyridinyl]thio]-benzeneacetic acid, having the CAS Reg. No. 625369-82-6, and the structure shown below.

Compound 1

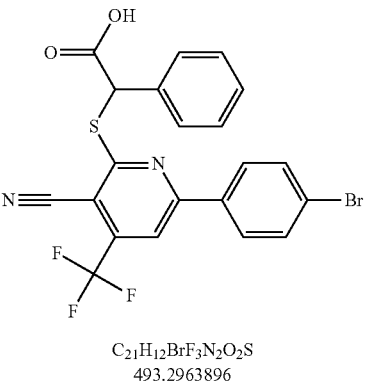

$C_{21}H_{12}BrF_3N_2O_2S$
493.2963896

Rodinovskaya et al., "One-Pot Synthesis of Diverse 4-Di(tri)fluoromethyl-3-cyanopyridine-2(1H)-thiones and Their Utilities in the Cascade Synthesis of Annulated Heterocycles." J. Comb. Chem, 2008, 10, (2), pp 313-322 discloses a method for synthesizing Compound 1 and structural analogs thereof, such as the compounds of Formula a).

The chemistry involves the initial Claisen condensation between corresponding methyl(methylene)ketone 1 and ethyl difluoro(trifluoro)acetate 2a,b conducted in ether in the presence of sodium ethoxide to produce corresponding sodium salt 3; then, after evaporation of ether, the reaction mixture is reacted with cyanothioacetamide at 50-60° C. in ethanol, quenched with acetic acid, and refluxed for a short period of time to produce the final pyridine compound, which Rodinovskaya teaches as precipitating at 5-10° C. within several hours (Scheme 1). The yields of prepared 4-di(tri)fluoromethyl-3-cyanopyridine-2(1H)-thiones 6 vary from 50% to 98% and strongly depend on other substituents present in the pyridine ring.

Scheme 1.
Synthesis of 4-Di(tri)fluoromethyl-3-cyanopyridine-2(1H)-thiones

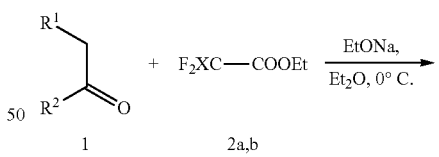

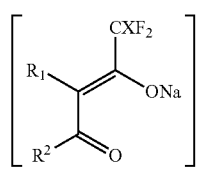

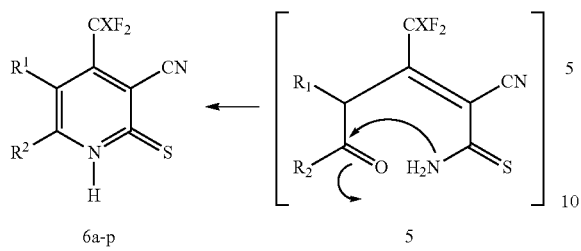

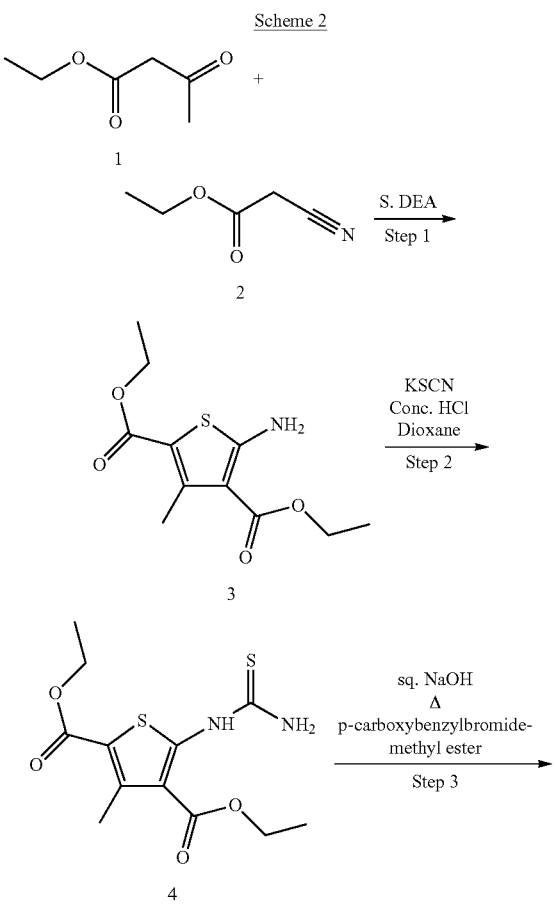

Rodinovskaya demonstrated that a variety of aromatic groups can be produced at position $R_2$ (which corresponds to the position in the compounds described herein which includes the aryl/heteroaryl ring substituted with $R_4$). The aromatic rings were substituted with one or more halogens, alkyl groups, alkoxy groups, and the like, without adversely affecting the coupling chemistry. Rodinovskaya also demonstrated that the chemistry also works with a variety of heteroaryl rings, including those in which $R_2$ (as shown in Scheme 1, not as this term is used to define the compounds described herein) is 3- or 4-pyridinyl. Aromatic and heteroaromatic rings with a —C(O)—CH$_2$R$_1$ functional group (where $R_1$ is as shown in Scheme 1, not as used to define the compounds described herein), or those with a —C(S) or —C(NR$_5$) in place of the —C(O) moiety, are readily available or can be prepared using no more than routine experimentation.

WO 2007124545 A1 discloses the preparation of structural analogs of Compound 1 for use as integrase inhibitors, including (3-cyano-6-phenyl-4-trifluoromethylpyridin-2-yl-sulfanyl)-phenyl-acetic acid (a.k.a. α[[3-cyano-6-phenyl-4-(trifluoromethyl)-2-pyridinyl]thio]-benzeneacetic acid) at page 46, which differs from Compound 1 only in the absence of a bromine substituent on the 6-phenyl group.

Compounds of Formula b), Including Compound 2 and Structural Analogs Thereof

Compound 2 is 1,4-dihydro-2-[[[4-(methoxycarbonyl)phenyl]methyl]thio]-5-methyl-4-oxo-thieno-[2,3-d]pyrimidine-6-carboxylic acid, having the CAS Reg. No. 831177-52-7 and the structure shown below.

Structure

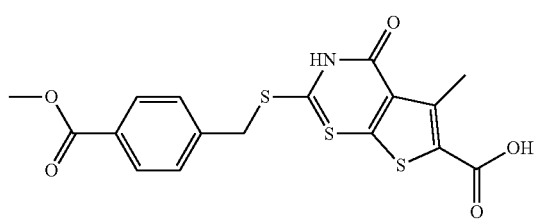

Formula C$_{17}$H$_{14}$N$_2$O$_5$S$_2$
Molweight 390.43346

The compounds of Formula b), such as Compound 2, can be synthesized in accordance with the reaction shown in Scheme 2.

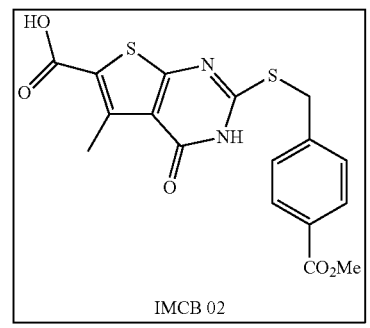

Where it is desired to provide functionalization on the benzene ring to which the carboxymethyl group is attached, one can use a benzylbromide with different functionality. So long as the functionality on the benzene ring is not affected by the nucleophilic displacement reaction in Step 3, or such functionality is suitably protected, one can introduce a variety of substituents on the moiety. Suitably functionalized benzylbromides (or other benzyl halides, tosylates, brosylates, nosylates, acetates, and the like) are well known to those of skill in the art, or can be readily prepared using no more than routine experimentation.

In those embodiments in which one wishes to replace the S in the thioether moiety with an O, the amine group in precursor 3 can be reacted with a cyanate to form a compound similar to precursor 3, but with a furan rather than a thiophene ring. Similarly, the amine can be reacted with a cyanamide, such as hydrogen cyanamide or alkyl, aryl, arylalkyl, or alkylaryl cyanamides to replace the thiophene ring with a pyrrole ring.

In those embodiments in which one wishes to replace the —CH₂— moiety in the S—CH₂, O—CH₂ or NHR₅—CH₂ group with a longer alkyl chain, an appropriate alkyl halide or (aryl)-alkyhalide other than benzylbromide can be used.

WO2008045406 discloses structural analogs of Compound 2 having the Formula (I):

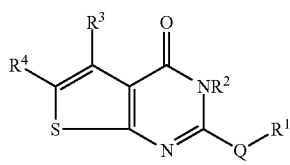

where Q=—S—, —S(O)—, and —S(O)₂—; R1=C1-C9 alkyl, C2-C9 alkyenyl, C2-C9 alkynyl, C6-C12 aryl, and C1-C12 carbonyl; R2=C1-C9 alkaryl, and C6-C12 aryl; and R3 and R4 are independently C1-C9 alkyl, C2-C9 alkenyl, C2-C9 alkynyl, C1-C9 alkyloxy, and C1-C12 carbonyl, or R3 and R4, combined, form an C3-C9 carbocyclic, C2-C9 heterocyclic, C6-C12 aryl, or C2-C12 heteroaryl, ring system), pharmaceutical compounds, methods of synthesis, and methods for treating diseases and conditions associated with cellular necrosis.

Ivachtchenko et al., "Synthesis of Substituted Thienopyrimidine-4-ones" J. Combinatorial Chem. (2004), 6(4), 573-583, discloses methods for synthesizing structural analogs of Compound 2. The synthesis is outlined in Scheme 3, below:

Scheme 3: Preparation of Substituted 2-Thioxo-2,3-dihydrothieno[3,2-d]pyrimidin-4(3H)-ones and 2,3-Dihydrothieno[3,2-d]pyrimidin-4(3H)-on-2-thiols

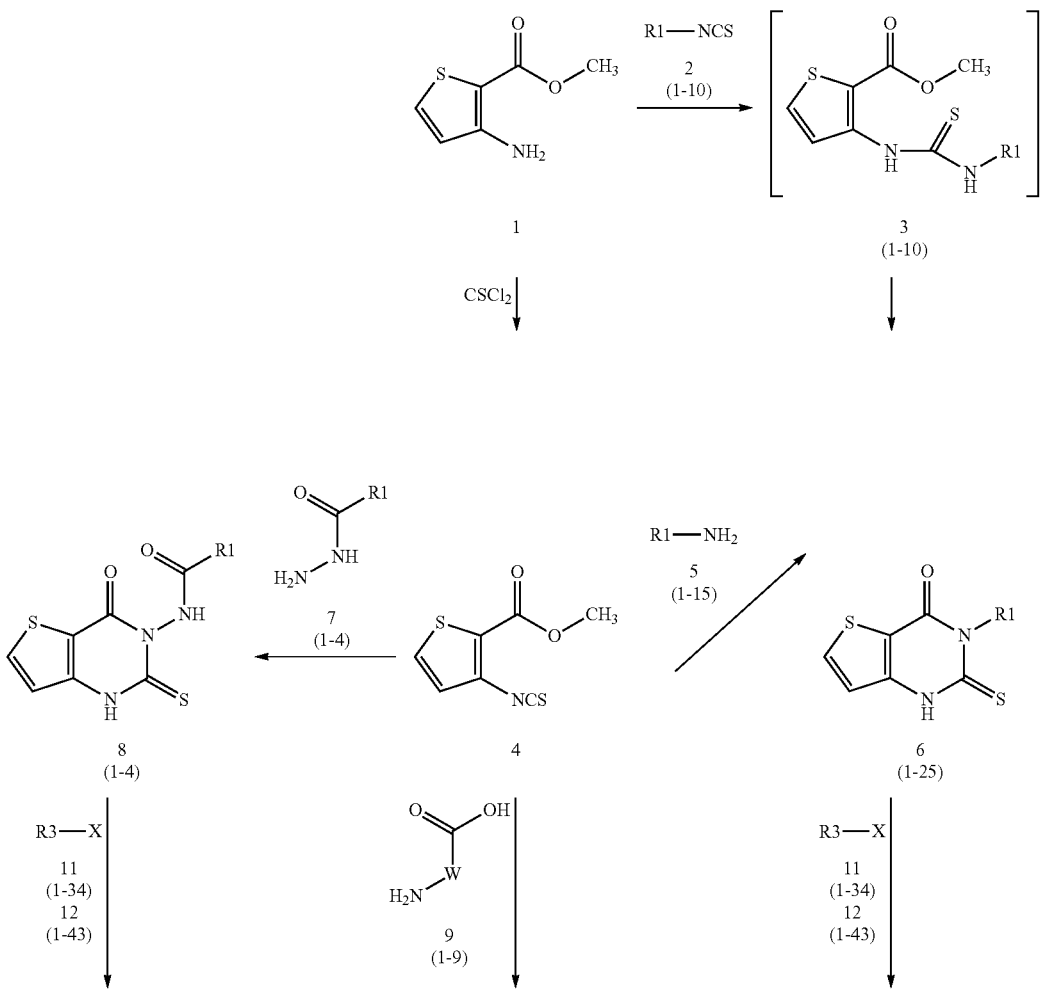

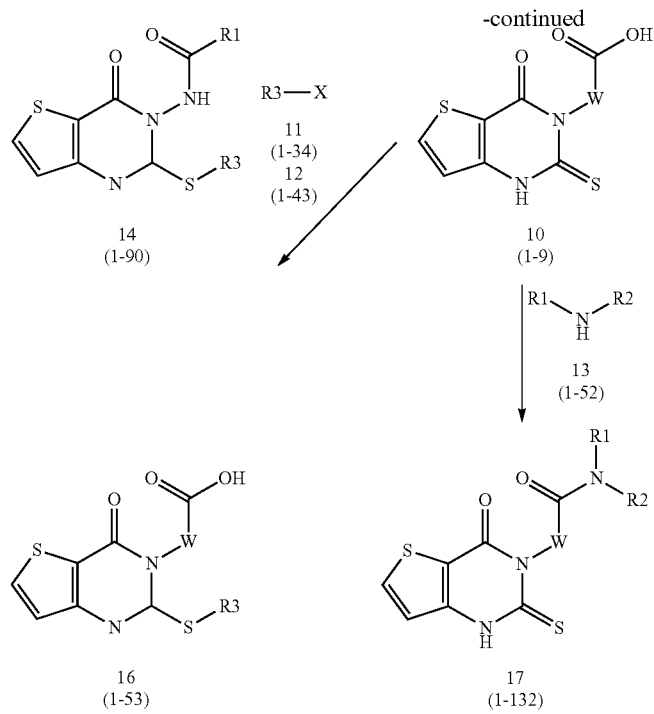
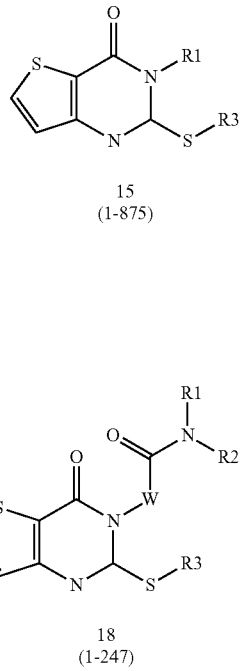

Ivachtchenko used a variety of different phenyl isocyanates to convert starting material 1 to intermediate 3, and amines to convert starting material 1 to intermediate 4. Representative $R_1$ groups in the phenyl isocyanates included 2-methylphenyl, 2-methoxycarbonylphenyl, 3-fluorophenyl, 4-ethylphenyl, 4-ethoxyphenyl, 2,3-dimethylphenyl, 3,4-dimethylphenyl, 3,4-dichlorophenyl, 3-fluoro-4-methylphenyl, and 4-ethoxycarbonylphenyl. Accordingly, since the chemistry worked with a variety of electron donating and electron withdrawing groups present on the phenyl ring, the chemistry is broadly applicable to preparing a number of phenyl thioureas.

Ivachtchenko also reacted the amine group on compound 1 with $C(S)Cl_2$ to produce an isocyanate moiety directly on the thiophene ring, which was then reacted with a variety of amines, including ethyl, 1-butyl, 2-butyl, 3-isopropyloxypropyl, furfuryl, benzyl, 4-methylbenzyl, 4-methoxybenzyl, 4-fluorobenzyl, 3,4-dimethoxybenzyl, 1,3-benzodioxol-5-ylmethyl, 2-(1-pyrrolidinyl)ethyl, 3-cyclohexylpropyl, 3-(1-piperidinyl)propyl, and 3-[4-(4-methoxyphenyl)piperazine-1-yl]propyl. Thus, the chemistry is broadly applicable to producing a number of substituted thioureas.

The thienylthioureas (compound 3 in Scheme 3) were cyclized in situ to give the corresponding 3-substituted thieno[3,2-d]pyrimidin-4(3H)-one-2-thiones (compound 6 in Scheme 3). However, the phenylisocyanates are apparently easier to cyclize than the alkyl isocyanates. An alternative route, namely, reaction of intermediate 4 with acyl hydrazides (compound 7 in Scheme 3) was used to perform efficient cyclization to the thieno[3,2-d]pyrimidin-4(3H)-one-2-thiones (compound 8 in Scheme 3) in triethylamine and 2-propanol at reflux. The acyl hydrazides mentioned were various phenyl or substituted phenyl hydrazides, though the chemistry can also be performed with other alkyl or unsubstituted hydrazides.

Compounds of the structure of compound 10 can be prepared by reacting compounds of the structure of compound 4 with any of a variety of amino acids, including amino acids in which W in compound 9 is alkyl, cycloalkyl-alkyl, aryl, arylalkyl, or alkylaryl.

A variety of alkylating agents (alkyl halides and alpha-chloroketones), as well as amines, were then used to convert the-substituted thieno[3,2-d]pyrimidin-4(3H)-one-2-thiones (compounds 6 or 8) to compounds 15 or 14, respectively.

The chemistry in Ivachtchenko can be modified such that appropriately functionalized thiophene starting materials are used, i.e., thiophenes with groups $R_1$ and $R_7$ attached, protected forms of these groups attached, or groups that are synthons for these groups attached. Where $R_1$ or $R_7$ are a carboxylic acid, a protecting group can be present during the various coupling steps, and removed after the coupling is completed.

Although all of the compounds in Ivachtchenko include an alkyl or alkaryl substituent on the pyrimidine nitrogen, the strategy can be used to prepare compounds with an NH moiety at that position as well.

Synthesis of Compounds of Formula c), Including Compound 3 and Structural Analogs Thereof Compound 3 is 6-hydroxy-7-oxo-7H-benzo[e]perimidine-4-sulfonic acid, having the CAS Reg. No. 293326-43-9 and the structure shown below.

Structure

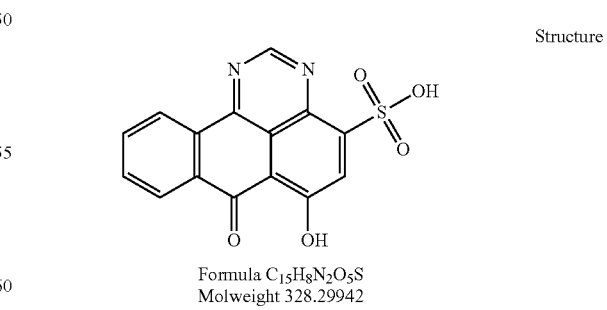

Formula $C_{15}H_8N_2O_5S$
Molweight 328.29942

De Leon et al., "An In Vitro Screen of Bacterial Lipopolysaccharide Biosynthetic Enzymes Identifies an Inhibitor of ADP-Heptose Biosynthesis," Chem & Biol (2006), 13(4), 437-441, discloses 6-hydroxy-7H-benzo[e]pyrimidin-7-one, a structural analog of Compound 3.

PL 180370 and U.S. Pat. Nos. 2,032,772 and 3,862,944 disclose the structurally related class of compounds known as hydroxyanthrapyrimidines and methods of synthesizing them.

U.S. Pat. No. 3,862,944 discloses preparing these compounds by reacting a compound of formula:

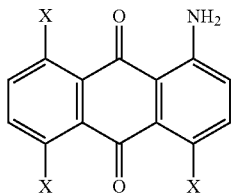

with an N,N-dialkylformamide halide at a temperature from 20-100° C. In the '944 patent, The X in the structure shown above is OH or phenylamino, and the other positions on the phenyl can be replaced by a variety of substituents, such as chlorine bromine, trifluoromethyl, nitro, methyl, ethyl, methoxy, ethoxy, sulfonamide, carbamoyl, or alkoxycarbonyl where the alkyl group has from 2-5 carbon atoms. As the chemistry is amenable to a wide variety of substitution on the various aromatic rings, the synthesis is quite general and can be broadly applied to prepare compounds in which the aryl rings can be functionalized with a variety of substituents, Z, as defined herein, or with groups that can be converted, as described herein, to such substituents.

Synthesis of Compounds of Formula d), Including Compound 4 and Structural Analogs Thereof Compound 4 is 7-ethoxy-11H-indeno[1,2-b]quinoxalin-11-one, having the CAS Reg. No. 328977-60-2 and the structure shown below.

Structure

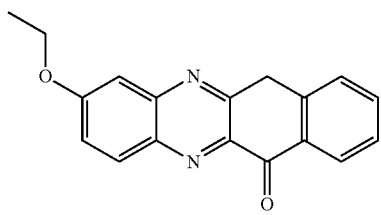

Formula C$_{17}$H$_{12}$N$_2$O$_2$
Molweight 276.28938

U.S. Pat. No. 5,789,427 to Chen et al. discloses structurally analogous compounds, 11H-Indeno[1,2-b]quinoxalin-11-ones, useful as tyrosine kinase inhibitors. No mention of the effect of these compounds on syk was noted.

The compounds can be prepared by reacting a suitably functionalized benzene-1,2-diamine with a suitably functionalized ninhydrin, as shown below:

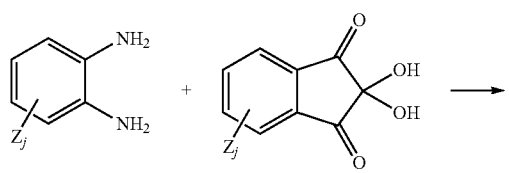

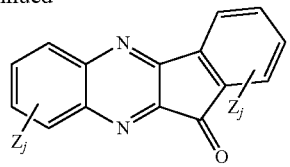

where Z and j are as defined above. Any substituents that would interfere with the coupling chemistry should be protected. Alternatively, at the time the coupling takes place, the aromatic rings can include synthons that can later be converted to the desired substituents. Synthons are well known to those of skill in the art, and are described, for example, in "Umpoled Synthons: A survey of sources and uses in synthesis," Tapio Hase, ed., John Wiley and Sons, NY (1987), the contents of which are hereby incorporated by reference in their entirety.

Synthesis of Compounds of Formula e), Including Compound 5 and Structural Analogs Thereof Compound 5 is 5-bromo-1,3-dihydro-3-hydroxy-3-[2-oxo-2-(5,6,7,8-tetrahydro-2-naphthalenyl)ethyl]-2H-indol-2-one, having the CAS Reg. No. 362506-63-6 and the structure shown below.

Structure

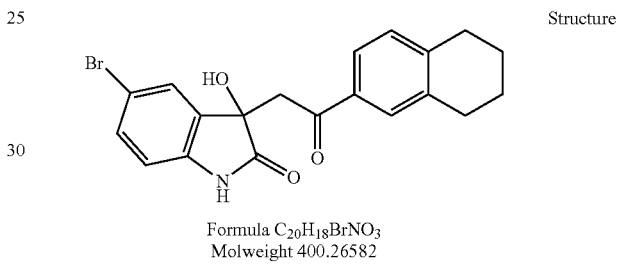

Formula C$_{20}$H$_{18}$BrNO$_3$
Molweight 400.26582

The compounds of Formula e) can be prepared, for example, by reacting a compound of formula:

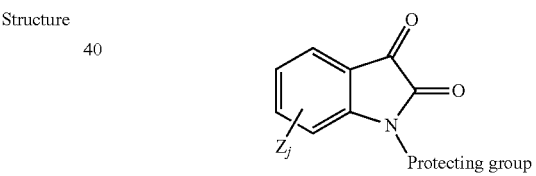

with a compound of the formula:

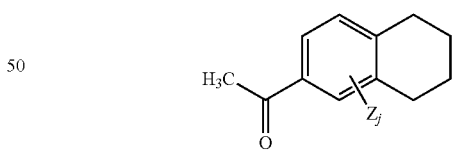

under conditions in which the enolate ion of the methyl ketone reacts with the carbonyl attached to the benzene (rather than the carbonyl in the lactam moiety). As with the other syntheses described herein, any substituents that would interfere with the coupling chemistry should be protected. Alternatively, at the time the coupling takes place, the aromatic rings can include synthons that can later be converted to the desired substituents.

Synthesis of Compounds of Formula f), Including Compound 6 and Structural Analogs Thereof Compound 6 is 1-(4-fluorophenyl)-2-(9H-thioxanthen-9-yl)-1,3-butanedione, having the CAS Reg. No. 433697-23-5 and the structure shown below.

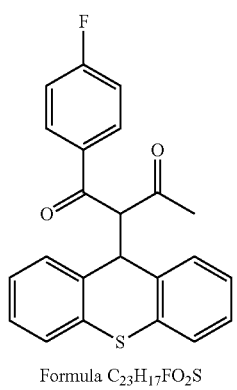

Formula C₂₃H₁₇FO₂S
Molweight 376.4432832

Sawicki et al., "Reaction of thiaxanthydrol with compounds containing active hydrogen." Journal of Organic Chemistry (1956), 21, 183-9 discloses structural analogs of Compound 6 and methods for preparing them. The synthesis generally involves the following reaction:

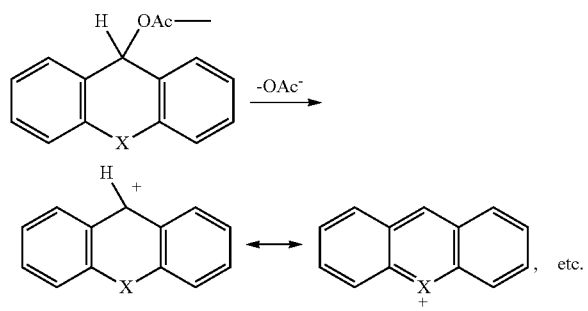

X = O or S

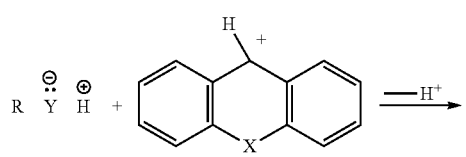

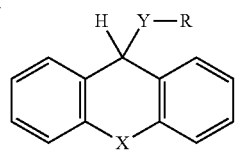

Y = C, N, or S

The starting material is formed by reacting xanthydrol or thiaxanthydrol with acetic acid to form the acetate. As the acetate group leaves, the carbonium ion that results is attracted to the hydrogen-substituted carbon, nitrogen, or sulfur atom of high electron density in the donor molecule (depicted above as RYH). The active hydrogen is "split off" to form acetic acid, and yield the final product. As shown in Table III of Sawicki, donor atoms include diketones of the formula RC(O)—CYH—C(O)R', including one in which R is $C_6H_5$, and R' is $CH_3$, which, when the starting material is thiaxanthydrol, yields the structure of compound 6. Either of the phenyl groups in the xanthydrol or thiaxanthydrol can be substituted with substituents, Z, as defined herein, and the substitution will increase or decrease the rate of reaction, depending on whether the substituents are electron donating or electron withdrawing, but the chemistry will proceed to products in any case.

The coupling chemistry described above will similarly work if the phenyl ring (R) in RC(O)—CYH—C(O)R' is substituted, though any acidic hydrogens might be suitably protected so as to avoid interference with the acidic proton Y in the coupling chemistry, and deprotected after the desired coupling chemistry is completed. Protecting groups are well known to those of skill in the art, and are described, for example, in Greene and Wuts, Protective Groups in Organic Synthesis, Third Edition, John Wiley and Sons (1999), the contents of which are hereby incorporated by reference.

The coupling chemistry described above will similarly work if one or both of the phenyl rings in xanthydrol or thiaxanthydrol is replaced with a nitrogen-containing heteroaryl ring, such as a pyridine, pyrimidine, pyrazine, or triazine ring.

The preparation of pyridine/pyrimidine/pyrazine variants of thiaxanthydrol and xanthydrol can be readily accomplished by those of skill in the art.

Pyridines are susceptible to nucleophilic attack at C-2, as this leads to anionic intermediates which possess a favorable resonance form with the negative charge located on nitrogen. 2-halopyridines will undergo preferential substitution of the halide by a two step addition-elimination reaction.

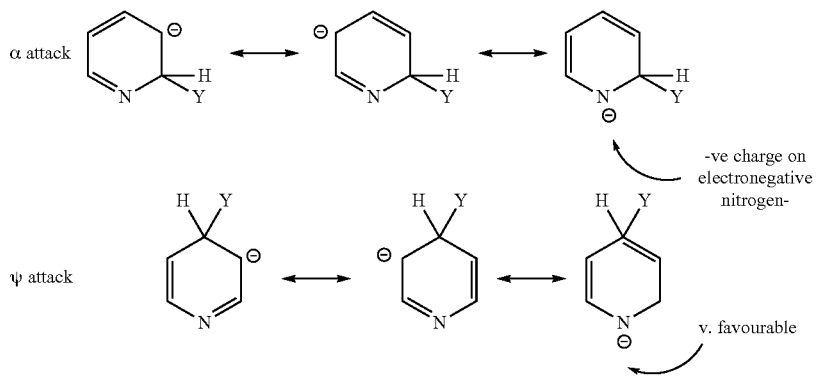

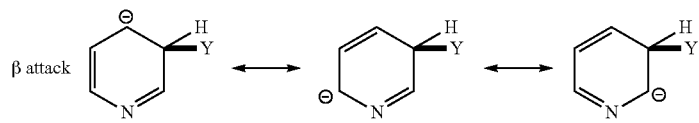

Certain nucleophiles, including $NH_2^-$, alkyl and aryl anions, will add, almost invariably, at C-2, to form the dihydropyridine anion. This anion undergoes subsequent oxidation to form the 2-substituted pyridine. In the case of $NH_2^-$ the reaction is known as the Chichibabin reaction.

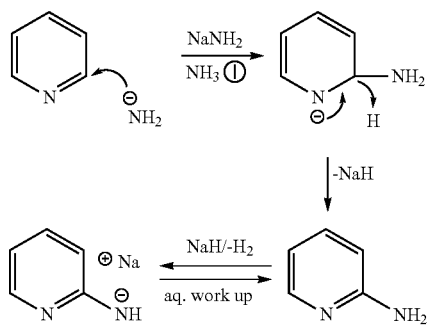

In contrast to nucleophilic substitution, electrophiles react preferentially with the lone pair of the nitrogen to generate a pyridinium ion which, being positively charged, is unreactive towards electrophilic substitution. Neutral pyridine, which can react with electrophiles, is present only in a very low equilibrium concentration, so the reaction rate tends to be somewhat slow.

Electrophilic substitution forms 3-substituted products, predominantly, much in the same way that a nitro substituent directs electrophilic substitution of benzene to the meta position. Electron donating substituents at positions 2, 4 and 6 favor reaction.

Thus, one can prepare nitrogen analogs of the xanthydrol and thiaxanthydrol starting materials using a combination of electrophilic and nucleophilic chemistry, with appropriate starting materials. For example, a benzyl bromide with a protected OH, SH, or $NH_2$ group at the ortho position can be converted to an organolithium reagent, and reacted with pyridine, and the OH, SH, or $NH_2$ group deprotected. Subsequent electrophilic aromatic substitution of the pyridine ring with the OH, SH, or $NH_2$ group will provide the compound of interest. Alternatively, an aniline with an ortho $CH_2OH$ group can be deprotonated (two equivalents of base, one for the OH, and the other for the proton on the $NH_2$ group) and used in a nucleophilic attack on the pyridine (or pyrimidine or pyrazine). Then, the benzylic OH group can be reacted with acid to form a benzyl carbocation, which will then react with the pyridine in an electrophilic aromatic substitution reaction to yield the desired product (i.e., the pyridine, pyrimidine, or pyrazine analog of the xanthydrol starting material). Subsequent coupling chemistry, as described above, will yield the desired final product.

Synthesis of Compounds of Formula g), Including Compound 7 and Structural Analogs Thereof Compound 7 is 2-[[(2-chloro-6-fluorophenyl)methyl]thio]-3-(3-pyridinyl)-4(3H)-quinazolinone, having the CAS Reg. No. 215654-80-1 and the structure shown below.

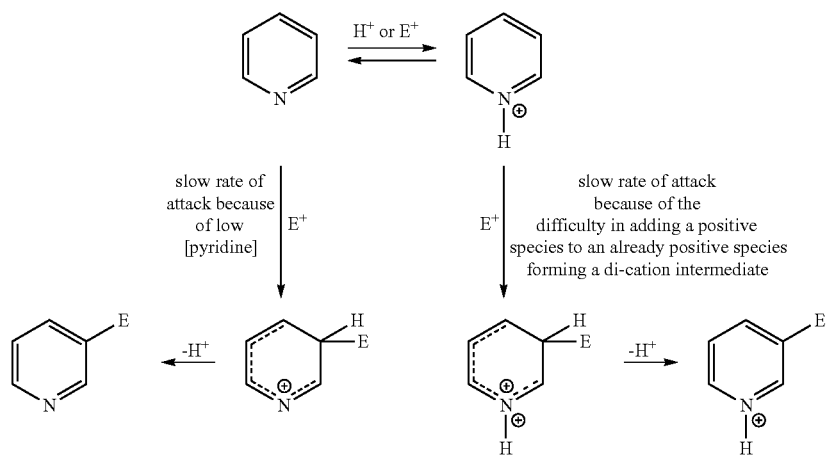

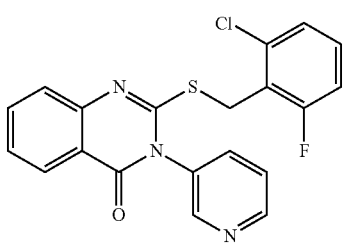

Formula $C_{20}H_{13}ClFN_3OS$
Molweight 397.8531232

A general synthesis of compounds of this formula, and analogs thereof, is shown below:

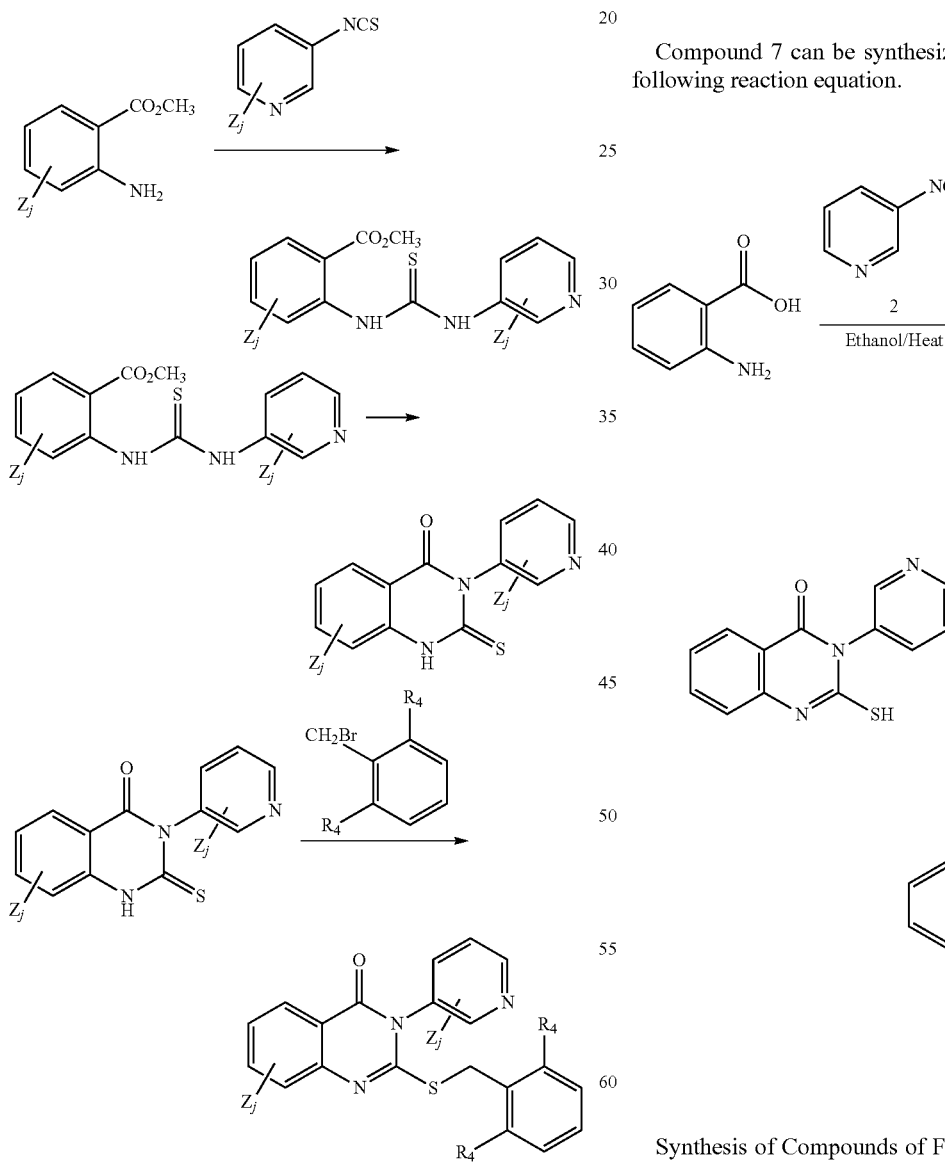

⊘ indicates text missing or illegible when filed in which the conditions for carrying out the cyclization of the thiourea intermediate are substantially the same as those used in the cyclization chemistry in Scheme 3. The chemistry is broadly applicable, and can provide aromatic rings with a variety of different substituents.

DD 255531 discloses structural analogs said to be useful as vasodilators and sedatives, including:

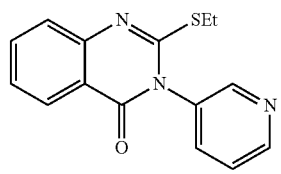

Compound 7 can be synthesized in accordance with the following reaction equation.

Synthesis of Compounds of Formula h), Including Compound 8 and Structural Analogs Thereof Compound 8 is 2,7-dinitro-oxime-9H-fluoren-9-one, having the CAS Reg. No 23818259 and the structure shown below.

Structure

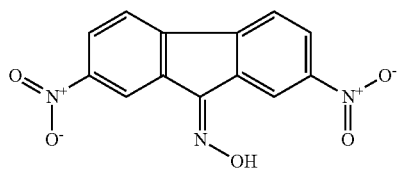

Formula C$_{13}$H$_7$N$_3$O$_5$
Molweight 285.21178

WO 2007016338 discloses Compound 8 as a Chk2 kinase inhibitor compound although it was not tested against Syk.

Compound 8 can be synthesized in accordance with the following reaction equation.

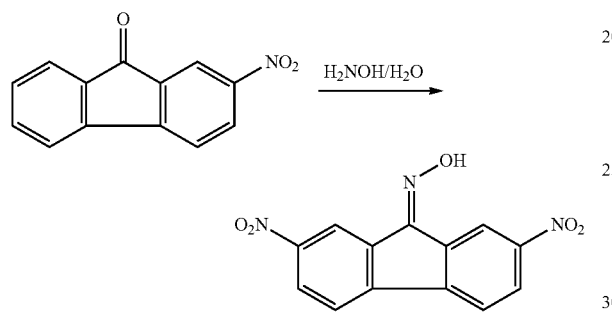

Other substituents, Z, can be present on the benzene rings, if desired. If such groups would interfere with the reaction of the benzophenone carbonyl with NH$_2$OH, then they can be suitably protected, and deprotected at the appropriate time. Alternatively, the groups can be added to the rings after such time as the nitration chemistry has been carried out. If other groups are present on the aromatic rings at positions that might otherwise be nitrated, the reaction of the benzophenone carbonyl with NH$_2$OH will occur, but further nitration of the aromatic ring will not occur at such positions.

Synthesis of Compounds of Formula i), Including Compound 9 and Structural Analogs Thereof Compound 9 is 3-(9H-fluoren-9-ylmethyl)ester-3,4-thiazolidinedicarboxylic acid, having the CAS Reg. No 423719-54-4 and the structure shown below.

Structure

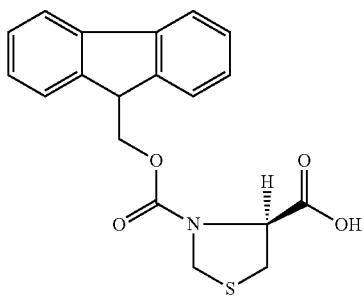

Formula C$_{19}$H$_{17}$NO$_4$S
Molweight 355.40758

WO 2002038591 discloses Compound 9 as a prodrug capable of being converted into a cytotoxic or cytostatic drug by fibroblast activation protein.

Compound 9 can be synthesized in accordance with the following reaction equation.

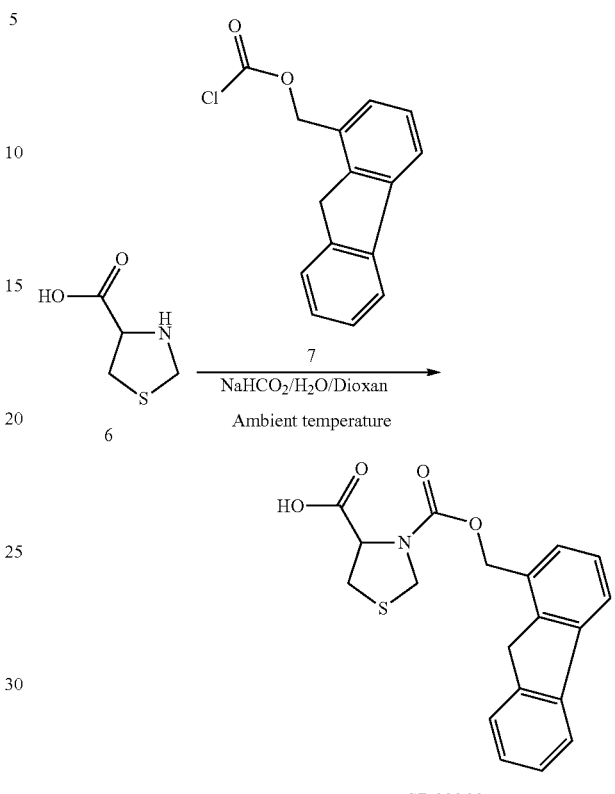

SB 02066

This chemistry is broadly applicable to form a variety of substituted aryl/heteroaryl rings. That is, substituent groups, Z, that do not interfere with the chloroformate (7) formation can be present on one or both of the aromatic rings in (7). Alternatively, if such substituent groups would interfere, they can be suitably protected. The carboxylic acid group in heterocycle (6) can be substituted with a number of other R$_6$ substituents, as defined herein, that do not interfere with the reaction of an amine with the chloroformate. Such substituted heterocycles are well known to those of skill in the art, or can be readily prepared using no more than routine experimentation.

Aryl and Heteroaryl Ring Moieties

Formulas a-i, as described above, can include aryl or heteroaryl rings. Representative aryl and heteroaryl rings that can be part of the compounds of Formulas a-i, as described herein, are provided below:

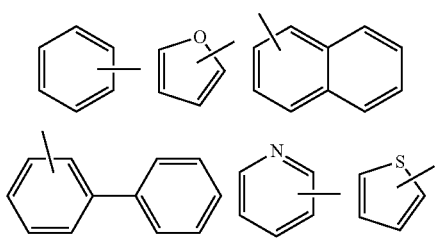

-continued

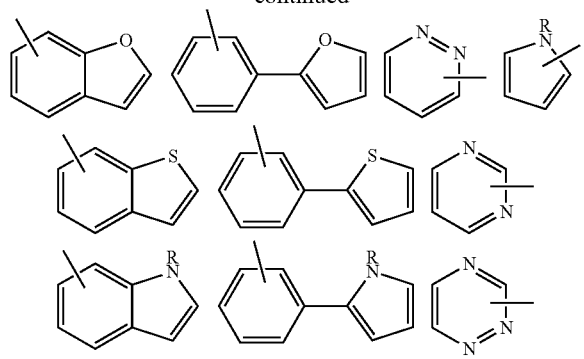

wherein any of the aryl/heteroaryl rings can be substituted with one or more substituents, Z, as described herein.

Functionalization of the Aryl and Heteroaryl Rings

The aryl and heteroaryl rings described herein, and used to prepare the compounds described herein, are either commercially available, or can be prepared from commercially available starting materials. Those that are not commercially available can be made by a variety of synthetic methodologies, related to the particular moieties and the particular substitution desired. The variation in synthetic methodology will be readily apparent to those of skill in the art of organic synthesis.

Those skilled in the art will readily understand that incorporation of substituents onto the aryl or heteroaryl rings can be readily realized, either before the core structures are prepared, or afterward (i.e., the substituents can be present during key coupling steps, or can be added after the unsubstituted compound has been prepared. Such substituents can provide useful properties in and of themselves, or serve as a handle for further synthetic elaboration. One proviso is that such substitution should either survive the synthesis conditions, or should be added after the synthesis is otherwise complete.

For example, aryl and heteroaryl rings can be halogenated using various known procedures, which vary depending on the particular halogen. Examples of suitable reagents include bromine/water in concentrated HBr, thionyl chloride, pyr-ICl, fluorine and Amberlyst-A. A number of other analogs, bearing substituents in a diazotized position of an aryl ring, can be synthesized from the corresponding aniline compounds, via the diazonium salt intermediate. The diazonium salt intermediates can be prepared using known chemistry, for example, treatment of aromatic amines such as aniline with sodium nitrite in the presence of a mineral acid.

Diazonium salts can be formed from anilines, which in turn can be prepared from nitrobenzenes (and analogous amine-substituted heteroaryl rings can be prepared from nitro-substituted heteroaryl rings). The nitro derivatives can be reduced to the amine compound by reaction with a nitrite salt, typically in the presence of an acid. Other substituted analogs can be produced from diazonium salt intermediates, including, but are not limited to, hydroxy, alkoxy, fluoro, chloro, iodo, cyano, and mercapto, using general techniques known to those of skill in the art. Likewise, alkoxy analogues can be made by reacting the diazonium salt with alcohols. The diazonium salt can also be used to synthesize cyano or halo compounds, as will be known to those skilled in the art. Mercapto substitutions can be obtained using techniques described in Hoffman et al., J. Med. Chem. 36: 953 (1993). The mercaptan so generated can, in turn, be converted to an alkylthio substituent by reaction with sodium hydride and an appropriate alkyl bromide. Subsequent oxidation would then provide a sulfone. Acylamido analogs of the aforementioned compounds can be prepared by reacting the corresponding amino compounds with an appropriate acid anhydride or acid chloride using techniques known to those skilled in the art of organic synthesis.

Hydroxy-substituted analogs can be used to prepare corresponding alkanoyloxy-substituted compounds by reaction with the appropriate acid, acid chloride, or acid anhydride. Likewise, the hydroxy compounds are precursors of both the aryloxy and heteroaryloxy via nucleophilic aromatic substitution at electron deficient aromatic rings. Such chemistry is well known to those skilled in the art of organic synthesis. Ether derivatives can also be prepared from the hydroxy compounds by alkylation with alkyl halides and a suitable base or via Mitsunobu chemistry, in which a trialkyl- or triarylphosphine and diethyl azodicarboxylate are typically used. See Hughes, Org. React. (N.Y.) 42: 335 (1992) and Hughes, Org. Prep. Proced. Int. 28: 127 (1996) for typical Mitsunobu conditions.

Cyano-substituted analogs can be hydrolyzed to afford the corresponding carboxamido-substituted compounds. Further hydrolysis results in formation of the corresponding carboxylic acid-substituted analogs. Reduction of the cyano-substituted analogs with lithium aluminum hydride yields the corresponding aminomethyl analogs. Acyl-substituted analogs can be prepared from corresponding carboxylic acid-substituted analogs by reaction with an appropriate alkyllithium using techniques known to those skilled in the art of organic synthesis.

Carboxylic acid-substituted analogs can be converted to the corresponding esters by reaction with an appropriate alcohol and acid catalyst. Compounds with an ester group can be reduced with sodium borohydride or lithium aluminum hydride to produce the corresponding hydroxymethyl-substituted analogs. These analogs in turn can be converted to compounds bearing an ether moiety by reaction with sodium hydride and an appropriate alkyl halide, using conventional techniques. Alternatively, the hydroxymethyl-substituted analogs can be reacted with tosyl chloride to provide the corresponding tosyloxymethyl analogs, which can be converted to the corresponding alkylaminoacyl analogs by sequential treatment with thionyl chloride and an appropriate alkylamine. Certain of these amides are known to readily undergo nucleophilic acyl substitution to produce ketones.

Hydroxy-substituted analogs can be used to prepare N-alkyl- or N-arylcarbamoyloxy-substituted compounds by reaction with N-alkyl- or N-arylisocyanates. Amino-substituted analogs can be used to prepare alkoxycarboxamido-substituted compounds and urea derivatives by reaction with alkyl chloroformate esters and N-alkyl- or N-arylisocyanates, respectively, using techniques known to those skilled in the art of organic synthesis.

Similarly, benzene rings (and pyridine, pyrimidine, pyrazine, and other heteroaryl rings) can be substituted using known chemistry, including the reactions discussed above. For example, the nitro group on nitrobenzene can be reacted with sodium nitrite to form the diazonium salt, and the diazonium salt manipulated as discussed above to form the various substituents on a benzene or heteroaryl ring.

Pharmaceutical Dosages and Administration

The compounds may be administered per se in the form of prodrugs or as pharmaceutical compositions, comprising an active compound or pro-drug. Pharmaceutical compositions comprising the active compounds (or prodrugs thereof) may be manufactured by means of conventional mixing, dissolving, granulating, dragee-making, levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically (see Remington's Pharmaceutical Sciences, 15th Ed., Hoover, J. E. ed., Mack Publishing Co. (2003).

The active compound or pro-drug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, intramuscular, transdermal, rectal, vaginal, etc., or a form suitable for administration by inhalation or insufflation.

For topical administration, the active compound(s) or pro-drug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampoules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, films or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate, lecithin). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, CREMOPHORE® or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or pro-drug, as is well known in the art.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or pro-drug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the active compound(s) or pro-drug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and U.S. Pat. No. 4,738,851.

For prolonged delivery, the active compound(s) or pro-drug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and U.S. Pat. No. 4,921,475.

Alternatively, other pharmaceutical delivery systems may be employed. Liposomes and emulsions are well-known examples of delivery vehicles that may be used to deliver active compound(s) or pro-drug(s). Certain organic solvents such as dimethylsulfoxide (DMSO) or other vehicles such as CREMOPHOR® (a class of non-ionic solubilizers and emulsifiers manufactured by BASF Corporation, Florham Park, N.J.), may also be employed, although usually at the cost of greater toxicity.

The pharmaceutical compositions may, if desired, be presented in a pack or dispenser device that may contain one or more unit dosage forms containing the active compound(s). The pack may, for example, comprise metal or plastic foil, such as a blister pack. The pack or dispenser device may be accompanied by instructions for administration.

Effective Dosages

The active compound(s) or pro-drug(s), or compositions thereof, will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. As another specific example, therapeutic benefit in the context of transplantation rejection includes the ability to alleviate an acute rejection episode, such as, for example, the HVGR (host versus graft response), or the ability to prolong the time period between onset of acute rejection episodes and/or onset of chronic rejection. Therapeutic benefit also includes halting or slowing the progression of the disease, regardless of whether improvement is realized.

For prophylactic administration, the compound may be administered to a patient at risk of developing one of the previously described conditions. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to induce one of the above-described maladies to prevent the onset of the disorder. For example, a compound may be administered to a healthy individual who is repeatedly exposed to an allergen known to induce allergies, such as latex, in an effort to prevent the individual from developing an allergy. Alternatively, a compound may be administered to a patient suffering from asthma prior to partaking in activities that trigger asthma attacks to lessen the severity of, or avoid altogether, an asthmatic episode.

In the context of transplant rejection, the compound may be administered while the patient is not having an acute rejection reaction to avoid the onset of rejection and/or prior to the appearance of clinical indications of chronic rejection.

The amount of compound administered will depend upon a variety of factors, including, for example, the particular indication being treated, the mode of administration, the severity of the indication being treated and the age and weight of the patient, the bioavailability of the particular active compound, etc. Determination of an effective dosage is well within the capabilities of those skilled in the art.

As known by those of skill in the art, the preferred dosage of the compounds will also depend on the age, weight, general health and severity of the condition of the individual being treated. Dosage may also need to be tailored to the sex of the individual and/or where administered by inhalation, the lung capacity of the individual. Dosage may also be tailored to individuals suffering from more than one condition or those individuals who have additional conditions which affect lung capacity and the ability to breathe normally, for example, emphysema, bronchitis, pneumonia, respiratory infections, etc. Dosage, and frequency of administration of the compounds or prodrugs thereof, will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

Effective dosages may be estimated initially from in vitro assays. For example, an initial dosage for use in animals may be formulated to achieve a circulating blood or serum concentration of active compound that is at or above an IC 50 of the particular compound as measured in an in vitro assay, such as the in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, latest edition, supra, and the references cited therein.

Initial dosages may also be estimated from in vivo data, such as animal models. Animal models useful for testing the efficacy of compounds to treat or prevent the various diseases described above are well-known in the art. Suitable animal models of hypersensitivity or allergic reactions are described in Foster, 1995, Allergy 50(21Suppl):6-9, discussion 34-38 and Tumas et al., 2001, J. Allergy Clin. Immunol. 107(6): 1025-1033. Suitable animal models of allergic rhinitis are described in Szelenyi et al., 2000, Arzneimittelforschung 50(11):1037-42; Kawaguchi et al., 1994, Clin. Exp. Allergy 24(3):238-244 and Sugimoto et al., 2000, Immunopharmacology 48(1):1-7. Suitable animal models of allergic conjunctivitis are described in Carreras et al., 1993, Br. J. Ophthalmol. 77(8):509-514; Saiga et al., 1992, Ophthalmic Res. 24(1):45-50; and Kunert et al., 2001, Invest. Ophthalmol. Vis. Sci. 42(11):2483-2489. Suitable animal models of systemic mastocytosis are described in O'Keefe et al., 1987, J. Vet. Intern. Med. 1(2):75-80 and Bean-Knudsen et al., 1989, Vet. Pathol. 26(1):90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al., 1996, J. Immunol. 157(12):5503-55 11. Suitable animal models of atopic disorders such as atopic dermatitis, atopic eczema and atopic asthma are described in Chan et al., 2001, J. Invest. Dermatol. 117(4):977-983 and Suto et al., 1999, Int. Arch. Allergy Immunol. 120(Suppl 1):70-75. Suitable animal models of transplant rejection, such as models of the HVGR are described in O'Shea et al., 2004, Nature Reviews Drug Discovery 3:555-564; Cetkovic-Curlje & Tibbles, 2004, Current Pharmaceutical Design 10:1767-1784; and Chengelian et al., 2003, Science 302:875-878. Suitable animal models of vasculitis are described in Pelletier et al., 1987 Nephrol Dial Transplant 1:211-218, Mathieson et al., 1992 Lab Invest. 67:121-129, and Xiao et al., 2002, J. Clin Invest 110:955. A suitable animal model for gout is described in Getting et al., 1997, J Pharmacol. Exp. Ther. 283:123. A suitable model for lupus is described in Bielschowsky et al, 1959, Proc. Univ. Otago Med School 37:9 and Monneaux et al, 2001, International Immunology 13(9):1155-1163. A suitable model for rheumatoid arthritis is described in Cope, 2007, Arthritis Research: Methods and Protocos, Springer, p 191-215 and Knight et al, 1992, Clin Exp Immunol 20(3):459-465. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) that are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) LD 50/ED 50 effect is the therapeutic index (LD 50 is the dose lethal to 50% of the population and ED 50 is the dose therapeutically effective in 50% of the population). Compounds(s) that exhibit high therapeutic indices are preferred.

Kits

The compounds and/or prodrugs described herein may be assembled in the form of kits. In some embodiments, the kit provides the compound(s) and reagents to prepare a composition for administration. The composition may be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In some embodiments, the therapeutic agents are other anti-cancer and anti-neoplastic compounds. These compounds may be provided in a separate form, or mixed with the compounds of the present invention.

The kits will include appropriate instructions for preparation and administration of the composition, side effects of the compositions, and any other relevant information. The instructions may be in any suitable format, including, but not limited to, printed matter, videotape, computer readable disk, or optical disc.

Uses of Compounds and Pharmaceutically Acceptable Compositions

The compounds and compositions described herein are generally useful for the inhibition of kinase activity of one or more enzymes. Kinases include, for example, protein kinases, lipid kinases (e.g., phosphatidylinositol kinases PI-3, PI-4) and carbohydrate kinases. Further information relating to kinase structure, function and their role in disease or disease symptoms is available at the Protein Kinase Resource website (http://Ikinases.sdsc.edu/html/index.shtml).

It will be appreciated that compounds described herein are preferably useful as inhibitors of Syk, though they may also inhibit tyrosine, serine/threonine or histidine protein kinases. Examples of kinases that may be inhibited by the compounds and compositions described herein and against which the methods described herein are useful include, but are not limited to, SYK, LCK, IRK (=INSR=Insulin receptor), IGF-1 receptor, MK2, ZAP-70, Aurora-2, PRAK, ROCK, CAK, cMET, IRAK1, IRAK2, BLK, BMX, BTK, FRK, FGR, FYN, HCK, ITK, LYN, TEC, TXK, YES, ABL, SRC, EGF-R (=ErbB-1), ErbB-2 (=NEU=HER 2), ErbB-3, ErbB-4, FAK, FGF1R (=FGR-1), FGF2R (=FGR-2), IKK-1 (=IKK-α=CHUK), IKK-2 (=IKK-β), MET (=c-Met), NIK, PGDF receptor α, PDGF receptor β, TIE1, TIE2 (=TEK), VEGFR 1 (=FLT-1), VEGFR 2 (=KDR), FLT-3, FLT-4, KIT, CSK, JAK1, JAK2, JAK3, TYK2, RIP, RIP-2, LOK, TAKI, RET, ALK, MLK3, COT, TRKA, PYK2, EPHB4, RON, GSK3, UL13, ORF47, ATM, CDK (including all subtypes), PKA, PKB (including all PKB subtypes) (=AKT-1, AKT-2, AKT-3), PKC (including all PKC subtypes), REDK, SAPK, PIM, PDK, PIM, ERK and BARK, and all subtypes of these kinases. The compounds and compositions of the invention are therefore also particularly suited for the treatment of diseases and disease symptoms that involve one or more of the aforementioned kinases.

The compounds described herein inhibit protein kinases in vitro assays. Thus, in still another aspect of the invention, methods of inhibiting protein kinases are provided. The methods generally involve contacting a protein kinase with an amount of one or more compounds described herein, and/or prodrugs, salts, hydrates, solvates and/or N-oxides thereof, effective to inhibit its activity. The methods may be practiced in vitro contexts, or in vivo contexts as a therapeutic approach towards the treatment or prevention of disorders responsive to protein kinase inhibition. Protein kinases that can be inhibited with the compounds desired herein include, but are not limited Syk, JAK1, JAK3, Axl, Lck and Lyn Kinases.

In still another aspect of the invention, methods of treating, inhibiting, and/or preventing diseases that are responsive to protein kinase inhibition, or in which inappropriate protein kinase activity plays a role, are provided. The methods may be practiced in animals in veterinary contexts and/or in humans. The methods generally involve administering to an animal or human subject an amount of one or more compounds described herein, and/or prodrugs, salts, hydrates, solvates and/or N-oxides thereof, effective to treat and/or prevent the particular disease. The compound(s) per se can be administered to the subject, or the compound(s) can be administered in the form of a composition. Diseases and other conditions that are responsive to protein kinase inhibition, and/or that are believed to be effected, at least in part, by inappropriate protein kinase activity, that can be treated, inhibited, and/or prevented according to the methods include, but are not limited to: autoimmune diseases, such as vasculitis, rheumatoid arthritis, multiple sclerosis, and systemic lupus erythematosus; transplant rejection; graft-versus-host disease; hyperproliferative disorders, such as tumors, psoriasis; pannus formation in rheumatoid arthritis; restenosis following angioplasty and atherosclerosis, osteoporosis; and diseases in which cells receive pro-inflammatory signals, such as asthma, inflammatory bowel disease and pancreatitis. Metabolic diseases that have an inflammatory component (such as gout) would also be responsive to these drugs.

In particular, inhibition of Syk and/or Lyn kinase would be expected to be useful in treating, inhibiting, and/or preventing diseases that are characterized by, caused by and/or associated with the IgE receptor signaling cascade, which leads to degranulation of immune cells such as mast cells, and the consequent release of mediators of inflammation. Such diseases include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, postsurgical scars, pulmonary fibrosis, vascular spasms, migraine, reperfusion injury and post myocardial infarction), diseases associated with tissue destruction (e.g., chronic obstructive pulmonary disease), diseases associated with tissue inflammation (e.g., irritable bowel syndrome, spastic colon and inflammatory bowel disease), inflammation and scarring.

In another embodiment, inhibition of Syk kinase would be expected to be useful in treating, inhibiting, and/or preventing diseases that are characterized by, caused by and/or associated with autoimmune diseases and/or symptoms of such diseases. Such autoimmune diseases include, but are not limited to, those autoimmune diseases that are frequently designated as single organ or single cell-type autoimmune disorders and those autoimmune diseases that are frequently designated as systemic autoimmune disorders. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia (including immune thrombocytopenia purpura), sympathetic ophthalmia, myasthenia gravis, Graves' disease, primary biliary cirrhosis, chronic aggressive hepatitis, ulcerative colitis and membranous glomerulopathy. Non-limiting examples of diseases often designated as systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be B cell (humoral) or T-cell based, include autoimmune alopecia, Type I or juvenile onset diabetes, and thyroiditis.

Inhibition of JAK kinase is expected to be useful in treating, inhibiting, and/or preventing diseases that are characterized by, caused by and/or associated with signaling cascades of cytokine receptors that involve the common gamma chain, such as, for example, the IL-4, IL-7, IL-5, IL-9, IL-15 and IL-21, or IL-2, IL-4, IL-7, IL-9, IL-15 and IL-21 receptor signaling cascades. Such diseases include, by way of example and not limitation, allergies, asthma, autoimmune diseases such as transplant rejection (e.g., kidney, heart, lung, liver, pancreas, skin; host versus graft reaction (HVGR), etc.), rheumatoid arthritis, and amyotrophic lateral sclerosis, T-cell mediated autoimmune diseases such as multiple sclerosis, psoriasis and Sjogren's syndrome, Type II inflammatory diseases such as vascular inflammation (including vasculitis, arteritis, atherosclerosis and coronary artery disease), diseases of the central nervous system such as stroke, pulmonary diseases such as bronchitis obliteraus and primary pulmonary hypertension, and solid, delayed Type IV hypersensitivity reactions, and hematologic malignancies such as leukemia and lymphomas.

Inhibition of Axl kinase is expected to be useful in treating, inhibiting, and/or preventing diseases that are characterized by, caused by and/or associated with apoptosis induced by serum starvation, TNF-α or the viral protein E1A, as well as migration and cell differentiation. Such diseases include, by way of example and not limitation, solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis and cataracts.

In yet another aspect of the invention, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for preventing or delaying the onset, or treating or lessening the severity, of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for preventing, delaying the onset, treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment and approval by the FDA. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. Dosage amounts will typically be in the range of from about 0.0001 or 0.001 or 0.01 mg/kg/day to about 100 mg/kg/day. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. As described generally above, the compounds of the invention are useful as inhibitors of protein kinases. In one embodiment, the compounds and compositions of the invention are inhibitors of one or more of SYK, PRAK, GSK3, ERK2, CDK2, MK2, SRC, or Aurora-2 kinase, and thus, without wishing to be bound by any particular theory, the compounds and compositions are particularly useful for treating or lessening the severity of a disease, condition, or disorder where activation of one or more of PRAK, GSK3, ERK2, CDK2, MK2, SRC, SYK, or Aurora-2 kinase is implicated in the disease, condition, or disorder. When activation of PRAK, GSK3, ERK2, CDK2, MK2, SRC, SYK, or Aurora-2 kinase is implicated in a particular disease, condition, or disorder, the disease, condition, or disorder may also be referred to as "PRAK, GSK3, ERK2, CDK2, MK2, SRC, SYK, or Aurora-2 kinase-mediated disease" or disease symptom. Accordingly, in another aspect, the present invention provides a method for treating or lessening the severity of a disease, condition, or disorder where activation or one or more of PRAK, GSK3, ERK2, CDK2, MK2, SRC, SYK, or Aurora-2 kinase is implicated in the disease state.

The activity of a compound utilized in this invention as an inhibitor of PRAK, GSK3, ERK2, CDK2, MK2, SRC, SYK, or Aurora-2 kinase, may be assayed in vitro, in vivo or in a cell line. In vitro assays include assays that determine inhibition of either the phosphorylation activity or ATPase activity of activated PRAK, GSK3, ERK2, CDK2, MK2, SRC, SYK, or Aurora-2 kinase. Alternate in vitro assays quantitate the ability of the inhibitor to bind to PRAK, GSK3, ERK2, CDK2, MK2, SRC, SYK, or Aurora-2 kinase. Inhibitor binding may be measured by radiolabeling the inhibitor prior to binding, isolating the inhibitor/PRAK, inhibitor/GSK3, inhibitor/ERK2, inhibitor/CDK2, inhibitor/MK2, inhibitor/SRC, inhibitor/SYK, or inhibitor/Aurora-2 kinase complex and determining the amount of radiolabel bound. Alternatively, inhibitor binding may be determined by running a competition experiment where new inhibitors are incubated with PRAK, GSK3, ERK2, CDK2, MK2, SRC, SYK, or Aurora-2 kinase bound to known radioligands.

The term "measurably inhibit", as used herein means a measurable change in PRAK, GSK3, ERK2, CDK2, MK2, SRC, SYK, or Aurora-2 kinase activity between a sample comprising said composition and a PRAK, GSK3, ERK2, CDK2, MK2, SRC, SYK, or Aurora-2 kinase kinase and an equivalent sample comprising PRAK, GSK3, ERK2, CDK2, MK2, SRC, SYK, or Aurora-2 kinase kinase in the absence of said composition.

The term "Aurora-2-mediated disease" or "Aurora-2-mediated condition", as used herein, means any disease or other deleterious condition in which Aurora is known to play a role. The terms "Aurora-2-mediated disease" or "Aurora-2-mediated condition" also mean those diseases or conditions that are alleviated by treatment with an Aurora-2 inhibitor. Such conditions include, without limitation, colon, breast, stomach, and ovarian cancer.

The terms "ERK-mediated disease" or "ERK-mediated condition", as used herein mean any disease or other deleterious condition in which ERK is known to play a role. The terms "ERK-2-mediated disease" or "ERK-2-mediated condition" also mean those diseases or conditions that are alleviated by treatment with an ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders, and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. ERK-2 protein kinase and its implication in various diseases has been described (Bokemeyer et al., Kidney Int. 1996, 49, 1187; Anderson et al., Nature 1990, 343, 651; Crews et al., Science 1992, 258, 478; Bjorbaek et al., J. Biol. Chem. 1995, 270, 18848; Rouse et al., Cell 1994, 78, 1027; Raingeaud et al., Mol. Cell Biol. 1996, 16, 1247; Chen et al., Proc. Natl. Acad. Sci. USA 1993, 90, 10952; Oliver et al., Proc. Soc. Exp. Biol. Med. 1995, 210, 162; Moodie et al., Science 1993, 260, 1658; Frey and Mulder, Cancer Res. 1997, 57, 628; Sivaraman et al., J. Clin. Invest. 1997, 99, 1478; Whelchel et al., Am. J. Respir. Cell Mol. Biol. 1997, 16, 589).

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases (e.g., Alzheimer's disease, Huntington's disease, Parkinson's disease and basal ganglia movement disorders, chorea, dystonia, Wilson Disease, Pick Disease, frontal lobe degeneration, progressive supranuclear palsy (PSP), Creutzfeldt-Jakob Disease, taupathology and corticobasal degeneration (CBD)), psychotic disorders (e.g., schizophrenia, AIDS-associated dementia, depression, bipolar disorder, and anxiety disorders), cardiovascular diseases, allergy, asthma, diabetes, amyotrophic lateral sclerosis (AML, Lou Gehrig's disease), multiple sclerosis (MS), cardiomyocyte hypertrophy, reperfusion/ischemia, stroke, and baldness.

The term "Src-mediated disease" as used herein means any disease or other deleterious condition in which Src kinase plays a role. Such diseases or conditions include, without limitation, cancers such as colon, breast, hepatic and pancreatic cancer, autoimmune diseases such as transplant rejection, allergies, rheumatoid arthritis, leukemia, bone remodeling diseases such as osteoporosis and viral diseases such as hepatitus B infection.

The terms "CDK-2-mediated disease" or "CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P., Current Medicinal Chemistry, 7, 1213 1245 (2000); Mani, S., Wang, C., Wu, K., Francis, R. and Pestell, R., Exp. Opin. Invest. Drugs, 9, 1849 (2000); Fry, D. W. and Garrett, M. D., Current Opinion in Oncologic, Endocrine & Metabolic Investigational Drugs, 2, 40 59 (2000).

The terms "PRAK-mediated disease" or "PRAK-mediated condition", as used herein mean any disease or other deleterious condition in which PRAK is known to play a role. The terms "PRAK-mediated disease" or "PRAK-mediated condition" also mean those diseases or conditions that are alleviated by treatment with a PRAK inhibitor. Such conditions include, without limitation, rheumatoid arthritis, multiple sclerosis (see Darlington, C. L, Current Opinion in Anti-inflammatory & Immunomodulatory Investigational Drugs, 1999, 1 (3), 190 198), Crohns Disease, autoimmune diseases, atherosclerosis, restenosis, psoriasis, allergic disorders including asthma, and inflammation.

The term "Syk-mediated disease" or "Syk-mediated condition", as used herein, means any disease or other deleterious condition in which Syk protein kinase is known to play a role. Such conditions include, without limitation, auto-immune, allergic and other disorders described herein.

The term "MK2-mediated disease" or "MK2-mediated condition", as used herein, means any disease or other deleterious condition in which MK2 protein kinase is known to play a role. Such conditions include, without limitation, inflammatory disorders, arthritis, ischemia/reperfusion (see, J. Biol. Chem. 2002, 277 (46), 43968 72), and asthma (See., Am J Respir Crit Care Med. 2001 Dec. 1; 164(11):2051 6).

In other embodiments, the invention relates to a method of enhancing glycogen synthesis and/or lowering blood levels of glucose in a patient in need thereof, comprising administering to said patient a therapeutically effective amount of a composition of the invention. This method is especially useful for diabetic patients.

In yet another embodiment, the invention relates to a method of inhibiting the production of hyper-phosphorylated Tau protein in a patient in need thereof, comprising administering to said patient a therapeutically effective amount of a composition of the invention. This method is especially useful in halting or slowing the progression of Alzheimer's disease.

In still another embodiment, the invention relates to a method of inhibiting the phosphorylation of β-catenin in a patient in need thereof, comprising administering to said patient a therapeutically effective amount of a composition of the invention. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

Chemotherapeutic agents or other anti-proliferative agents may be combined with the compounds of this invention to treat proliferative diseases and cancer. For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (for example, interferons and/or interleukins), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec®, adriamycin, dexamethasone, and cyclophosphamide. For a more comprehensive discussion of updated cancer therapies see, www.nci.nih.gov, a list of the FDA approved oncology drugs at www.fda.gov/cder/cancer/druglistframe.htm, and The Merck Manual, Seventeenth Ed. 1999.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as β interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as β-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting PRAK, GSK3, ERK2, CDK2, MK2, SRC, SYK, or Aurora-2 kinase activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of PRAK, GSK3, ERK2, CDK2, MK2, SRC, SYK, or Aurora-2 kinase activity in a biological sample is useful for a variety of purposes that are known to one of skill in the art. Examples of such purposes include, but are not limited to, blood transfusion, organ-transplantation, biological specimen storage, and biological assays.

Other aspects of the invention include, but are not limited to, intermediates and methods useful for synthesizing the stereoisomerically enriched compounds and prodrugs, as described herein.

In yet another aspect of the invention, a method for screening for SYK-inhibiting compounds is provided. Inhibitors of Syk kinase can be screened from a compound library in an in vitro Syk kinase reaction using poly GluTyr as the substrate. Reactions can be quantified by measuring ATP used by the kinase in a luciferase reporter assay. In this assay, purified Syk kinase is mixed with potential inhibitor compound in the presence of ATP and poly GluTyr substrate. After the kinase reaction, remaining ATP is detected by adding luciferin and luciferase. In the presence of ATP, luciferrin is oxidized by luciferase to produce oxyluciferin and light. The light is quantitated and corresponds to the amount of ATP remaining from the original reaction. In this system, decreased light corresponds to increased kinase activity. Reactions in which compounds inhibit kinase activity will have more ATP remaining, so the amount of light produced will be relatively high.

The invention will be illustrated in more detail with reference to the following Examples, but it should be understood that the present invention is not deemed to be limited thereto.

Example 1

In Vivo Test Procedures for SYK Inhibitors

Inhibitors of Syk kinase were screened from a library of over 100,000 compounds. In order to maximize the potential for finding a viable drug candidate, compounds were chosen for maximum diversity, thereby allowing detection of representatives from the largest number of chemical families. Compounds were screened for the ability to inhibit Syk phosphorylation of the kinase substrate poly GluTyr. Reactions were quantified by measuring ATP usage using a luciferase reporter assay. Of the compounds screened, 342 were active in the primary screen; 101 compounds were confirmed active by retesting the active compounds in quadruplicate. Of the confirmed hits, 9 met the criteria of reproducible dose response curves with $IC_{50}$ values less than 30 µM.

Assay Development

The Syk kinase assay was optimized for high throughput screening in 384 well plates. Kinase activity was measured with the Kinase-glo kit (Promega) that detects ATP using the luciferase reporter system.

FIG. 1 shows the assay used to detect activity. Kinases use ATP to phosphorylate a substrate. After incubation of the kinase with substrate and ATP, luciferin and luciferase are added to the assay. In the presence of ATP, luciferin is oxidized by luciferase, and the light produced is quantified on a plate reader. In this assay, increased kinase activity yields decreased light production.

The ATP standard curve produced with the Kinase-glo kit was linear up to 5 µM ATP. A final ATP concentration of 0.5 µM was used for all subsequent screening assays.

Figure 2:
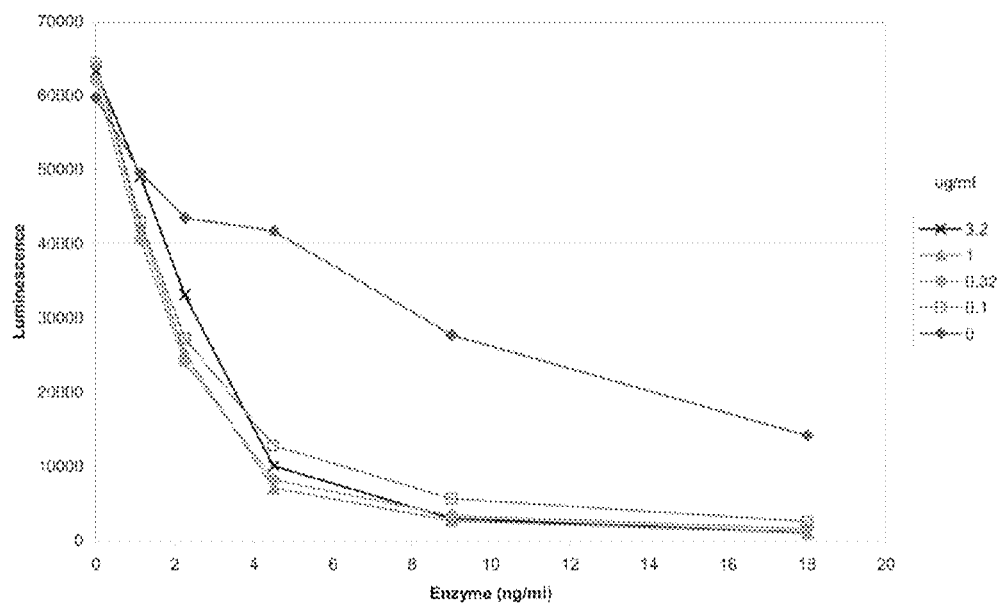
FIG. 2 is a graph of luminescence against enzyme concentration.

The Syk kinase assay was optimized for screening by titrating both syk kinase (Millipore, USA) and the substrate, poly Glu-Tyr (Sigma, St. Louis, Mo.) (FIG. 2). In the absence of substrate, there was significant reduction of ATP most likely due to syk autophosphorylation. Increasing substrate from 0.1 to 3.2 µg/ml poly Glu-Tyr did not increase ATP consumption. Final assay conditions used were 0.32 µg/ml substrate and 9 ng/ml syk kinase.

Staurosporine (Cayman Chemical, Ann Arbor, Mich.), a known syk kinase inhibitor, was used to characterize the assay. Staurosporine showed potent, reproducible inhibition of syk kinase, with an $IC_{50}$ value of 2.9 nM. Staurosporine was included on every plate in the screening assay, using a high concentration (100 nM) to totally inhibit the syk kinase reaction.

Primary Screen

Based on these data, a screen was conducted using compounds from a compound library. These compounds were chosen for maximum chemical diversity. On each plate, 336 compounds were tested along with 44 uninhibited control samples and 4 inhibited control samples (containing 100 nM staurosporine). Using the TiMo head on the Tecan Freedom EVO robot, 5 µl of test compounds (100 µM compound in assay buffer with 10% DMSO) were dispensed to each of the assay wells of a 384 well microplate. Final concentration of compounds was 25 µM. A 10 ul solution of Syk kinase (9 nM final concentration) was added to the wells, followed by the substrates (5 µl of 2 mM ATP, 1.28 µg/ml poly Glu4Tyr; final concentrations were 0.5 µM and 0.32 µg/ml, respectively). Reactions were incubated for 2 hours at room temperature.

Then, 5 µl of Kinase-glo reagent was added for 10 minutes. Luminescence was recorded on a BMG Pherastar reader.

The Kinase-glo assay is an indirect measurement of syk kinase activity as it measures the amount of ATP not used by syk. Consequently, in the absence of inhibition, the amount of light generated is low. Kinase inhibitors reduce consumption of ATP, resulting in increased generation of light. One advantage of this protocol is that compounds that interfere with the luciferase assay and consequent light production are not scored as kinase inhibitors.

Assay performance was assessed by the variability of the control wells. Controls were pooled based on a statistical analysis of similarity of the values. For the uninhibited controls, there were three separate groups. For the inhibited controls, there were two groups. The uninhibited controls values were somewhat variable with the percent coefficient of variation (% CV) all greater than 10%. A cutoff value of 3× the standard deviation of the uninhibited wells (3×SD) was set for each pool group. The 342 active compounds were selected based on these cutoff values.

Figure 3:
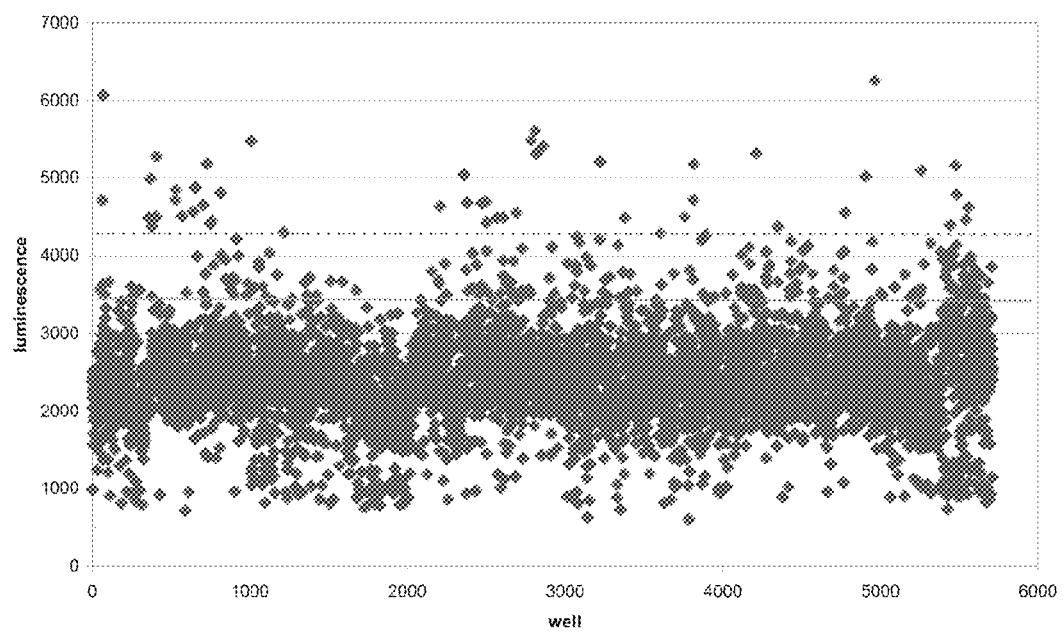
FIG. 3 is a graph of luminescence against well number.

FIG. 3 shows data from about half of the primary screen. The cutoff value of 3×SD is shown as the solid line. The dashed line represents the staurosporine inhibited control value.

Secondary Screen.

For secondary assays, compounds identified in the primary screen were tested in quadruplicate under the exact same assay conditions, again using 3× the standard deviation of uninhibited control values as the cutoff. Of the original 342 hits, 101 compounds were confirmed active.

Dose Response Assays

Dose response assays were conducted on the 101 confirmed active compounds. These were tested at 11 concentrations, from 0.3 µM to 100 µM. Compounds that gave dose response curves with Hill slopes between 0.5 and 2 were retested in duplicate. Only those compounds exhibiting reproducible dose response curves with $IC_{50}$ less than 30 uM were to be considered for further development. Nine compounds were identified at the end of the final test.

Syk Inhibition Assay

Inhibition of syk can be determined in a syk dependent cellular assay such as neutrophil respiratory burst, degranulation and phagocytosis.

During the respiratory burst, reactive oxygen intermediates such as superoxide anion, hydroxyl radical, and hydrogen peroxide are produced. To determine the ability of an inhibitor of syk to inhibit respiratory burst, superoxide anion production can be measured in a microplate assay using the reduction of cytochrome c as a reporter assay.

Neutrophils ($1\times10^6$) can be added to microtiter plates previously coated with fibrinogen. Samples can be equilibrated at 37° C. and the reaction initiated by adding 20 ng/ml TNFα. Reduction of cytochrome c can be quantified by measuring absorbance at 550 nm using a microplate reader. Inhibition of respiratory burst will be indicated by a decrease in cytochrome c reduction in comparison to the positive control.

The ability of inhibitors to inhibit degranulation can be assessed by measuring lactoferrin, a secondary granule product using an enzyme linked immunosorbent assay (ELISA). Neutrophils plated into fibrinogen coated wells of a microtiter plate can be stimulated with 20 ng/ml TNFα in the presence of syk inhibitors. After appropriate times, supernatants can be tested for lactoferrin. In this assay, lactoferrin from the supernatant is captured by a monoclonal antibody (MAb) that is coated on wells of a sectional microplate. A second LTF-MAb labeled with biotin is added to the well and binds with the captured LTF forming a "sandwich." A solution of streptavidin-peroxidase is then added. Streptavidin has a high affinity for biotin and once bound, its horseradish peroxidase (HRP) label is available for color development by addition of the substrate, o-phenylenediamine (OPD). This color development at 450 nm is proportional to the quantity of lactoferrin in the sample. Assays will be quantified in a microplate reader at 450 nm.

Inhibition of phagocytosis can be carried out using the CytoSelect™ 96-Well Phagocytosis Assay (Cell Biolabs, Inc). The phagocytic target is zymosan (*Saccharomyces cerevisiae*), made from yeast cell wall and is composed of a mixture of protein and carbohydrates. For this assay, neutrophils can be seeded onto fibrinogen coated wells in the presence of inhibitor. Zymosan is added for varying times, and phagocytosis detected by permeabilizing the cells and adding a detection reagent that can be quantified colorimetrically in a plate reader at 405 nm.

Compounds of the invention can be found to inhibit SYK. In certain embodiments, compounds may be shown to have Ki values less than 1.0 µM for SYK.

Example 2

Affect of Compounds on Syk Dependent Cellular Activity in Neutrophils

During the respiratory burst of activated neutrophils, reactive oxygen intermediates such as superoxide anion, hydroxyl radical, and hydrogen peroxide are produced. To determine the ability of compounds to affect syk dependent respiratory burst, superoxide anion production was measured in a microplate assay using the reduction of cytochrome c as a reporter assay. Respiratory burst can be induced through two different syk dependent signaling pathways, integrin mediated and Fc Receptor mediated. Compounds were tested in both pathways.

For respiratory burst assays, neutrophils ($1\times10^6$) were added to microtiter plates that were coated with fibrinogen for integrin signaling or uncoated for Fc receptor signaling. For integrin signaling, the reaction was initiated by adding TNFα to 200 ng/ml in the presence of cytochrome c and reactions incubated at 37° C. for 1 hr. For Fc Receptor signaling, cells were incubated with 200 ng/ml TNFα at 37° C. for 15 min, then either anti-myeloperoxidase or anti-Pr3 antibody added and further incubated for 45 minutes. At the end of the incubations, reduction of cytochrome c was quantified by measuring absorbance at 550 nm using a microplate reader. Inhibition of respiratory burst was indicated by a decrease in cytochrome c reduction in comparison to the positive control.

The ability of inhibitors to inhibit both integrin and Fc receptor degranulation was assessed by measuring lactoferrin, a secondary granule product using an enzyme linked immunosorbent assay (ELISA) for lactoferrin. Reactions were set up as for respiratory burst assays above and incubated for 1 hr. Supernatants were then tested for lactoferrin. Lactoferrin from the supernatant was captured by a monoclonal antibody (MAb) coated on wells of a sectional microplate. A second LTF-MAb labeled with biotin was added to the well and bound with the captured LTF forming a "sandwich." A solution of streptavidin-peroxidase was then added. Streptavidin has a high affinity for biotin and once bound, its horseradish peroxidase (HRP) label was available for color development by addition of the substrate, o-phenylenediamine (OPD). Color development at 450 nm is proportional to the quantity of lactoferrin bound in the plate. Assays were quantified in a microplate reader at 450 nm.

Inhibition of phagocytosis was carried out using the CytoSelect™ 96-Well Phagocytosis Assay (Cell Biolabs, Inc). The phagocytic target was zymosan (*Saccharomyces cerevisiae*), made from yeast cell wall. For this assay, neutrophils were seeded onto fibrinogen coated wells in the presence of inhibitor. Zymosan was added, and reactions incubated for 1.5 hr. Phagocytosis was detected by permeabilizing the cells and adding a detection reagent that was quantified colorimetrically in a plate reader at 405 nm.

Inhibition of syk phosphorylation was tested using the FACEMaker in cell Western Blot kit from Active Motif (Carlsbad, Calif.). In this assay, freshly isolated neutrophils were plated onto fibrinogen coated wells and stimulated with TNF at 200 ng/ml. After 1 hr., cells were fixed in formaldehyde and the Western Blot performed according to the kit instructions, with the final colorimetric product read in a plate reader. Results were corrected for cell number by subsequent staining of the cells with crystal violet and recording OD at 630 nm.

Compounds of the invention can be found to inhibit SYK. In certain embodiments, compounds may be shown to have Ki values less than 1.0 µM for SYK.

Example 3

Selective Inhibition of Protein Kinases

Compound inhibition of a wide variety of protein kinases can be tested in a commercial kinase panel. Such a panel could include but is not limited to SYK, LCK, IRK (=INSR=Insulin receptor), IGF-1 receptor, MK2, ZAP-70, Aurora-2, PRAK, ROCK, CAK, cMET, IRAK1, IRAK2, BLK, BMX, BTK, FRK, FGR, FYN, HCK, ITK, LYN, TEC, TXK, YES, ABL, SRC, EGF-R (=ErbB-1), ErbB-2 (=NEU=HER 2), ErbB-3, ErbB-4, FAK, FGF1R (=FGR-1), FGF2R (=FGR-2), IKK-1 (=IKK-α=CHUK), IKK-2 (=IKK-β), MET (=c-Met), NIK, PGDF receptor α, PDGF receptor β, TIE1, TIE2 (=TEK), VEGFR 1 (=FLT-1), VEGFR 2 (=KDR), FLT-3, FLT-4, KIT, CSK, JAK1, JAK2, JAK3, TYK2, RIP, RIP-2, LOK, TAKI, RET, ALK, MLK3, COT, TRKA, PYK2, EPHB4, RON, GSK3, UL13, ORF47, ATM, CDK (including all subtypes), PKA, PKB (including all PKB subtypes) (=AKT-1, AKT-2, AKT-3), PKC (including all PKC subtypes), REDK, SAPK, PIM, PDK, PIM, ERK and BARK, and all subtypes of these kinases.

The affinity of a compound for the above kinases can also be determined in such a commercial kinase panel.

Inhibition of Protein Kinase Activity

Since most tyrosine kinases autophosphorylate when activated, the amount of phosphorylation can be determined in the presence and absence of compound using standard cell lines and Western Blotting techniques. Further cellular activity can be determined as described below.

Inhibition of FLT3 Activity

Inhibition of FLT3 activity can be determined by proliferation assays in human myeloid leukemia-derived cell lines such as EOL-1, MV4-11 or BV173. In 96 well plates, 50,000 cells are added per well with the compound and cultured at 37°, for 48 hours. Proliferation assays are then performed according to the instructions in the Cell Proliferation Kit 1 (MTT) (Roche, Indianapolis, Ind.). Results are reported as percent of untreated control.

Inhibition of PDGF Receptor Activity

Inhibition of PDGF receptor activity can be determined as for FLT3 activity using rat A10 smooth muscle cells.

Inhibition of KIT Activity

Inhibition of KIT activity can be determined by proliferation assay in HMC-1 cells by plating 50,000 cells per well in the presence or absence of inhibitor compound and assaying proliferation after 48 hours using an XTT based assay (Roche Molecular Biochemicals).

Inhibition of LCK Activity

Inhibition of LCK activity can be determined by conducting a mixed lymphocyte reaction. Mesenteric lymph nodes and spleens can be collected from C57BL/6J and Balb/c mice and cell suspensions prepared in RPMI 1640 with 10% calf serum. Equal volumes of the two suspensions can be mixed and plated into 96 well plates in the presence of inhibitor. After incubating at 37° for 42 hours, [3H]thymidine can be added and the mixtures cultured a further 6 hours after which cells are harvested on a cell harvester onto a glass fiber filter, dried and radioactivity counted on a scintillation counter.

Inhibition of JAK2

Inhibition of JAK2 activity can be determined using Invitrogen's CellSensor irf1-bla HEL Cell Line. These cells can be plated at 50,000 cells/well in a 384 well plate in the presence of compound. Plates can be incubated 4 to 16 hrs, then loaded with LiveBLAzer™-FRET B/G Substrate and fluorescence emission values obtained at 460 and 530 nm. Results are reported as the ratio of 460/530 values.

Inhibition of JAK1 and JAK3

Inhibition of JAK1 and JAK3 activity can be determined as for JAK2 using the irf1-bla CTLL-2 cell line and culturing for 5 hours before addition of LiveBLAzer™-FRET B/G Substrate for 2.5 hours.

Inhibition of RET Activity

Inhibition of RET activity can be determined in an NIH-3T3 soft agar assay. For this assay, NIH-3T3 cells are stably transfected with a RET expressing vector. Both transfected and untransfected cells are plated into 6 well plates at 10,000 cells/well in a medium containing 0.33% low melting agar and either DMSO or compound on a layer of 0.5% agar. Cells are incubated at 37°, adding fresh compound to the top layer every 3 days. Transfected cells in the absence of RET inhibitor form colonies. Colonies are counted every 15 days.

Inhibition of ZAP-70 Activity

Inhibition of ZAP-70 activity can be determined in a ZAP-70⁻ Jurkat T cell line which has been transfected with a vector expressing ZAP-70. Transfected cells can be stimulated with PMA in the presence and absence of compound, ZAP-70 immunoprecipitated, and the ZAP-70 kinase activity determined in a kinase assay using poly (4:1 Glu, Tyr) peptide as a substrate.

Example 4

Analysis of Various Syk Inhibitors

A series of compounds was evaluated using the assays described herein.

Inhibition of Respiratory Burst in Integrin/TNF Stimulated Neutrophils

Figure 4A:
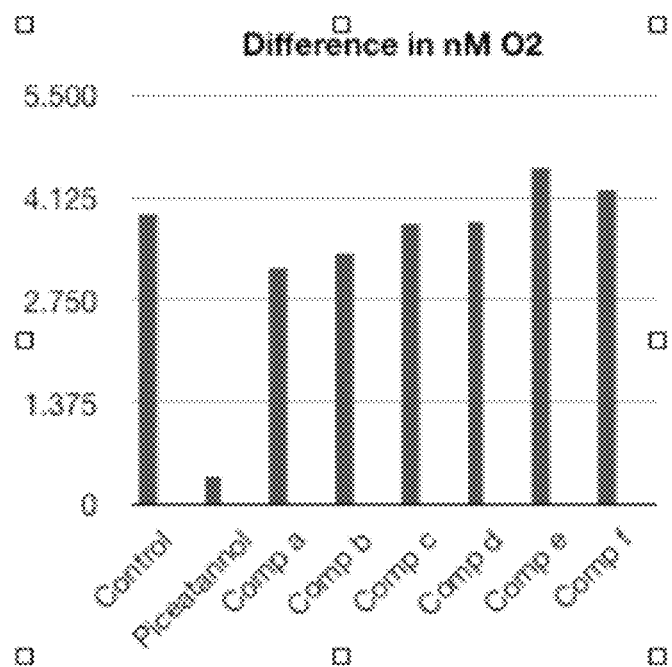
FIGS. 4A and 4B are charts showing the inhibition of respiratory burst in integrin/TNF stimulated neutrophils. Results are shown as the difference in nmoles of oxygen produced between stimulated and unstimulated neutrophils. Piceatannol is a commercially available kinase inhibitor used as a control. Compounds a-i in FIGS. 4A and 4B correlate to compounds 1-9 as described herein.
Figure 4B:
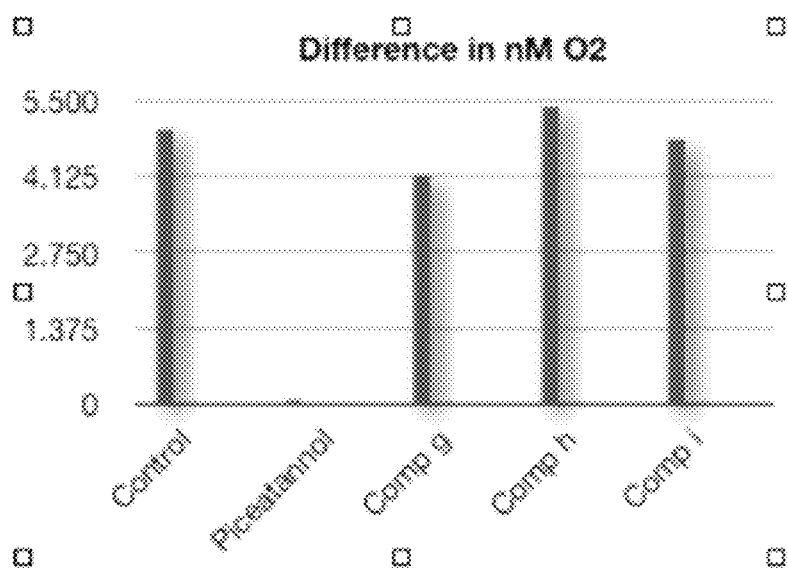

Neutrophils were isolated from healthy human donors using Polymorphprep (Axis Shield). Cells were equilibrated for 15 min. at 37° C. in the presence of 100 uM cytochrome c and 10 ug/ml compound, then plated into 96 well plates previously coated with 2 mg/ml fibrinogen at 1×10⁶ cells/well. Either vehicle or TNFα at 200 ng/ml was added and reactions incubated at 37° C. for 1 hr. Reduction of cytochrome c was measured by reading absorbance at 550 nm with a 490 nm reference in a spectrophotometer. Results are shown as the difference in nmoles of oxygen produced between stimulated and unstimulated neutrophils. Piceatannol is a commercially available kinase inhibitor used as a control. The results are shown in FIG. 4.

Figures 5A, 5B:
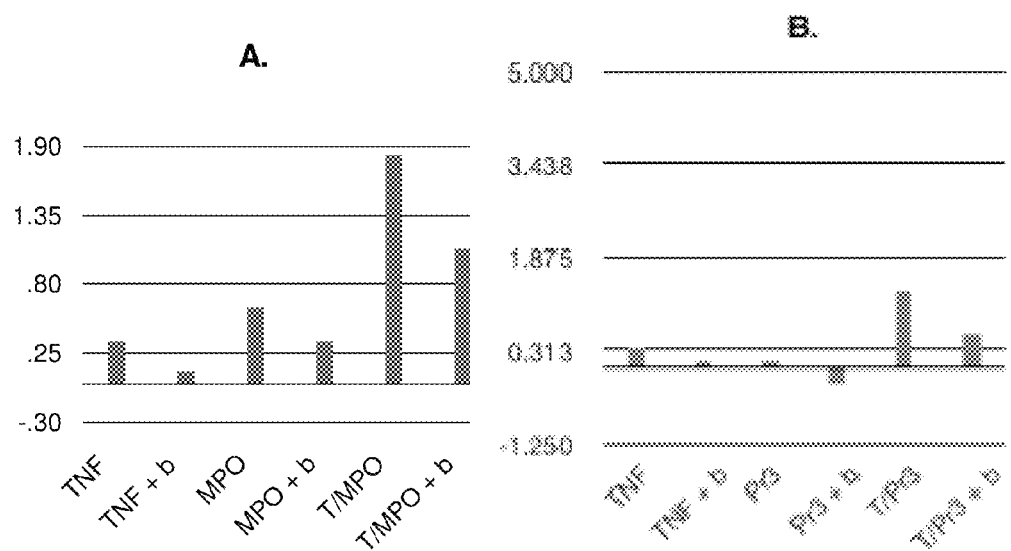
FIGS. 5 A-C are charts showing inhibition of respiratory burst in TNF/antineutrophil cytoplasmic antibody stimulated neutrophils following administration of Compound b), which correlates to Compound 2 as described herein. Results are shown as nmoles of oxygen produced. MPO is anti-myeloperoxidase antibody. Pr3 is anti-Pr3 antibody. a2m is alpha 2 macroglobulin antibody used as a control.
Figure 5C:
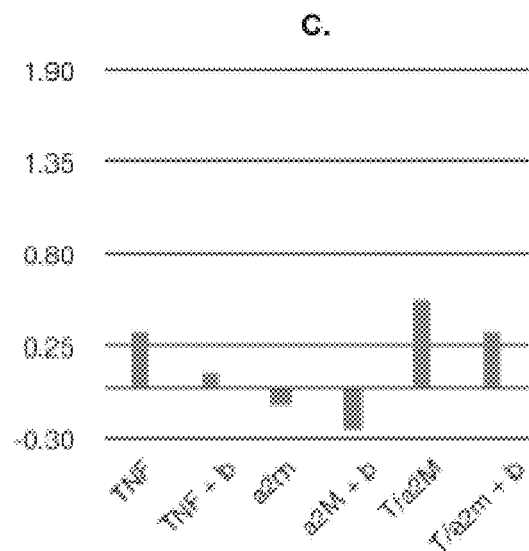

Compound b Inhibition of Respiratory Burst in TNF/Antibody Stimulated Neutrophils Neutrophils were isolated from healthy human donors using Polymorphprep (Axis Shield). Cells were pre-incubated with cytochalasin B at 5 ug/ml for 5 minutes at 37° C. Vehicle or compound at 10 ug/ml was added, followed by cytochrome c to 100 uM. Reactions were then aliquoted into wells of a 96 well strip plate. TNFα or vehicle was added to a concentration of 200 ng/ml and reactions stimulated for 15 minutes at 37° C. Antibodies (anti-MPO, anti-Pr3 or anti-alpha 2 macroglobulin) or vehicle were added and reactions incubated at 37° C. for 45 minutes. Reduction of cytochrome c was measured by reading absorbance at 550 nm with a 490 nm reference in a spectrophotometer. Results are shown as nmoles of oxygen produced. b is compound b, T is TNFα, MPO is anti-myeloperoxidase antibody. Pr3 is anti-Pr3 antibody. a2m is alpha 2 macroglobulin antibody used as a control. Results are shown in FIG. 5.

Figure 6A:
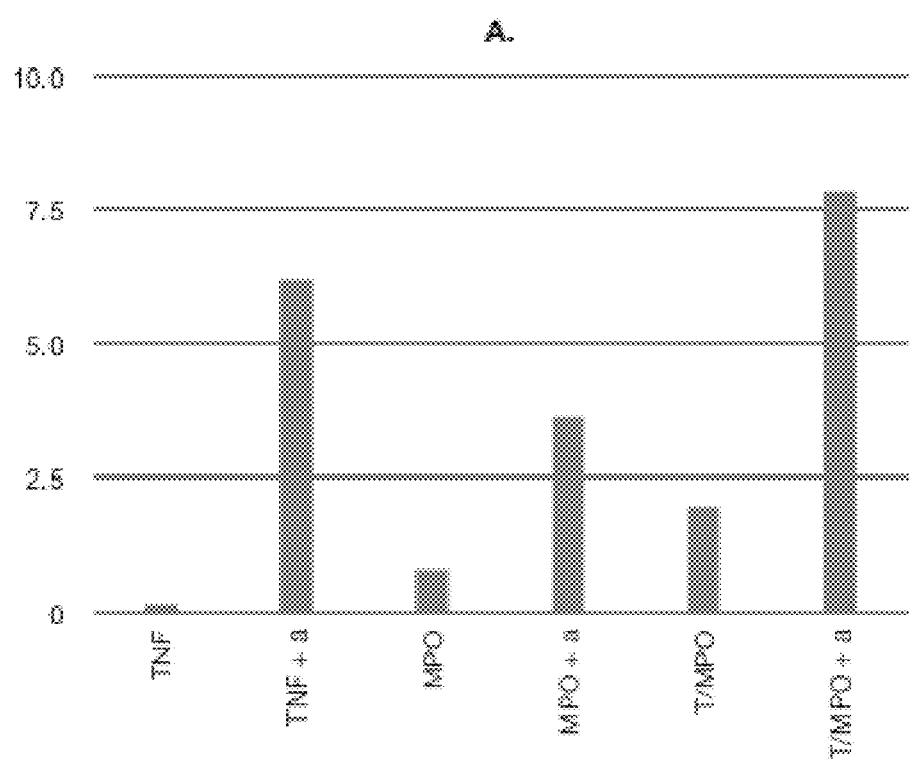
FIGS. 6A-C are charts showing the stimulation of respiratory burst in TNF/antineutrophil cytoplasmic antibody stimulated neutrophils, following administration of Compound a), referred to as Compound 1 herein. Results are shown as nmoles of oxygen produced. MPO is anti-myeloperoxidase antibody. Pr3 is anti-Pr3 antibody. a2m is alpha 2 macroglobulin antibody
Figure 6B:
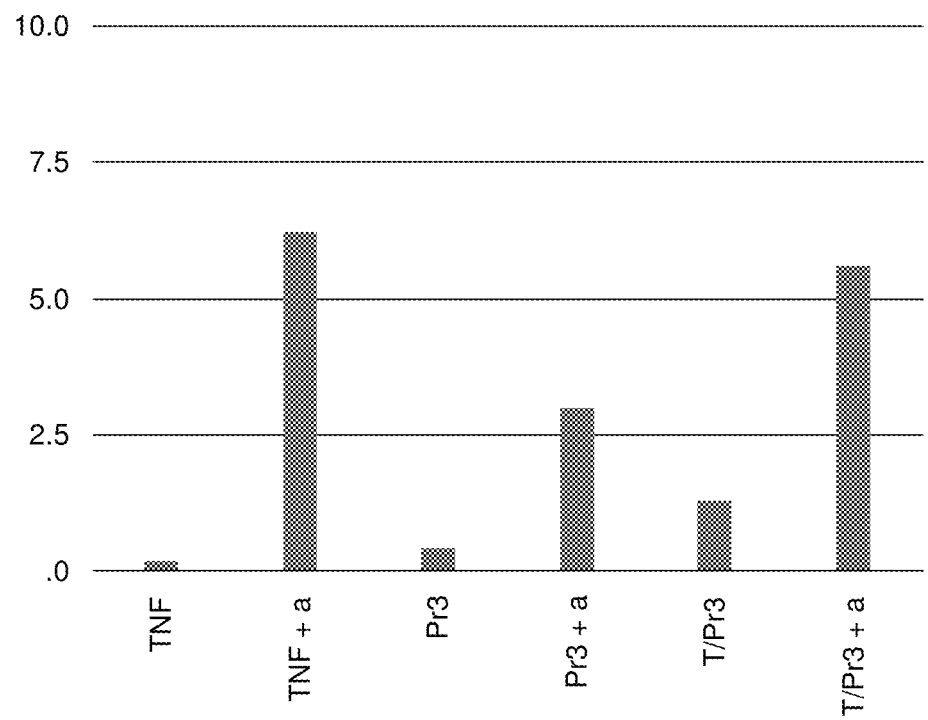
Figure 6C:
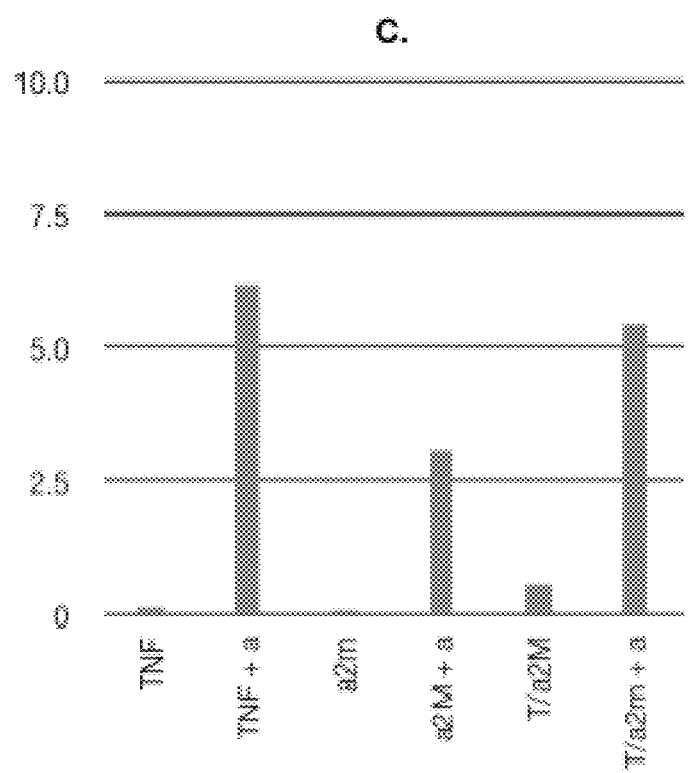

Compound a Stimulation of Respiratory Burst in TNF/Antineutrophil Cytoplasmic Antibody Stimulated Neutrophils Neutrophils were isolated from healthy human donors using Polymorphprep (Axis Shield). Cells were preincubated with cytochalasin B at 5 ug/ml for 5 minutes at 37° C. Vehicle or compound at 10 ug/ml was added, followed by cytochrome c to 100 uM. Reactions were then aliquoted into wells of a 96 well strip plate. TNFα or vehicle was added to a concentration of 200 ng/ml and reactions stimulated for 15 minutes at 37° C. Antibodies (anti-MPO, anti-Pr3 or anti-alpha 2 macroglobulin) or vehicle were added and reactions incubated at 37° C. for 45 minutes. Reduction of cytochrome c was measured by reading absorbance at 550 nm with a 490 nm reference in a spectrophotometer. Results are shown as nmoles of oxygen produced. a is compound a, T is TNFα, MPO is anti-myeloperoxidase antibody. Pr3 is anti-Pr3 antibody. a2m is alpha 2 macroglobulin antibody used as a control. Results are shown in FIG. 6.

Inhibition of Degranulation in Integrin/TNF Stimulated Neutrophils

Figure 7:
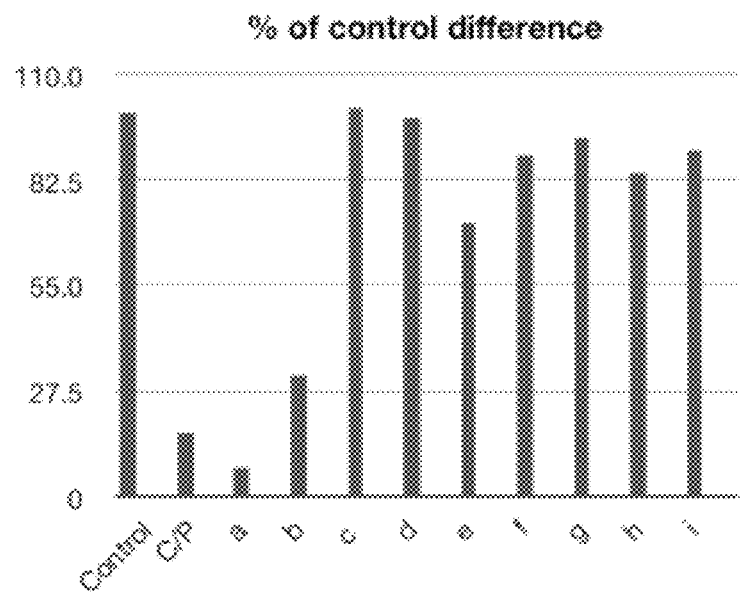
FIG. 7 is a chart showing the inhibition of degranulation in integrin/TNF stimulated neutrophils. Results are shown as ng/ml lactoferrin. C/P is piceatannol negative control. Compounds a-i in the Figures correspond to Compounds 1-9 in the specification.

Neutrophils were isolated from healthy human donors using Polymorphprep (Axis Shield). Cells were equilibrated for 15 min. at 37° C. in the presence of 100 uM cytochrome c and 10 ug/ml compound, then plated into 96 well plates previously coated with 2 mg/ml fibrinogen at $1 \times 10^6$ cells/well. Either vehicle or TNFα at 200 ng/ml was added and reactions incubated at 37° for 1 hr. Supernatants were removed and any remaining cells removed by centrifugation. The resulting supernatants were assayed in a commercial lactoferrin ELISA. (Oxis International) Results are shown as ng/ml lactoferrin. C/P is piceatannol negative control. Results are shown in FIG. 7.

Figure 8:
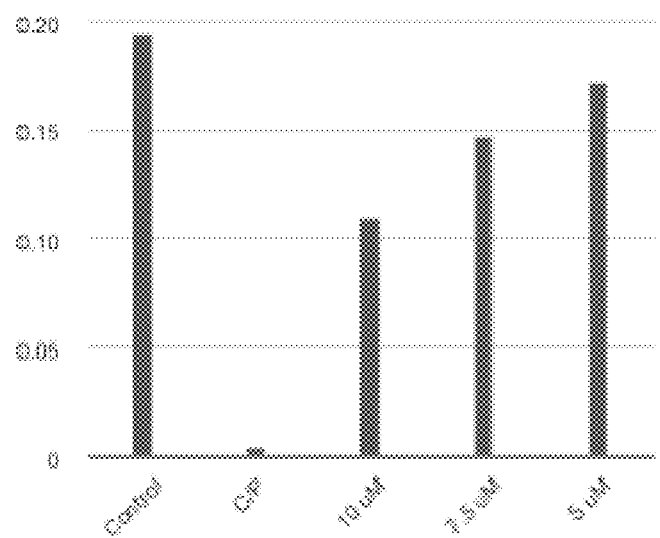
FIG. 8 is a chart showing the dose response inhibition of degranulation in integrin/TNF stimulated neutrophils, following administration of Compound b), referred to herein as Compound 2. Results are shown as ng/ml lactoferrin. C/P is piceatannol negative control.

Compound b Inhibition of Degranulation in Integrin/TNF Stimulated Neutrophils Dose Response Neutrophils were isolated from healthy human donors using Polymorphprep (Axis Shield). Cells were equilibrated for 15 min. at 37° C. in the presence of varying concentrations of compound, then plated into 96 well plates previously coated with 2 mg/ml fibrinogen at $1 \times 10^6$ cells/well. Either vehicle or TNFα at 200 ng/ml was added and reactions incubated at 37° C. for 1 hr. Supernatants were removed and any remaining cells removed by centrifugation. The resulting supernatants were assayed in a commercial lactoferrin ELISA. (Oxis International.) Results are shown as ng/ml lactoferrin. C/P is piceatannol negative control. Results are shown in FIG. 8.

Figure 9:
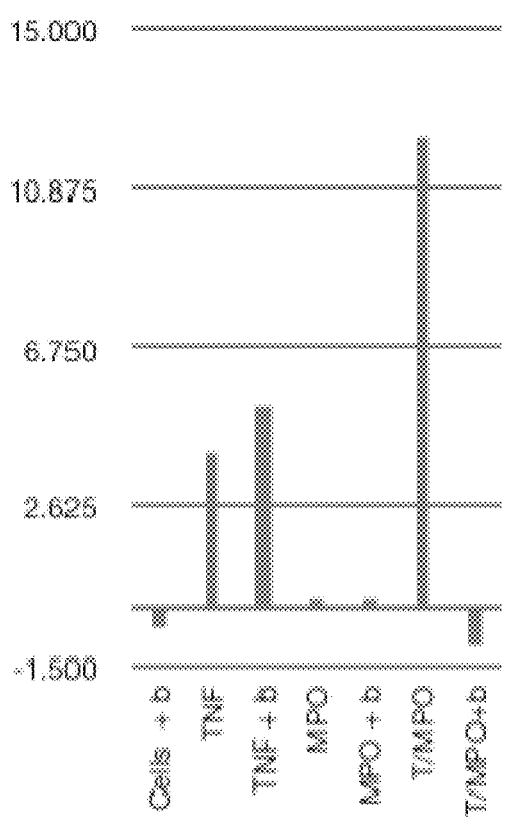
FIG. 9 is a chart showing the inhibition of respiratory burst by compound b), referred to herein as Compound 2, in TNF/antineutrophil cytoplasmic antibody stimulated neutrophils. MPO is anti-myeloperoxidase antibody.

Inhibition of Degranulation by Compound b in TNF/Antineutrophil Cytoplasmic Antibody Stimulated Neutrophils Neutrophils were isolated from healthy human donors using Polymorphprep (Axis Shield). Cells were preincubated with cytochalasin B at 5 ug/ml for 5 minutes at 37° C. Vehicle or compound at 10 ug/ml was added and reactions aliquoted into wells of a 96 well strip plate. TNFα or vehicle was added to a concentration of 200 ng/ml and reactions stimulated for 15 minutes at 37° C. Anti-MPO or vehicle were added and reactions incubated at 37° C. for 1 hr. Supernatants were removed and any remaining cells removed by centrifugation. The resulting supernatants were assayed in a commercial lactoferrin ELISA. (Oxis International.) Results are shown as ng/ml lactoferrin. MPO is anti-myeloperoxidase antibody. Results are shown in FIG. 9.

Compound a Inhibition of Zymosan Phagocytosis by Neutrophils

Figure 10:
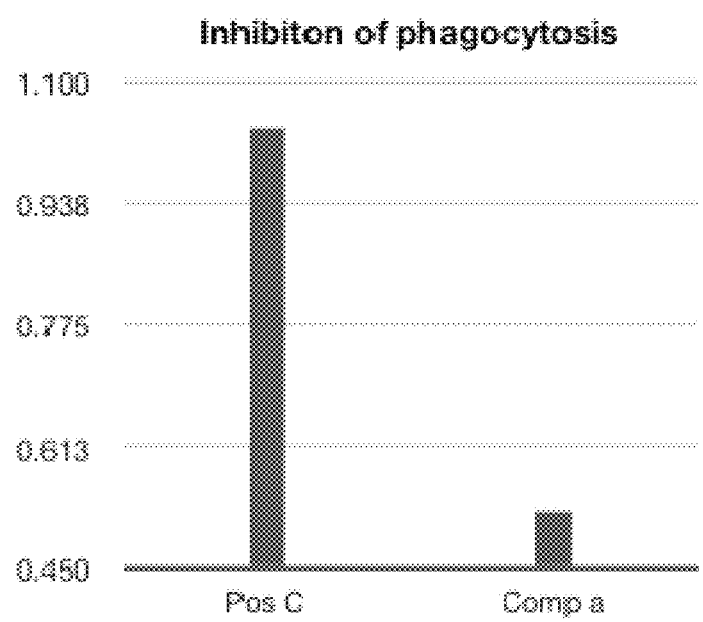
FIG. 10 is a chart showing Compound a), referred to herein as Compound 1, inhibition of zymosan phagocytosis by neutrophils. Results are shown as optical density corrected for number of cells in the respective wells.

Neutrophils were isolated from healthy human donors using Polymorphprep (Axis Shield). Cells were equilibrated for 15 minutes at 37° C. in the presence or absence of 10 ug/ml compound, then plated into 96 well plates previously coated with 2 ng/ml fibrinogen. The subsequent phagocytosis assay was carried out using a commercial phagocytosis assay (CytoSelect™ 96-Well Phagocytosis Assay (Zymosan), Cell Biolabs.) Briefly, cells were incubated with zymosan at 37° C. for 1.5 hrs., fixed with 8% formaldehyde for 5 minutes at room temperature, blocked, permeabilized and detection reagent added which detects phagocytosed zymosan. The reaction was developed by adding a substrate and the resulting colorimetric product was detected in a plate reader. ODs were corrected for relative confluence of the cells based on a visual estimate of confluence. Results are reported as corrected ODs. Results are shown in FIG. 10.

Figure 11:
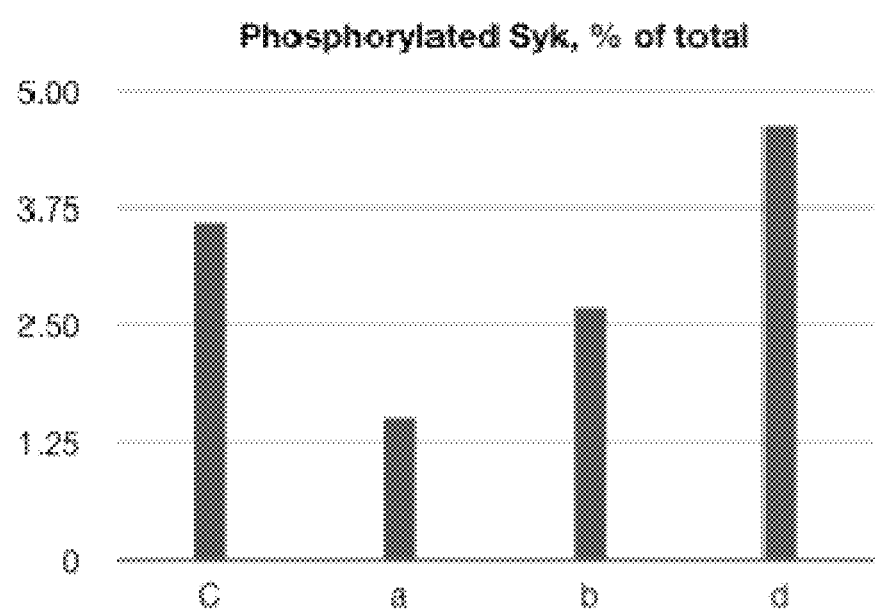
FIG. 11 is a chart showing the inhibition of syk phosphorylation in integrin/TNF stimulated neutrophils, following administration of Compounds a) and b), referred to herein as Compounds 1 and 2, respectively. Results are shown as percent of control and were corrected for number of cells in the respective wells.

Compound a and b Inhibition of syk Phosphorylation in Integrin/TNF Stimulated Neutrophils Neutrophils were isolated from healthy human donors using Polymorphprep (Axis Shield). Cells were equilibrated for 15 minutes at 37° C. in the presence or absence of 10 ug/ml compound. TNFα was added to a concentration of 200 ng/ml and cells dispensed into a 96 well strip plate previously coated with 2 mg/ml fibrinogen at $1 \times 10^6$ cells/well. Reactions were incubated at 37° C. for 1 hr., and cells fixed with 4% formaldehyde for 20 minutes at room temperature. The subsequent assay was performed using a commercial in cell Western blot kit (FACEMaker In Cell Western, Active Motif.) Briefly, fixed cells were quenched according to kit instructions followed by incubation with primary antibodies to either total syk (C-20, Santa Cruz Biotechnology) or to phosphorylated syk (Syk Phospho (pY525/526) Rabbit Monoclonal, Epitomics.) Removal of the primary antibody was followed by a goat anti-rabbit antibody conjugated to HRP. The reaction was developed using the kit developing solution and the resulting colorimetric product read in a plate reader at 450 nm with a 650 nm reference. Cells were then washed and stained with crystal violet to correct for cell number. Results are shown as the percent of total syk that is phosphorylated in each treatment. Results are shown in FIG. 11.

While the invention has been described in detail and with reference to specific examples thereof, it will be apparent to one skilled in the art that various changes and modifications can be made therein without departing from the spirit and scope thereof.

All references cited herein are incorporated herein by reference in their entireties.

The invention claimed is:

1. A method of inhibiting degranulation, inhibiting respiratory burst, or inhibiting Syk phosphorylation by administering a compound of Formula b) or its isomeric form, to a patient in need of such inhibition, wherein inhibition of degranulation, respiratory burst, or Syk phosphorylation is effective for treating cancer or other proliferative disease, genitourinary disease, hepatic disease, pancreatic disease, pulmonary disease, gastrointestinal disease, osteoporosis, inflammation, allergic reaction, or cardiovascular disease, in the patient, and wherein the compound of Formula b) or its isomeric form have the following formulas:

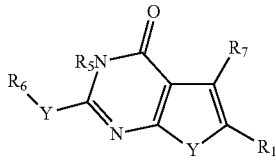

Formula b)
or:

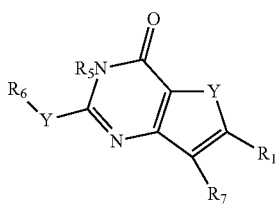

Isomeric form wherein:
$R_1$ and $R_2$ are independently selected from the group consisting of —C(O)OR$_5$, —C(S)OR$_5$, —C(NR$_5$)OR$_5$, —C(O)SR$_5$, —C(S)SR$_5$, —C(NR$_5$)SR$_5$, —C(O)N(R$_5$)$_2$, —C(S)N(R$_5$)$_2$, —C(NR$_5$)N(R$_5$)$_2$, —N(R$_5$)C(O)OR$_5$, —N(R$_5$)C(S)OR$_5$, —N(R$_5$)C(NR$_5$)OR$_5$, —N(R$_5$)C(O)SR$_5$, —N(R$_5$)C(S)SR$_5$, —N(R$_5$)C(NR$_5$)SR$_5$, —N(R$_5$)C(O)N(R$_5$)$_2$, —N(R$_5$)C(S)N(R$_5$)$_2$, —N(R$_5$)C(NR$_5$) N(R$_5$)$_2$, —NO$_2$, —SOR$_5$, —SO$_2$R$_5$, —SO$_3$R$_5$, —CN, —PO$_4$R$_5$, —C(O)R$_5$, —C(S)R$_5$, and —C(NR$_5$)R$_5$, Y is O, S, or NR$_5$, R$_5$ is a substituent selected from the group consisting of H, —C$_{1-6}$ alkyl, —C$_{1-6}$ alkylaryl, -aryl-C$_{1-6}$ alkyl, —C$_{1-6}$ alkylheteroaryl, -heteroaryl-C$_{1-6}$alkyl, -aryl, and -heteroaryl, R$_6$ is C$_{1-6}$-alkylaryl, C$_{1-6}$-alkylheteroaryl, aryl, or heteroaryl, wherein the aryl or heteroaryl ring in the aryl, aralkyl, alkheteroaryl, or heteroaryl substituents is optionally substituted with one to three substituents, Z, as described above, wherein in one embodiment, the substituent, Z, is a substituent defined as R$^2$ herein, and in another embodiment, is defined as being selected from the group consisting of C(S)OR$_5$, —C(NR$_5$)OR$_5$, —C(O)SR$_5$, —C(S)SR$_5$, —C(NR$_5$)SR$_5$, —C(O)N(R$_5$)$_2$, —C(S)N (R$_5$)$_2$, —C(NR$_5$)N(R$_5$)$_2$, —N(R$_5$)C(O)OR$_5$, —N(R$_5$)C (S)OR$_5$, —N(R$_5$)C(NR$_5$)OR$_5$, —N(R$_5$)C(O)SR$_5$, —N(R$_5$)C(S)SR$_5$, —N(R$_5$)C(NR$_5$)SR$_5$, —N(R$_5$)C(O) N(R$_5$)$_2$, —N(R$_5$)C(S)N(R$_5$)$_2$, —N(R$_5$)C(NR$_5$) N(R$_5$)$_2$, —SOR$_5$, —SO$_2$R$_5$, —SO$_3$R$_5$, —PO$_4$R$_5$, —C(O)R$_5$, —C(S)R$_5$, and —C(NR$_5$)R$_5$, and R$_7$ is a substituent selected from the group consisting of H, —C$_{1-6}$ alkyl, —C$_{1-6}$ alkylaryl, -aryl-C$_{1-6}$ alkyl, —C$_{1-6}$ alkylheteroaryl, -heteroaryl—C$_{1-6}$alkyl, -aryl, and -heteroaryl, and polymorphs, salts, hydrates, and solvates thereof, wherein the compound is a kinase inhibitor.

2. The method of claim 1, wherein the patient is a human suffering from a condition selected from the group consisting of an allergic disease, low grade scarring, a disease associated with tissue destruction, a disease associated with tissue inflammation, and inflammation.

3. The method of claim 2, wherein the inflammation is caused by a disorder selected from the group consisting of conjunctivitis, rhinitis, asthma, atopic dermatitis and food allergies.

4. The method of claim 2, wherein the disease associated with tissue inflammation is selected from the group consisting of irritable bowel, spastic colon, inflammatory colon disease, vasculitis, lupus, gout and rhuematoid arthritis.

5. The method of claim 1, wherein the compound has the following formula:

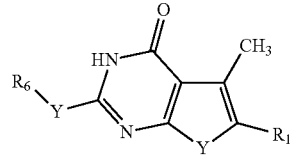

wherein Y, $R_1$ and $R_6$ are as defined in claim 1.

6. The method of claim 1, wherein the compound has the following formula:

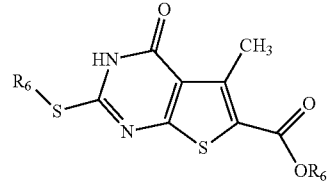

wherein Y, $R_5$ and $R_6$ are as defined in claim 1.

7. The method of claim 1, wherein the compound has the following formula:

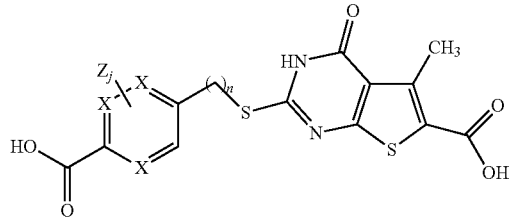

wherein:
Z is selected from the group consisting of C$_{1-6}$ alkyl, alkenyl, heterocyclyl, aryl, heteroaryl, halo, —OR', —NR'R", —CF$_3$, —CN, —NO$_2$, —C$_2$R', —SR', —N$_3$, —C(=O)NR'R", —NR'C(=O) R", —C(=O)R', —C(=O)OR', —OC(=O)R', —OC(=O)NR'R", —NR'C(=O)O R", —SO$_2$R', —SO$_2$NR'R", and —NR'SO$_2$R", where R' and R" are individually hydrogen, C$_{1-6}$ alkyl, cycloalkyl, heterocyclyl, aryl, or arylalkyl, wherein the aryl or heteroaryl rings can be substituted at any free position with Z, j is an integer from 0 to the number of available positions on the aryl or heteroaryl ring to which the Z substituent is attached, X is, individually, N, or C bonded to H or a substituent Z, and, in one embodiment, no more than two X are N within any ring structure, and
n is an integer of from 1 to 3.
8. The method of claim 1, wherein the compound has the following structure:
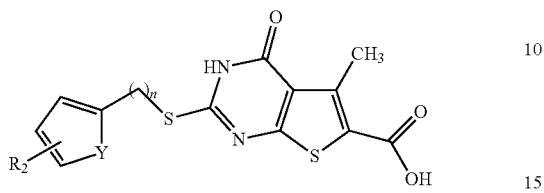
wherein $R_2$ and Y are as defined in claim 1.
9. The method of claim 1, wherein the compound has the following structure:
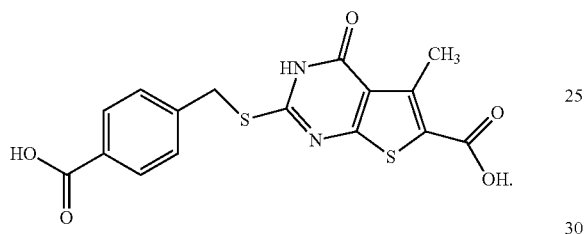
* * * * *